US011364238B2

(12) United States Patent
Zisman

(10) Patent No.: US 11,364,238 B2
(45) Date of Patent: *Jun. 21, 2022

(54) COMBINATION THERAPY FOR TREATING PULMONARY HYPERTENSION

(71) Applicant: Pulmokine, Inc., Troy, NY (US)

(72) Inventor: Lawrence S. Zisman, Slingerlands, NY (US)

(73) Assignee: PULMOKINE, INC., Troy, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/578,084

(22) Filed: Sep. 20, 2019

(65) Prior Publication Data
US 2020/0261448 A1 Aug. 20, 2020

Related U.S. Application Data

(63) Continuation of application No. 16/256,213, filed on Jan. 24, 2019, now abandoned, which is a continuation of application No. 15/796,083, filed on Oct. 27, 2017, now Pat. No. 10,231,966.

(60) Provisional application No. 62/413,788, filed on Oct. 27, 2016.

(51) Int. Cl.
A61K 31/497 (2006.01)
A61K 45/06 (2006.01)
A61P 9/12 (2006.01)
A61K 9/00 (2006.01)
A61K 31/4985 (2006.01)
A61K 31/505 (2006.01)

(52) U.S. Cl.
CPC .......... A61K 31/497 (2013.01); A61K 9/0075 (2013.01); A61K 31/4985 (2013.01); A61K 31/505 (2013.01); A61K 45/06 (2013.01); A61P 9/12 (2018.01)

(58) Field of Classification Search
CPC .... A61K 31/497; A61K 45/06; A61K 9/0075; A61K 31/4985; A61K 31/505; A61P 9/12
See application file for complete search history.

(56) References Cited

U.S. PATENT DOCUMENTS

| 4,570,630 | A | 2/1986 | Elliott et al. |
| 5,093,340 | A | 3/1992 | Mohrs et al. |
| 5,648,369 | A | 7/1997 | Kadaba |
| 6,329,386 | B1 | 12/2001 | Mollison |
| 6,635,641 | B2 | 10/2003 | Bender et al. |
| 7,122,550 | B2 | 10/2006 | Burns et al. |
| 7,259,179 | B2 | 8/2007 | Burns et al. |
| 7,511,047 | B2 | 3/2009 | Burns et al. |
| 7,598,272 | B2 | 10/2009 | Burns et al. |
| 8,084,456 | B2 | 12/2011 | Burns et al. |
| 8,257,741 | B2 | 9/2012 | Curatolo et al. |
| 8,263,128 | B2 | 9/2012 | Curatolo et al. |
| 8,268,850 | B2 | 9/2012 | Li et al. |
| 8,288,540 | B2 | 10/2012 | Chianelli et al. |
| 8,293,757 | B2 | 10/2012 | Molteni et al. |
| 8,338,417 | B2 | 12/2012 | Li et al. |
| 8,378,108 | B2 | 2/2013 | Corkey et al. |
| 8,410,173 | B2 | 4/2013 | Zisman |
| 8,461,161 | B2 | 6/2013 | Burns et al. |
| 8,569,283 | B2 | 10/2013 | Molteni et al. |
| 8,889,700 | B2 | 11/2014 | Von et al. |
| 9,029,386 | B2 | 5/2015 | Burns et al. |
| 9,199,981 | B2 | 12/2015 | Yeh et al. |
| 9,815,815 | B2 | 11/2017 | Zisman |
| 2002/0120011 | A1 | 8/2002 | Sikorski et al. |
| 2004/0018243 | A1 | 1/2004 | Basu et al. |
| 2006/0154936 | A1 | 7/2006 | Lasky |
| 2007/0099935 | A1 | 5/2007 | Burns et al. |
| 2007/0161635 | A1 | 7/2007 | Burns et al. |
| 2008/0268460 | A1 | 10/2008 | Loganzo et al. |
| 2009/0197922 | A1 | 8/2009 | Maitland et al. |
| 2010/0130447 | A1* | 5/2010 | Burns .................. C07D 409/14 514/85 |
| 2011/0117159 | A1 | 5/2011 | Zisman |
| 2011/0190313 | A1 | 8/2011 | Pascoe et al. |
| 2013/0137660 | A1 | 5/2013 | Burns et al. |
| 2014/0038988 | A1 | 2/2014 | Von et al. |
| 2014/0275098 | A1 | 9/2014 | Belardinelli et al. |
| 2015/0044288 | A1 | 2/2015 | Surber |
| 2015/0352111 | A1 | 12/2015 | Zisman |
| 2016/0235742 | A1 | 8/2016 | Zisman |

FOREIGN PATENT DOCUMENTS

| EP | 1522314 A1 | 4/2005 |
| EP | 1948176 B1 | 1/2011 |
| GB | 2011892 A | 7/1979 |
| JP | S5461189 A | 5/1979 |
| JP | H09268169 A | 10/1997 |
| JP | 2005535596 A | 11/2005 |
| JP | 2005538975 A | 12/2005 |
| JP | 2006111553 A | 4/2006 |
| JP | 2010509375 A | 3/2010 |
| JP | 2016506417 A | 3/2016 |
| WO | WO-9708135 A1 | 3/1997 |
| WO | WO-0128993 A2 | 4/2001 |
| WO | WO-0129025 A2 | 4/2001 |
| WO | WO-0153274 A1 | 7/2001 |
| WO | WO-0162251 A1 | 8/2001 |
| WO | WO-0162252 A1 | 8/2001 |

(Continued)

OTHER PUBLICATIONS

Minatsuki et al., "Platelet-Derived Growth Factor Receptor-Tyrosine Kinase Inhibitor, Imatinib, Is Effective for Treating Pulmonary Hypertension Induced by Pulmonary Tumor Thrombotic Microangiopathy", Internatonal Heart Journal, vol. 56, No. 2, Jan. 1, 2015, pp. 245-248.

(Continued)

Primary Examiner — Sahar Javanmard
(74) Attorney, Agent, or Firm — Seed IP Law Group LLP

(57) ABSTRACT

The present disclosure describes a method of treating pulmonary disorders, such as pulmonary arterial hypertension, using a combination of a PDGF receptor kinase inhibitor, PDEV inhibitor, and an endothelin receptor antagonist. The compounds can inhibit cell growth and proliferation and target the underlying pathology of PAH.

21 Claims, 21 Drawing Sheets

Specification includes a Sequence Listing.

(56) References Cited

FOREIGN PATENT DOCUMENTS

| WO | WO-02060492 | A1 | 8/2002 |
|---|---|---|---|
| WO | WO-03000666 | A1 | 1/2003 |
| WO | WO-03099706 | A1 | 12/2003 |
| WO | WO-03099796 | A1 | 12/2003 |
| WO | WO-03099811 | A1 | 12/2003 |
| WO | WO-2004004720 | A1 | 1/2004 |
| WO | WO-2004006858 | A2 | 1/2004 |
| WO | WO-2004052868 | A1 | 6/2004 |
| WO | WO-2005002673 | A1 | 1/2005 |
| WO | WO-2005011594 | A2 | 2/2005 |
| WO | WO-2005013982 | A1 | 2/2005 |
| WO | WO-2005047244 | A2 | 5/2005 |
| WO | WO-2005054199 | A1 | 6/2005 |
| WO | WO-2005066156 | A1 | 7/2005 |
| WO | 2006/026395 | A1 | 3/2006 |
| WO | WO-2007124382 | A2 | 11/2007 |
| WO | WO-2008058341 | A1 | 5/2008 |
| WO | WO-2010102065 | A1 | 9/2010 |
| WO | WO-2010102066 | A1 | 9/2010 |
| WO | WO-2010132827 | A1 | 11/2010 |
| WO | WO-2012031129 | A2 | 3/2012 |
| WO | WO-2012040502 | A1 | 3/2012 |
| WO | WO-2012106575 | A1 | 8/2012 |
| WO | WO-2012159103 | A1 | 11/2012 |
| WO | WO-2014110198 | A2 | 7/2014 |
| WO | WO-2014110200 | A1 | 7/2014 |
| WO | WO-2015179369 | A1 | 11/2015 |

OTHER PUBLICATIONS

Selej et al., "Development of macitentan for the treatment of pulmonary arterial hypertension", Annals of the New York Academy of Sciences, 2015, pp. 68-81.

Abe, et al. Formation of plexiform lesions in experimental severe pulmonary arterial hypertension. Circulation. Jun. 2, 20109;121(25):2747-54. doi: 10.1161/CIRCULATIONAHA.109.927681. Epub Jun. 1, 20104.

Barf, et al. Irreversible protein kinase inhibitors: balancing the benefits and risks. J Med Chern. Jul. 2, 20126;55(14):6243-62. doi: 10.1021/jm3003203. Epub Jun. 8, 2012.

Barst RJ. PDGF signaling in pulmonary arterial hypertension. J Clin Invest. 2005;115(10):2691-4.

Burns, et al., Discovery of 2- (α- methylbenzylamino) pyrazines as potent Type II inhibitors of FMS. Bioorganic & Medicinal Chemistry letters. 19(2009):1206-1209.

Cavasin, et al., Reversal of severe angioproliferative pulmonary arterial hypertension and right ventricular hypertrophy by combined phosphodiesterase-5 and endothelin receptor inhibition. J Transl Med 2014;12:314.

Chen, et al. A cell-based immunocytochemical assay for monitoring kinase signaling pathways and drug efficacy. Anal Biochem. Mar. 1, 2005;338(1):136-42.

Choy, G. et al., Safety, tolerability, and pharmacokinetics of amuvatinib from three phase 1 clinical studies in healthy volunteers, Cancer chemotherapy and pharmacology springer, Berlin, DE, 70(1); Feb. 15, 2012: 183-190, XP035077226, ISSN:1432-0843, D0l:10.1007/S00280-012-1821-2, Abstract, p. 184, paragraph investigational agent: amuvatinib.

Ciuclan, et al. Imatinib attenuates hypoxia-induced pulmonary arterial hypertension pathology via reduction in 5-hydroxytryptamine through inhibition of tryptophan hydroxylase 1 expression. Am J Respir Crit Care Med. Jan. 1, 2013;187(1):78-89. doi: 10.1164/rccm.201206-1028OC. Epub Oct. 1, 20128.

Claesson-Welsh, et al. cDNA cloning and expression of a human platelet-derived growth factor (PDGF) receptor specific for B-chain-containing PDGF molecules. Mol Cell Biol. Aug. 1988;8(8):3476-86.

Claesson-Welsh, et al., Platelet-derived growth factor Three isoforms that bind to two distinct cell surface receptors. Acta oncologica 1989;28:331-334.

Claesson-Welsh, et al., Signal transduction by the PDGF receptors. Progress in growth factor research 1994;5:37-54.

Cool, et al. Pathogenesis and evolution of plexiform lesions in pulmonary hypertension associated with scleroderma and human immunodeficiency virus infection. Hum Pathol. Apr. 1997;28(4):434-42.

Co-pending U.S. Appl. No. 15/660,551, filed Jul. 26, 2017.

Co-pending U.S. Appl. No. 15/809,054, filed Nov. 10, 2017.

Dahal, et al. Hypoxic pulmonary hypertension in mice with constitutively active platelet-derived growth factor receptor-β. Pulm Circ. Apr.-Jun. 2011;1(2):259-68. doi: 10.4103/2045-8932.83448.

Deininger, et al. The development of imatinib as a therapeutic agent for chronic myeloid leukemia. Blood. Apr. 1, 2005;105(7):2640-53. Epub Dec. 2, 20043.

Diller, et al. Kinases, homology models, and high throughput docking. J Med Chem. Oct. 2, 20033;46(22):4638-47.

Discafani, et al. Irreversible inhibition of epidermal growth factor receptor tyrosine kinase with in vivo activity by N-[4-[(3-bromophenyl)amino]-6-quinazolinyl]-2-butynamide (CL-387,785). Biochem Pharmacol. Apr. 15, 1999;57(8):917-25.

Duret, C. et al., New respirable and fast dissolving itraconazole dry powder composition for the treatment of invasive pulmonary aspergillosis. Pharmaceutical research, Kluwer Academic publishers-plenum publishers, nl. 29(10); May 30, 2012: 2845-2859, XP03511465, ISSN:1573-904X, DOI: 10.1007/S11095-012-0779-4. Abstract. p. 2847, Paragraph materials and ethods.

European search report and opinion dated Jun. 15, 2016 for EP Application No. 14737648.

European Search Report and Written Opinion dated Oct. 12, 2016 for EP Application No. 14737772.5.

European Search Report dated Mar. 31, 2017 EP Application No. 14852309.5.

Fan, et al. Nanofluidic proteomic assay for serial analysis of oncoprotein activation in clinical specimens. Nat Med. May 2009;15(5):566-71. doi: 10.1038/nm.1903. Epub Apr. 1, 20092.

Fisher, et al. Clinical differences between idiopathic and scleroderma-related pulmonary hypertension. Arthritis Rheum. Sep. 2006;54(9):3043-50.

Fry, et al. Specific, irreversible inactivation of the epidermal growth factor receptor and erbB2, by a new class of tyrosine kinase inhibitor. Proc Natl Acad Sci USA. Sep. 29, 1998;95(20):12022-7.

Galie, et al., Initial Use of Ambrisentan plus Tadalafil in Pulmonary Arterial Hypertension. N Engl J Med 2015;373:834-44.

Galie, et al., The Fifth World Symposium on Pulmonary Hypertension. J Am Coll Cardiol 2013;62:D1-3.

Ghofrani, et al. Imatinib for the treatment of pulmonary arterial hypertension. N Engl J Med. Sep. 29, 2005;353(13):1412-3.

Ghofrani, et al. Imatinib in pulmonary arterial hypertension patients with inadequate response to established therapy. Am J RespirCrit Care Med. Nov. 1, 2010;182(9):1171-7. doi: 10.1164/rccm.201001-0123OC. Epub Jun. 2, 20105.

Ghofrani, et al. Riociguat for pulmonary hypertension. N Engl J Med. Dec. 5, 2013;369(23):2268. doi: 10.1056/NEJMc1312903.

Greene, et al. Protective Groups in Organic Synthesis. John Wiley & Sons, New York, NY, (3rd Edition, 1999).

Grimminger, et al. PDGF receptor and its antagonists: role in treatment of PAH. Adv Exp Med Biol. 2010;661:435-46. doi: 10.1007/978-1-60761-500-2_28.

Gronwald, et al. Cloning and expression of a cDNA coding for the human platelet-derived growth factor receptor: evidence for more than one receptor class. Proc Natl Acad Sci USA. May 1988;85(10):3435-9.

Hartwig. Transition metal catalyzed synthesis of arylamines and aryl ethers from aryl halides and triflates: Scope and mechanism. Angew. Chern. Int. Ed. Aug. 17, 1998; 37(15):2046-2067.

Hoeper, et al. Imatinib mesylate as add-on therapy for pulmonary arterial hypertension: results of the randomized IMPRES study. Circulation. Mar. 12, 2013;127(10):1128-38. doi: 10.1161/CIRCULATIONAHA.112.000765. Epub Feb. 1, 20132.

(56) References Cited

OTHER PUBLICATIONS

Homma, et al. Involvement of RhoA/Rho kinase signaling in protection against monocrotaline-induced pulmonary hypertension in pneumonectomized rats by dehydroepiandrosterone. Am J Physiol Lung Cell Mol Physiol. 2008; 295:L71-8. DOI: 10.1152/ajplung. 90251.200.
Humbert, et al., Combination of bosentan with epoprostenol in pulmonary arterial hypertension: BREATHE-2. Eur Respir J 2004; 24: 353-359 DOI: 10.1183/09031936.04.00028404.
International search report and written opinion dated Jan. 9, 2015 for PCT/US2014/060039.
International search report and written opinion dated Jun. 20, 2014 for PCT/US2014/010778.
International search report and written opinion dated Nov. 20, 2014 for PCT/US2014/010773.
International search report dated Jan. 9, 2008 for PCT/AU2007/001761.
Jasmin, et al. Short-term administration of a cell-permeable caveolin-1 peptide prevents the development of monocrotaline-induced pulmonary hypertension and right ventricular hypertrophy. Circulation. Aug. 29, 2006;114(9):912-20.
Kanno, et al. Angiotensin-converting enzyme inhibitor preserves p21 and endothelial nitric oxide synthase expression in monocrotaline-induced pulmonary arterial hypertension in rats. Circulation. Aug. 21, 2001;104(8):945-50.
Kumada, et al. Phosphine-nickel complex catalyzed crosscoupling of grignard reagents with aryl and alkenyl halides: 1,2-dibutylbenezne. Organic Syntheses, Coll. vol. 6, p. 407 (1988); vol. 58, p. 127 (1978). DOI:10.15227/orgsyn.058.0127.
KUSANO. Treatment for pulmonary hypertension including lung transplantation. Gen Thorac Cardiovasc Surg. Aug. 2011;59(8):538-46. doi: 10.1007/S11748-010-0747-z. Epub Aug. 18, 2011.
La Rosee, et al. Activity of the Bcr-Abl kinase inhibitor PD180970 against clinically relevant Bcr-Abl isoforms that cause resistance to imatinib mesylate (Gleevec, STI571). Cancer Res. Dec. 15, 2002;62(24):7149-53.
Laskowski, et al. Procheck: a program to check the sterochemical quality of protein structures. Journal of Applied Crystallography 1993;26:283-91.
Launay, et al. Survival in systemic sclerosis-associated pulmonary arterial hypertension in the modern management era. Ann Rheum Dis. Dec. 2013;72(12):1940-6. doi: 10.1136/annrheumdis-2012-202489. Epub Nov. 24, 2012.
Lee, et al. Monoclonal endothelial cell proliferation is present in primary but not secondary pulmonary hypertension. J Clin Invest. Mar. 1, 1998;101(5):927-34.
Leproult, et al. Cysteine mapping in conformationally distinct kinase nucleotide binding sites: application to the design of selective covalent inhibitors. J Med Chem. Mar. 10, 2011;54(5):1347-55. doi: 10.1021/jm101396q. Epub Feb. 15, 2011.
Lymboussaki, et al. Vascular endothelial growth factors and their receptors in embryos, adults and intumors. Academic Dissertation, University of Helsinki, Molecular/Cancer Biology Laboratory and Department of Pathology, Haartman Institute, (1999). 108 pages.
March. Advanced Organic Chemistry: Reactions, Mechanisms and Structure. 4th Ed. pp 352-7, John Wiley & Sons, NY (1992).
Martinho, et al. Expression, mutation and copy No. analysis of platelet-derived growth factor receptor A (PDGFRA) and its ligand PDGFA in gliomas. Br J Cancer. Sep. 15, 2009;101(6):973-82. doi: 10.1038/sj.bjc.6605225. Epub Aug. 25, 2009.
Masri, et al. Hyperproliferative apo ptosis-resistant endothelial cells in idiopathic pulmonary arterial hypertension. Am J Physiol Lung Cell Mol Physiol. Sep. 2007;293(3):L548-54. Epub May 25, 2007.
Matsui, et al. Isolation of a novel receptor cDNA establishes the existence of two PDGF receptor genes. Science. Feb. 10, 1989;243(4892):800-4.
Maurya, et al. Structural models of vanadate-dependent haloperoxidases, their reactivity, immobilization on polymer support and catalytic activities. Journal of Chemical Sciences 123.2 (2011): 215-228.

McLaughlin. Classification and epidemiology of pulmonary hypertension. Cardiol Clin. Aug. 2004;22(3):327-41, v.
McLaughlin, et al., Bosentan added to sildenafil therapy in patients with pulmonary arterial hypertension. Eur Respir J 2015; 46: 405-413 l DOI: 10.1183/13993003.02044-2014.
McLaughlin, et al. Pulmonary arterial hypertension. Curr Probl Cardiol. Dec. 2011;36(12):461-517. doi: 10.1016/j.cpcardiol.2011. 08.002.
Medarametla, et al. PK10453, a nonselective platelet-derived growth factor receptor inhibitor, prevents the progression of pulmonary arterial hypertension. Pulm Circ. Mar. 2014;4(1):82-102. doi: 10.1086/674881.
Miyaura, et al. Palladium-Catalyzed Cross-Coupling Reactions of Organoboron Compounds. Chem. Rev.. 1995; 95(7):2457-2483.
Montani, et al. Pulmonary arterial hypertension. Orphanet J Rare Dis. Jul. 6, 2013;8:97. doi: 10.1186/1750-1172-8-97.
Montani, et al. Targeted therapies in pulmonary arterial hypertension. Pharmacol Ther. Feb. 2014;141 (2):172-91. doi: 10.1016/j. pharmthera.2013.10.002. Epub Oct. 14, 2013.
Moren, et al. Aerosols in medicine : principles, diagnosis, and therapy. Amsterdam; New York: Elsevier, xx, 429 (1993).
Mustonen, et al. Endothelial receptor tyrosine kinases involved in angiogenesis. J Cell Biol. May 1995;129(4):895-8.
Negishi. A genealogy of Pd-catalyzed cross-coupling. Journal of organometallic chemistry 653.1 (2002): 34-40.
Notice of Allowance dated May 1, 2017 for U.S. Appl. No. 14/760,139.
Notice of Allowance dated Aug. 10, 2017 for U.S. Appl. No. 15/028,347.
Oballa, et al. A generally applicable method for assessing the electrophilicity and reactivity of diverse nitrile-containing compounds. Bioorg Med Chem Lett. Feb. 15, 2007;17(4):998-1002. Epub Nov. 17, 2006.
Office Action dated Jan. 20, 2017 for U.S. Appl. No. 15/028,347.
Office Action dated Apr. 10, 2017 for U.S. Appl. No. 14/760,165.
Office action dated Aug. 24, 2016 for U.S. Appl. No. 14/760,139.
Ogawa, et al. Inhibition of mTOR attenuates store-operated Ca2+ entry in cells from endarterectomized tissues of patients with chronic thromboembolic pulmonary hypertension. Am J Physiol Lung Cell Mol Physiol. Oct. 2009;297(4):L666-76. doi: 10.1152/ajplung.90548.2008. Epub Jul. 24, 2009.
Ogawa, et al. PDGF enhances store-operated Ca2+ entry by upregulating STIM1/Orai1 via activation of Akt/mTOR in human pulmonary arterial smooth muscle cells. Am J Physiol Cell Physiol. Jan. 1, 20125;302(2):C405-11. doi: 10.1152/ajpcell.00337.2011. Epub Oct. 26, 2011.
Paniaqua, et al. Imatinib for the treatment of rheumatic diseases. Nat Clin Pract Rheumatol. Apr. 2007;3(4):190-1.
Panzhinskiy, et al. Hypoxia induces unique proliferative response in adventitial fibroblasts by activating PDGFβ receptor-JNK1 signalling. Cardiovasc Res. Aug. 1, 2012;95(3):356-65. doi: 10.1093/cvr/cvs194. Epub Jun. 2, 20126.
Pao, et al. Acquired resistance of lung adenocarcinomas to gefitinib or erlotinib is associated with a second mutation in the EGFR kinase domain. PLoS Med. Mar. 2005;2(3):e73. Epub Feb. 2, 20052.
Perros, et al. Platelet-derived growth factor expression and function in idiopathic pulmonary arterial hypertension. Am J Respir Crit Care Med. Jul. 1, 2008;178(1):81-8. doi: 10.1164/rccm.200707-1037OC. Epub Apr. 1, 20087.
Phalen, et al. Inhalation exposure methodology. Environ Health Perspect. Jun. 1984;56:23-34.
Pinchuk, et al. Marine derived hamacanthins as lead for the development of novel PDGFRβ protein kinase inhibitors. Mar Drugs. Aug. 2, 20136;11 (9):3209-23. doi: 10.3390/md11093209.
Pulido, et al. Macitentan and morbidity and mortality in pulmonary arterial hypertension. N Engl J Med. Aug. 2, 20139;369(9):809-18. doi: 10.1056/NEJMoa1213917.
Pulido, et al. Macitentan and pulmonary arterial hypertension. N Engl J Med. Jan. 2, 2014;370(1):82-3. doi: 10.1056/NEJMc1313112.
Purandare, et al. Identification of chemokine receptor CCR4 antagonist. Bioorg Med Chem Lett. May 1, 20056;15(10):2669-72. DOI:10. 1016/j.bmcl.2005.02.084.

(56) References Cited

OTHER PUBLICATIONS

Remington: The Science and Practice of Pharmacy, 21st Ed. Lippincott Williams & Wilkins (2005).
Rubin, et al. A paradigm shift in pulmonary arterial hypertension management. Eur Respir Rev. Dec. 2013;22(130):423-6. doi: 10.1183/09059180.00006913.
Sakagami, et al. In vivo, in vitro and ex vivo models to assess pulmonary absorption and disposition of inhaled therapeutics for systemic delivery. Adv Drug Deliv Rev. Oct. 31, 2006;58(9-10):1030-60. Epub Aug. 15, 2006.
Sakao, et al. Reversible or irreversible remodeling in pulmonary arterial hypertension. Am J Respir Cell Mol Biol. Dec. 2010;43(6):629-34. doi: 10.1165/rcmb.2009-0389TR. Epub Dec. 11, 2009.
Schermuly, et al. Reversal of experimental pulmonary hypertension by PDGF inhibition. J Clin Invest. Oct. 2005;115(10):2811-21.
Seferian, et al. Therapies for pulmonary arterial hypertension: where are we today, where do we go tomorrow? Eur Respir Rev. Sep. 1, 2013;22(129):217-26. doi: 10.1183/09059180.00001713.
Shah, et al. Overriding imatinib resistance with a novel ABL kinase inhibitor. Science. Jul. 16, 2004;305(5682):399-401.
Simonneau, et al. Updated clinical classification of pulmonary hypertension. J Am Coll Cardiol. Dec. 24, 2013;62(25 Suppl):D34-41. doi: 10.1016/j.jacc.2013.10.029.
Sitbon, et al. Upfront triple combination therapy in pulmonary arterial hypertension: a pilot study. Eur Respir J. Jun. 2014;43(6):1691-7. doi: 10.1183/09031936.00116313. Epub Mar. 13, 2014.
Smolich, et al. The antiangiogenic protein kinase inhibitors SU5416 and SU6668 inhibit the SCF receptor (c-kit) in a human myeloid leukemia cell line and in acute myeloid leukemia blasts. Blood. Mar. 1, 2001;97(5):1413-21.
Souza, et al. Long term imatinib treatment in pulmonary arterial hypertension. Thorax. Aug. 2006;61(8):736.
STILLE. The Palladium-Catalyzed Cross-Coupling Reactions of Organotin Reagents with Organic Electrophiles [New Synthetic Methods (58)]. Angew. Chem. Int. Ed. Jun. 1986; 25(6):508-524.
Takatsuki, et al. Clinical safety, pharmacokinetics, and efficacy of ambrisentan therapy in children with pulmonary arterial hypertension. Pediatr Pulmonol. Jan. 2013;48(1):27-34. doi: 10.1002/ppul.22555. Epub Apr. 17, 2012.
Thompson, et al. Clustal W: improving the sensitivity of progressive multiple sequence alignment through sequence weighting, position-specific gap penalties and weight matrix choice. Nucleic Acids Res. Nov. 11, 1994;22(22):4673-80.
Tuder, et al. Plexiform lesion in severe pulmonary hypertension: association with glomeruloid lesion. Am J Pathol. Jul. 2001;159(1):382-3.
Ukrainets, et al. 2-Carbethoxymethyl-4H-3, 1-Benzoxazin-4-One. 3.* Condensation of o-Phenylenediamine. Khimiya Geterotsiklicheskikh Soedinii, 2, 239-241(1992).
Ukrainets, et al. 4-Hydroxy-2-Quinolones. 16.* Condensation of NR-Substituted Amides of 2-Carboxy-Malonanilic Acid Withoff-Phenylenediamine. translated from Khimiya Geterotsiklicheskikh Soedinii 8 (1993): 1105-1108.
Ukrainets, et al. 4-Hydroxy-2-quinolones. 32. Synthesis and antithyroid activity of thio analogs of 1H-2-oxo-3-(2-Benzimidazolyl)-4-hydroxyquinoline. Chemistry of Heterocyclic Compounds 33.5 (1997): 600-604.
Ukrainets, et al. 4-Hydroxy-2-Quinolones. 7.* Synthesis and Biological Properties of 1-R-3-(2-Benzimidazolyl)-4-Hydroxy-2-Quinolones. Khimiya Geterotsiklicheskikh Soedinii, 1,105-108 (1993).
Ukrainets, et al. Effective synthesis of 3-(Benzimidazol-2-yl)-4-hydroxy-2-oxo-1, 2-dihydroquinolines. Tetrahedron letters 36.42 (1995): 7747-7748.
Ullrich, et al. Signal transduction by receptors with tyrosine kinase activity. Cell. Apr. 20, 1990;61(2):203-12.
Van Der Geer, et al. Receptor protein-tyrosine kinases and their signal transduction pathways. Annu Rev Cell Biol. 1994;10:251-337.
Westermark, et al., Structural and functional aspects of the receptors for platelet-derived growth factor. Progress in growth factor research 1989;1:253-66.
White, et al. Plexiform-like lesions and increased tissue factor expression in a rat model of severe pulmonary arterial hypertension. Am J Physiol Lung Cell Mol Physiol. Sep. 2007;293(3):L583-90. Epub Jun. 22, 2007.
Wu, et al. Comprehensive dissection of PDGF-PDGFR signaling pathways in PDGFR genetically defined cells. PLoS One. 2008;3(11):e3794. doi: 10.1371/journal.pone.0003794. Epub Nov. 24, 2008.
Yamamoto, et al. Activating mutation of D835 within the activation loop of FLT3 in human hematologic malignancies Blood. Apr. 15, 2001;97(8):2434-9.
Yang, et al. Prevalence of pulmonary arterial hypertension in patients with connective tissue diseases: a systematic review of the literature. Clin Rheumatol. Oct. 2013;32(10):1519-31. doi: 10.1007/s10067-013-2307-2. Epub Jun. 20, 2013.
Yeager, et al. Progenitor cells in pulmonary vascular remodeling. Pulm Circ. Jan.-Mar. 2011;1(1):3-16. doi: 10.4103/2045-8932.78095.
Yi, et al. Distribution of obstructive intimal lesions and their cellular phenotypes in chronic pulmonary hypertension. A morphometric and immunohistochemical study. Am J Respir Crit Care Med. Oct. 2000; 162(4 Pt 1):1577-86.

\* cited by examiner

SEQUENCE LISTING

```
<160> NUMBER OF SEQ ID NOS: 1

<210> SEQ ID NO 1
<211> LENGTH: 1723
<212> TYPE: DNA
<213> ORGANISM: Rattus sp.

<400> SEQUENCE: 1
gtgaagacga accatcggct gccgtgttcc ttttcctctc tgaggttgga gtccctgcg      60 cgcccccaca cggctagacg ccttggctgg ttcgcgacgc agccccaga ccgtggatgc     120 tcgcgtgggc tcgggatccg cccaggtagc ggctttggac cccggtccct cgtccaggtc    180
ctccccaacc ccccagcgac ggagccgggg ccggggcgg cggcgcccgg gggccatgcg     240
ggtgagccgc ggtggcggct gcagcggcct gagctcctga tcgcggcgga cccgagcgga    300
gcccaccctc ctccccagcc cccccaccct ggccgcgggg gcggcgcgct ccgtctacgc    360
gtccggggcc ccgtggggcc gggcccggag tcggcatgaa tcgctgctgg gcgctcttcc    420
tgcctctctg ctgctacctg cgtctggtca gcgctgaggg ggatcccatt cctgaggaac    480
tctatgaaat gctgagtgac cactccatcc gctcctttga tgaccttcag cgcctgctgc    540
acagagactc cgtagacgaa gatggggctg agctggactt gaacatgacc cgagcacatt    600
ctggagtcga gtcggaaagc tcatctcgag ggaggaggag cctagggtct ctggctgcag    660
cagagcctgc cgtaatcgcc gagtgcaaga cgcgtacaga ggtgttccag atctcgcgga    720
acctcatcga tcgcaccaat gccaacttcc tggtgtggcc gccctgcgtg gaggtgcagc    780
gctgctcggg ctgctgcaat aaccgcaatg tgcagtgccg ggcctcgcag gtgcagatgc    840
ggccggtgca ggtgagaaag atcgaaattg tgagaaagaa gccagtcttc aagaaggcca    900
cagtgaccct ggaggaccat ctggcctgca agtgtgagac agtagtgacc cctcggcccg    960
tgactcgaag tcctgggaca tccagggagc atcgagccaa gacacctcaa actcgggtga   1020
ccgttcggac ggtgcgaatc cgccggcccc ccaaagggaa gcaccgaaag tttaagcaca   1080
cccatgacaa gaaggcactg aaggagatcc ttggagccta ggggtgtcag cgagagtgtg   1140
ggcagggtta tttaatatgg tatttgctgt actgccccca tgggtccctt ggagtgataa   1200
tgttgttccc ctcgtccgtc tgtctcgatg cctgattcgg acggccaatg gtgcttccct   1260
```

```
cgccccgcgt gcccagccac ctccaccagc agcaatccct gccctgcagc tccagaagca    1320
aaggaaggac tccactccag gctgctgctt ccctctaccc caagaacctg ggacaagcgt    1380
gcggagcttc acagaggact ggaccggccc cagagcctgg catttagcct gaggacctct    1440
gcatgtcctg cctggttcct ggaccactgg ccagctagca gggaatactt tcaggcaggc    1500
tagggtccct tgcagtcctg tggcagggag cacggactgg aggaactctc atggcaccca    1560
gatctgccac gcactcatct ctccctgtcc ctttagccta cagtggcttt tcattttata    1620
agtatgaaat cgtggaagac atgaactcct ctgggcaggt ggccacatgc cttctctgat    1680
ggattagagg tgcattgtgc ttgtgaaaaa aaaaaaaaaa aaa                      1723
```

COMBINATION THERAPY FOR TREATING PULMONARY HYPERTENSION

CROSS REFERENCE

This application is a continuation of U.S. application Ser. No. 16/256,213, filed Jan. 24, 2019, which application is a continuation of U.S. application Ser. No. 15/796,083, filed Oct. 27, 2017 (now U.S. Pat. No. 10,231,966), which application claims the benefit of U.S. Provisional Application No. 62/413,788, filed Oct. 27, 2016, which is incorporated herein by reference in its entirety.

GOVERNMENT RIGHTS

The invention was made with government support under R44HL102946 by the National Institute of Health. The government has certain rights in the invention.

BACKGROUND

Pulmonary hypertension (PH) is a rare disorder of the pulmonary vasculature that is associated with high morbidity and mortality. The pathology of the disease includes plexiform lesions of disorganized angiogenesis and abnormal neointimal cellular proliferation, which obstruct blood flow through the pulmonary arterioles. Kinases play a critical role in cell growth and proliferation, and can be used to address the underlying pathology of PH. Kinase inhibitors can be used to treat PH.

INCORPORATION BY REFERENCE

Each patent, publication, and non-patent literature cited in the application is hereby incorporated by reference in its entirety as if each was incorporated by reference individually.

SUMMARY OF THE INVENTION

In some embodiments, the invention provides a method of treating a condition, the method comprising administering to a subject in need thereof a therapeutically-effective amount of a tyrosine kinase inhibitor, a therapeutically-effective amount of a phosphodiesterase type 5 (PDEV) inhibitor, and a therapeutically-effective amount of an endothelin receptor antagonist.

DETAILED DESCRIPTION

Pulmonary hypertension (PH), also known as pulmonary arterial hypertension (PAH), is a chronic disease that affects the arteries in the lungs and the right side of the heart. If left untreated, PAH can lead to heart failure; thus, PAH is a disorder associated with high morbidity and mortality. The World Health Organization classifies PH into five groups based on the underlying associated disease: PAH, PH due to left heart disease, PH due to lung diseases and/or hypoxia, chronic thromboembolic PH (CTEPH), and PH with other multifactorial mechanisms.

The pathology of PAH includes complex vascular formations resulting from the remodeling of pulmonary arteries called plexiform lesions and abnormal neointimal cellular proliferation, which obstruct blood flow through the pulmonary arterioles. Kinases play a critical role in cell growth and proliferation, and can be targeted to address the underlying pathology of PAH.

PAH can be associated with several etiologies including familial forms and predisposing genetic abnormalities, such as genetic mutations in the bone morphogenetic type 2 receptor, endoglin, activin-like receptor kinase 1 (ALK1), mothers against decapentaplegic 9 (SMAD 9) and related pathways, autoimmune disorders (e.g., systemic sclerosis and scleroderma), congenital heart disease, liver disease with portal hypertension, and HIV infections. PAH can present a mean pulmonary artery pressure of ≥25 mmHg, and a pulmonary capillary wedge pressure or left ventricular end diastolic pressure of ≤15 mmHg.

Signaling through the platelet derived growth factor (PDGF) pathway can promote the development and progression of PAH. The PDGF receptor (PDGFR) has two major isoforms: α and β. The α and β isoforms of PDGFR can form homodimers (i.e., PDGFRαα and PDGFRββ) and heterodimers (i.e., PDGFRαβ). In some embodiments, PDGFRαα is abbreviated as PDGFRα, and PDGFRββ is abbreviated as PDGFRβ. Signaling through the different PDGFR isoforms can activate different signaling pathways.

Ligands that bind PDGFRs are single chain proteins such as PDGFA and PDGFB, which can also form homodimers and heterodimers. Ligands that bind PDGFRα are PDGFAA, and to a lesser extent, PDGFAB and PDGFBB. PDGFBB is the primary ligand that binds PDGFRβ.

Figure 1:
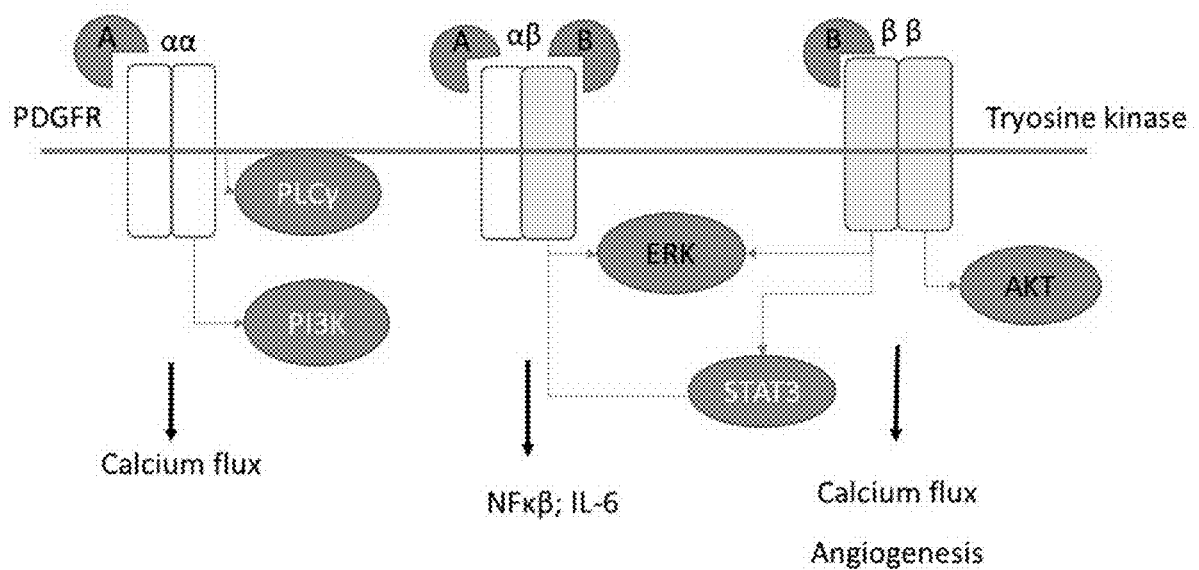
FIG. 1 illustrates the PDGFR pathways of PDGFRαα, PDGFRαβ, and PDGFRββ.

Signaling through PDGFRs plays an important role in PAH, and the PDGF pathway is activated in PAH. FIG. 1 illustrates the PDGFR pathways of PDGFRαα, PDGFRαβ, and PDGFRββ, and shows that the PDGFRβ receptor can activate the AKT, ERK, or STAT3 pathways to promote calcium influx and angiogenesis. The PDGFRα homodimer activates the PLCγ and PI3K pathways and only stimulates calcium influx. The PDGFRαβ heterodimer activates the ERK and STAT3 pathways, stimulating NFκβ and interleukin-6 (IL-6) activity. PDGF signaling also increases transcription factors, including E2F4, Jun, ESR1, EST1, ETS1, SMAD1, SP1, STAT1, MYC, HIFA, LEF1, CEBPB, and FOS. Abbreviations: A, PDGFA; B, PDGFB; αα, PDGFRα homodimer; αβ, PDGFRαβ heterodimer; ββ, PDGFRβ homodimer; PLCγ, phospholipase C gamma; PI3K, phosphoinositide 3 kinase; ERK, extracellular related kinase (also known as p38 MAP kinase); AKT, protein kinase B; STAT3, signal transduction and activator of transcription 3.

Imatinib is a potent PDGF inhibitor, and is less potent against the PDGFRβ isoform than the PDGFRα isoform. Imatinib decreases right ventricular systolic pressure (RVSP) by inhibiting PDGF, and improves survival in the rat monocrotaline model of PAH. Imatinib also improves cardiopulmonary hemodynamics in patients with advanced PAH. However, oral administration of imatinib is associated with significant side effects, and is not used for the treatment and prophylaxis of advanced PAH.

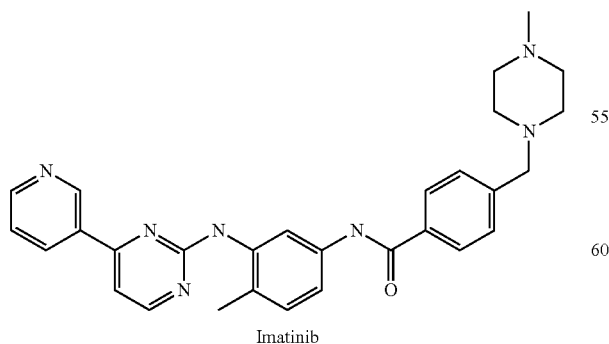

Imatinib

The pulmonary vascular bed is a source of and target for vasoactive factors. Among the most important vasoactive factors for pulmonary vascular homeostasis are factors that utilize cyclic guanosine monophosphate (cGMP) as an intracellular second messenger, including nitric oxide (NO) and the natriuretic peptide family (e.g., atrial, brain, and C-type natriuretic peptides). PDEV is present in the arterial wall smooth muscle within the lungs. PDEV inhibitors block the degradative action of cGMP-specific PDEV on cyclic GMP in the smooth muscle cells lining blood vessels. Examples of PDEV inhibitors include sildenafil (Viagra®), tadalafil (Cialis®), and vardenafil (Levitra®).

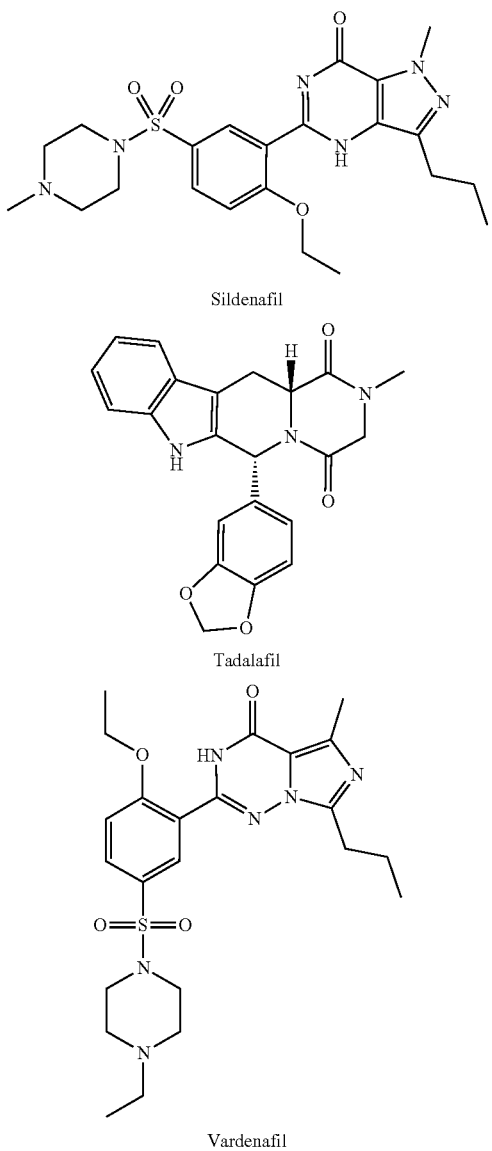

Sildenafil

Tadalafil

Vardenafil

Soluble guanylate cyclase (sGC) is an enzyme in the NO signaling pathway. When NO binds to the prosthetic haem group of sGC, sGC catalyzes the synthesis of cGMP, which promotes vasodilation and inhibits smooth muscle proliferation, leukocyte recruitment, platelet aggregation, and vascular remodeling. sGC stimulators directly stimulate sGC, and increase cGMP production. Non-limiting examples of sGC stimulators include YC-1, BAY 41-2272, BAY 41-8543, riociguat (Adempas®; BAY 63-2521), CFM-1571, BAY 60-4552, vericiguat (BAY 1021189), and A-350619.

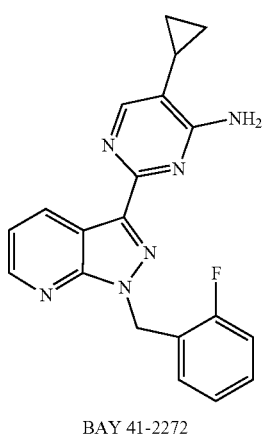

BAY 41-2272

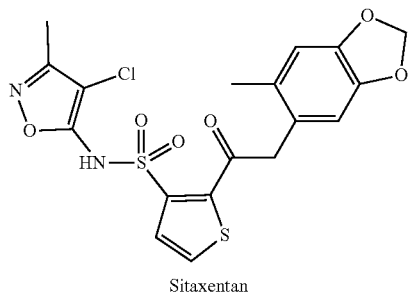

Sitaxentan

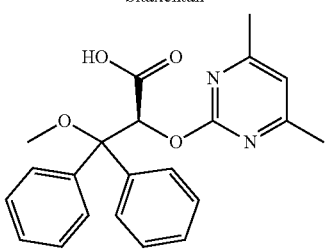

Ambrisentan

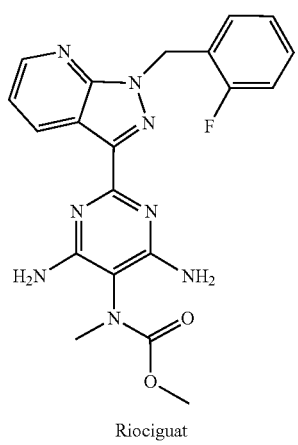

Riociguat

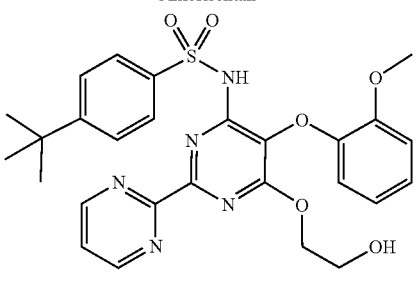

Bosentan

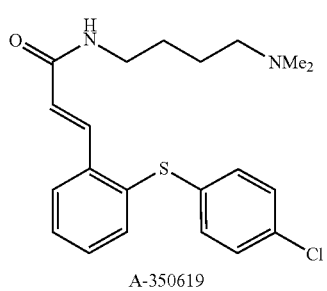

A-350619

The disclosure describes the clinical effects of adding an inhaled PDGFR inhibitor to a regimen of a PDEV inhibitor, an ET receptor antagonist, and/or a sGC.

Compounds of the Invention.

The disclosed invention describes therapeutic formulations of protein kinase inhibitors and methods for treating pulmonary and vascular conditions. The compounds of the invention can modulate the phosphorylation of one or more downstream targets of PDGFRα or PDGFRβ, where the downstream target is any substrate that is phosphorylated as a result of PDGFRα or PDGFRβ activation. In some embodiments, the downstream target of PDGFRα or PDGFRβ is AKT, PDGFR, STAT5, ERK1, or ERK2.

In some embodiments, non-limiting examples of the compounds herein include compounds of the following formula:

ET receptor antagonists are drugs that block ET receptors. The three classes of ET receptor antagonists are: 1) selective $ET_A$ receptor antagonists, which affect only ET A receptors; 2) dual antagonists, which affect ET A and ET B receptors; and 3) selective $ET_B$ receptor antagonists, which affect only ET B receptors. Examples of selective $ET_A$ receptor antagonist include sitaxentan, ambrisentan, atrasentan, BQ-123, and zibotentan. Examples of dual antagonists include bosentan (Tracleer®), macitentan (Opsumit®), and tezosentan. Examples of selective $ET_B$ receptor antagonists include BQ-788 and A192621.

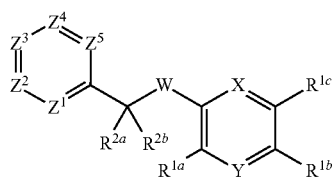

or a pharmaceutically-acceptable salt thereof, wherein:
W is $NR^1$, O, S, or a bond;
each X and Y is independently $CR^2$ or N;
each $R^{1a}$, $R^{1b}$, and $R^{1c}$ is independently H, halogen, hydroxyl, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, heterocyclyl, or heteroaryl, any of which is substituted or unsubstituted;

each $R^{2a}$ and $R^{2b}$ is independently H, halogen, alkyl, alkenyl, alkynyl, aryl, heterocyclyl, or heteroaryl, any of which is substituted or unsubstituted, or together form a carbonyl;

each $Z^1$, $Z^2$, $Z^3$, $Z^4$, and $Z^5$ is independently $CR^2$ or N; and each $R^1$ and $R^2$ is independently H, halogen, hydroxyl, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, heterocyclyl, heteroaryl, sulfhydryl, nitro, nitroso, cyano, azido, a sulfoxide group, a sulfone group, a sulfonamide group, a sulfonic acid group, an imine group, an acyl group, an acyloxy group, any of which is substituted or unsubstituted.

In some embodiments, W is $NR^1$, wherein $R^1$ is H or alkyl. In some embodiments, W is $NR^1$, wherein $R^1$ is H. In some embodiments, each $R^{2a}$ and $R^{2b}$ is independently H or alkyl. In some embodiments, each $R^{2a}$ and $R^{2b}$ is independently H or methyl. In some embodiments, each $R^{2a}$ and $R^{2b}$ is independently H and ethyl.

In some embodiments, each X and Y is independently $CR^2$, wherein $R^2$ is H, halogen, hydroxyl, or alkyl. In some embodiments, each X and Y is independently N. In some embodiments, X is $CR^2$, wherein $R^2$ is H, and Y is N. In some embodiments, X is N, and Y is $CR^2$, wherein $R^2$ is H.

In some embodiments, each $R^{1a}$, $R^{1b}$, and $R^{1c}$ is independently H, halogen, hydroxyl, alkyl, aryl, or heteroaryl, any of which is substituted or unsubstituted. In some embodiments, each $R^{1a}$, $R^{1b}$, and $R^{1c}$ is independently H, aryl, or heteroaryl, any of which is substituted or unsubstituted. In some embodiments, each $R^{1a}$, $R^{1b}$, and $R^{1c}$ is independently H or aryl, any of which is substituted or unsubstituted. In some embodiments, each $R^{1a}$, $R^{1b}$, and $R^{1c}$ is independently H or substituted aryl.

In some embodiments, each $R^{1a}$ and $R^{1b}$ is H, and $R^{1c}$ is substituted aryl. In some embodiments, each $R^{1a}$ and $R^{1b}$ is H, and $R^{1c}$ is substituted phenyl. In some embodiments, each $R^{1a}$ and $R^{1b}$ is H, and $R^{1c}$ is phenyl substituted with hydroxyl, alkyl, or alkoxy. In some embodiments, each $R^{1a}$ and $R^{1b}$ is H, and $R^{1c}$ is phenyl substituted with hydroxyl or alkoxy. In some embodiments, each $R^{1a}$ and $R^{1b}$ is H, and $R^{1c}$ is phenyl substituted with hydroxyl and alkoxy. In some embodiments, each $R^{1a}$ and $R^{1b}$ is H, and $R^{1c}$ is phenyl substituted with alkoxy. In some embodiments, each $R^{1a}$ and $R^{1b}$ is H, and $R^{1c}$ is phenyl substituted with methoxy. In some embodiments, each $R^{1a}$ and $R^{1b}$ is H, and $R^{1c}$ is phenyl substituted with two methoxy groups. In some embodiments, each $R^{1a}$ and $R^{1b}$ is H, and $R^{1c}$ is 3,4-dimethoxyphenyl. In some embodiments, each $R^{1a}$ and $R^{1b}$ is H, and $R^{1c}$ is 3-hydroxy-4-methoxyphenyl.

In some embodiments, each $Z^1$, $Z^2$, $Z^3$, $Z^4$, and $Z^5$ is independently $CR^2$, wherein $R^2$ is H, halogen, hydroxyl, alkyl, an ether group, an amine group, or an amide group. In some embodiments, each $Z^1$, $Z^2$, $Z^3$, $Z^4$, and $Z^5$ is independently $CR^2$, wherein $R^2$ is H or an amide group. In some embodiments, each $Z^1$, $Z^3$, $Z^4$, and $Z^5$ is independently $CR^2$, wherein $R^2$ is H; and $Z^2$ is $CR^2$, wherein $R^2$ is an amide group. In some embodiments, each $Z^1$, $Z^3$, $Z^4$, and $Z^5$ is independently $CR^2$, wherein $R^2$ is H; and $Z^2$ is $CR^2$, wherein $R^2$ is $NHC(O)R^3$, wherein $R^3$ is H, hydroxyl, alkyl, alkenyl, aryl, heterocyclyl, or heteroaryl, any of which is substituted or unsubstituted. In some embodiments, each $Z^1$, $Z^3$, $Z^4$, and $Z^5$ is independently $CR^2$, wherein $R^2$ is H; and $Z^2$ is $CR^2$, wherein $R^2$ is $NHC(O)R^3$, wherein $R^3$ is aryl or heteroaryl, any of which is substituted or unsubstituted. In some embodiments, each $Z^1$, $Z^3$, $Z^4$, and $Z^5$ is independently $CR^2$, wherein $R^2$ is H; and $Z^2$ is $CR^2$, wherein $R^2$ is $NHC(O)R^3$, wherein $R^3$ is substituted heteroaryl. In some embodiments, each $Z^1$, $Z^3$, $Z^4$, and $Z^5$ is independently $CR^2$, wherein $R^2$ is H; and $Z^2$ is $CR^2$, wherein $R^2$ is $NHC(O)R^3$, wherein $R^3$ is substituted pyridinyl. In some embodiments, each $Z^1$, $Z^3$, $Z^4$, and $Z^5$ is independently $CR^2$, wherein $R^2$ is H; and $Z^2$ is $CR^2$, wherein $R^2$ is $NHC(O)R^3$, wherein $R^3$ is methylpyridinyl. In some embodiments, $Z^1$, $Z^3$, $Z^4$, and $Z^5$ is independently $CR^2$, wherein $R^2$ is H; and $Z^2$ is $CR^2$, wherein $R^2$ is $NHC(O)R^3$, wherein $R^3$ is 2-methylpyridin-5-yl.

In some embodiments, W is $NR^1$, wherein $R^1$ is H; each X and Y is independently N; each $R^{1a}$ and $R^{1b}$ is H; $R^{1c}$ is substituted aryl; each $R^{2a}$ and $R^{2b}$ is independently H or alkyl; each $Z^1$, $Z^3$, $Z^4$, and $Z^5$ is independently $CR^2$, wherein $R^2$ is H; $Z^2$ is $CR^2$, wherein $R^2$ is $NHC(O)R^3$, wherein $R^3$ is substituted heteroaryl. In some embodiments, W is $NR^1$, wherein $R^1$ is H; each X and Y is independently N; each $R^{1a}$ and $R^{1b}$ is H; $R^{1c}$ is substituted phenyl; each $R^{2a}$ and $R^{2b}$ is independently H or alkyl; each $Z^1$, $Z^3$, $Z^4$, and $Z^5$ is independently $CR^2$, wherein $R^2$ is H; $Z^2$ is $CR^2$, wherein $R^2$ is $NHC(O)R^3$, wherein $R^3$ is pyridinyl. In some embodiments, W is $NR^1$, wherein $R^1$ is H; each X and Y is independently N; each $R^{1a}$ and $R^{1b}$ is H; $R^{1c}$ is phenyl with two alkoxy substituents; each $R^{2a}$ and $R^{2b}$ is independently H or alkyl; each $Z^1$, $Z^3$, $Z^4$, and $Z^5$ is independently $CR^2$, wherein $R^2$ is H; $Z^2$ is $CR^2$, wherein $R^2$ is $NHC(O)R^3$, wherein $R^3$ is methylpyridinyl. In some embodiments, W is $NR^1$, wherein $R^1$ is H; each X and Y is independently N; each $R^{1a}$ and $R^{1b}$ is H; $R^{1c}$ is phenyl substituted with an alkoxy group and a hydroxyl group; each $R^{2a}$ and $R^{2b}$ is independently H or alkyl; each $Z^1$, $Z^3$, $Z^4$, and $Z^5$ is independently $CR^2$, wherein $R^2$ is H; $Z^2$ is $CR^2$, wherein $R^2$ is $NHC(O)R^3$, wherein $R^3$ is methylpyridinyl. In some embodiments, W is $NR^1$, wherein $R^1$ is H; each X and Y is independently N; each $R^{1a}$ and $R^{1b}$ is H; $R^{1c}$ is phenyl substituted with an alkoxy group and a hydroxyl group; each $R^{2a}$ and $R^{2b}$ is independently H or alkyl; each $Z^1$, $Z^3$, $Z^4$, and $Z^5$ is independently $CR^2$, wherein $R^2$ is H; $Z^2$ is $CR^2$, wherein $R^2$ is $NHC(O)R^3$, wherein $R^3$ is 2-methylpyridin-5-yl.

In some embodiments, non-limiting examples of the compounds herein include compounds of the following formula:

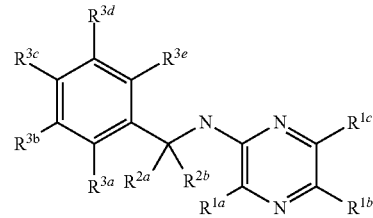

or a pharmaceutically-acceptable salt thereof, wherein:

each $R^{1a}$, $R^{1b}$, and $R^{1c}$ is independently H, halogen, hydroxyl, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, heterocyclyl, or heteroaryl, any of which is substituted or unsubstituted;

each $R^{2a}$ and $R^{2b}$ is independently H, halogen, alkyl, alkenyl, alkynyl, aryl, heterocyclyl, or heteroaryl, any of which is substituted or unsubstituted; and each $R^{3a}$, $R^{3b}$, $R^{3c}$, $R^{3d}$, and $R^{3e}$ is independently H, halogen, hydroxyl, alkyl, alkenyl, alkynyl, an alkoxy group, an ether group, a carboxylic acid group, a carboxaldehyde group, an ester group, an amine group, an amide group, a carbonate group, a carbamate group, a thioether group, a thioester group, a thioacid group, aryl, heterocyclyl, heteroaryl, sulfhydryl, nitro, nitroso, cyano, azido, a sulfoxide group, a sulfone group, a sulfonamide group, a sulfonic acid group, an imine group, an acyl group, or an acyloxy group, any of which is substituted or unsubstituted.

In some embodiments, each $R^{1a}$, $R^{1b}$, and $R^{1c}$ is independently H, halogen, hydroxyl, alkyl, aryl, or heteroaryl, any of which is substituted or unsubstituted. In some embodiments, each $R^{1a}$, $R^{1b}$, and $R^{1c}$ is independently H, aryl, or heteroaryl, any of which is substituted or unsubstituted. In some embodiments, each $R^{1a}$, $R^{1b}$, and $R^{1c}$ is independently H or aryl, wherein the aryl is substituted or unsubstituted. In some embodiments, each $R^{1a}$ and $R^{1b}$ is H, and $R^{1c}$ is aryl, wherein the aryl is substituted or unsubstituted. In some embodiments, each $R^{1a}$ and $R^{1b}$ is H, and $R^{1c}$ is substituted aryl. In some embodiments, each $R^{1a}$ and $R^{1b}$ is H, and $R^{1c}$ is phenyl substituted with halogen, hydroxyl, alkyl, or an alkoxy group. In some embodiments, each $R^{1a}$ and $R^{1b}$ is H, and $R^{1c}$ is phenyl substituted with two alkoxy groups. In some embodiments, each $R^{1a}$ and $R^{1b}$ is H, and $R^{1c}$ is 3,4-dimethoxyphenyl. In some embodiments, each $R^{1a}$ and $R^{1b}$ is H, and $R^{1c}$ is phenyl substituted with an alkoxy group and a hydroxyl group. In some embodiments, each $R^{1a}$ and $R^{1b}$ is H, and $R^{1c}$ is 3-hydroxy-4-methoxyphenyl.

In some embodiments, each $R^{2a}$ and $R^{2b}$ is independently H or alkyl. In some embodiments, each $R^{2a}$ and $R^{2b}$ is independently H or methyl. In some embodiments, each $R^{2a}$ and $R^{2b}$ is independently H or ethyl.

In some embodiments, each $R^{3a}$, $R^{3b}$, $R^{3c}$, $R^{3d}$, and $R^{3e}$ is independently H, halogen, hydroxyl, alkyl, an alkoxy group, an amine group, or an amide group, any of which is substituted or unsubstituted. In some embodiments, each $R^{3a}$, $R^{3b}$, $R^{3c}$, $R^{3d}$, and $R^{3e}$ is independently H, hydroxyl, or an amide group, any of which is substituted or unsubstituted. In some embodiments, each $R^{3a}$, $R^{3c}$, $R^{3d}$, and $R^{3e}$ is independently H, and $R^{3b}$ is an amide group. In some embodiments, each $R^{3a}$, $R^{3c}$, $R^{3d}$, and $R^{3e}$ is independently H; and $R^{3b}$ is NHC(O)$R^3$, wherein $R^3$ is H, hydroxyl, alkyl, alkenyl, aryl, heterocyclyl, or heteroaryl, any of which is substituted or unsubstituted. In some embodiments, each $R^{3a}$, $R^{3c}$, $R^{3d}$, and $R^{3e}$ is independently H; and $R^{3b}$ is NHC(O)$R^3$, wherein $R^3$ is aryl or heteroaryl, any of which is substituted or unsubstituted. In some embodiments, each $R^{3a}$, $R^{3c}$, $R^{3d}$, and $R^{3e}$ is independently H; and $R^{3b}$ is NHC(O)$R^3$, wherein $R^3$ is substituted pyridinyl. In some embodiments, each $R^{3a}$, $R^{3c}$, $R^{3d}$, and $R^{3e}$ is independently H; and $R^{3b}$ is NHC(O)$R^3$, wherein $R^3$ is methylpyridinyl. In some embodiments, each $R^{3a}$, $R^{3c}$, $R^{3d}$, and $R^{3e}$ is independently H; and $R^{3b}$ is NHC(O)$R^3$, wherein $R^3$ is methylpyridin-5-yl.

In some embodiments, each $R^{1a}$ and $R^{1b}$ is independently H; $R^{1c}$ is substituted aryl; each $R^{2a}$ and $R^{2b}$ is independently H or alkyl; each $R^{3a}$, $R^{3c}$, $R^{3d}$, and $R^{3e}$ is independently H; and $R^{3b}$ is an amide group. In some embodiments, each $R^{1a}$ and $R^{1b}$ is independently H; $R^{1c}$ is substituted phenyl; each $R^{2a}$ and $R^{2b}$ is independently H or methyl; each $R^{3a}$, $R^{3c}$, $R^{3d}$, and $R^{3e}$ is independently H; and $R^{3b}$ is NHC(O)$R^3$, wherein $R^3$ is substituted heteroaryl. In some embodiments, each $R^{1a}$ and $R^{1b}$ is independently H; $R^{1c}$ is substituted phenyl; each $R^{2a}$ and $R^{2b}$ is independently H or methyl; each $R^{3a}$, $R^{3c}$, $R^{3d}$, and $R^{3e}$ is independently H; and $R^{3b}$ is NHC(O)$R^3$, wherein $R^3$ is substituted pyridinyl. In some embodiments, each $R^{1a}$ and $R^{1b}$ is independently H; $R^{1c}$ is substituted phenyl; each $R^{2a}$ and $R^{2b}$ is independently H or methyl; each $R^{3a}$, $R^{3c}$, $R^{3d}$, and $R^{3e}$ is independently H; and $R^{3b}$ is NHC(O)$R^3$, wherein $R^3$ is methylpyridinyl. In some embodiments, each $R^{1a}$ and $R^{1b}$ is independently H; $R^{1c}$ is phenyl substituted with two alkoxy groups; each $R^{2a}$ and $R^{2b}$ is independently H or methyl; each $R^{3a}$, $R^{3c}$, $R^{3d}$, and $R^{3e}$ is independently H; and $R^{3b}$ is NHC(O)$R^3$, wherein $R^3$ is substituted pyridinyl. In some embodiments, each $R^{1a}$ and $R^{1b}$ is independently H; $R^{1c}$ is phenyl substituted with one alkoxy group and one hydroxyl group; each $R^{2a}$ and $R^{2b}$ is independently H or methyl; each $R^{3a}$, $R^{3c}$, $R^{3d}$, and $R^{3e}$ is independently H; and $R^{3b}$ is NHC(O)$R^3$, wherein $R^3$ is substituted pyridinyl.

In some embodiments, non-limiting examples of the compounds herein include compounds of the following formula:

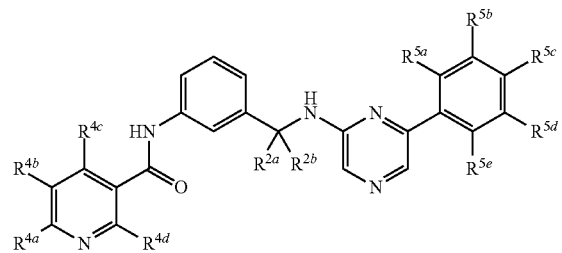

or a pharmaceutically-acceptable salt thereof, wherein:

each $R^{2a}$ and $R^{2b}$ is independently H, halogen, alkyl, alkenyl, alkynyl, aryl, heterocyclyl, or heteroaryl, any of which is substituted or unsubstituted;

each $R^{4a}$, $R^{4b}$, $R^{4c}$, and $R^{4d}$ is independently H, halogen, hydroxyl, alkyl, an alkoxy group, a carboxylic acid group, an ester group, an amine group, an amide group, sulfhydryl, nitro, nitroso, cyano, azido, a sulfoxide group, a sulfone group, a sulfonamide group, a sulfonic acid group, or an acyloxy group, any of which is substituted or unsubstituted; and each $R^{5a}$, $R^{5b}$, $R^{5c}$, $R^{5d}$, and $R^{5e}$ is independently H, halogen, hydroxyl, alkyl, an alkoxy group, a carboxylic acid group, ester group, an amine group, or an amide group, any of which is substituted or unsubstituted.

In some embodiments, each $R^{2a}$ and $R^{2b}$ is independently H or alkyl. In some embodiments, each $R^{2a}$ and $R^{2b}$ is independently H or methyl. In some embodiments, each $R^{2a}$ and $R^{2b}$ is independently H or ethyl. In some embodiments, each $R^{2a}$ and $R^{2b}$ is independently H and ethyl.

In some embodiments, each $R^{4a}$, $R^{4b}$, $R^{4c}$, and $R^{4d}$ is independently H, halogen, hydroxyl, or alkyl. In some embodiments, each $R^{4a}$, $R^{4b}$, $R^{4c}$, and $R^{4d}$ is independently H or alkyl. In some embodiments, each $R^{4a}$, $R^{4c}$, and $R^{4d}$ is independently H; and R$^{4b}$ is alkyl. In some embodiments, each R$^{4a}$, R$^{4c}$, and R$^{4d}$ is independently H; and R$^{4b}$ is methyl.

In some embodiments, each R$^{5a}$, R$^{5b}$, R$^{5c}$, R$^{5d}$, and R$^{5e}$ is independently H, hydroxyl, alkoxy, or an amine group, any of which is substituted or unsubstituted. In some embodiments, each R$^{5a}$, R$^{5b}$, R$^{5c}$, R$^{5d}$, and R$^{5e}$ is independently H, hydroxyl, or alkoxy. In some embodiments, each R$^{5a}$, R$^{5d}$, and R$^{5e}$ is independently H; and each R$^{5b}$ and R$^{5c}$ is independently hydroxyl or alkoxy. In some embodiments, each R$^{5a}$, R$^{5d}$, and R$^{5e}$ is independently H; and each R$^{5b}$ and R$^{5c}$ is independently alkoxy. In some embodiments, each R$^{5a}$, R$^{5d}$, and R$^{5e}$ is independently H; and each R$^{5b}$ and R$^{5c}$ is independently methoxy. In some embodiments, each R$^{5a}$, R$^{5d}$, and R$^{5e}$ is independently H; R$^{5b}$ is alkoxy; and R$^{5c}$ hydroxyl. In some embodiments, each R$^{5a}$, R$^{5d}$, and R$^{5e}$ is independently H; R$^{5b}$ is methoxy; and R$^{5c}$ hydroxyl.

In some embodiments, the compounds herein are of the formula:

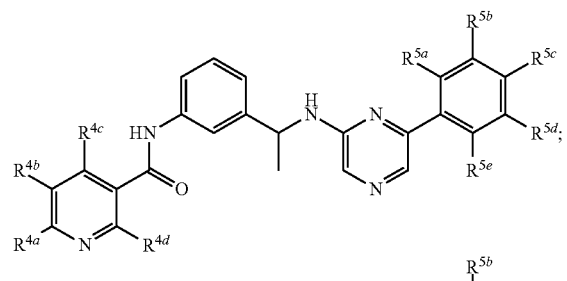

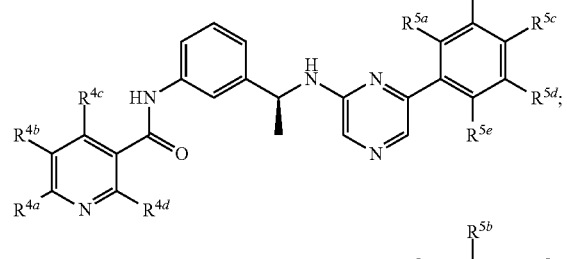

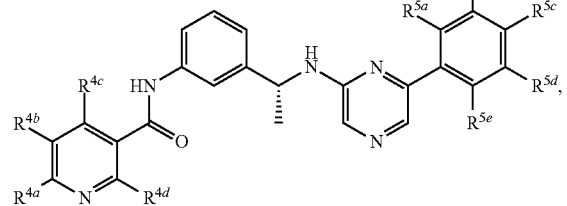

or a pharmaceutically-acceptable salt thereof, with variables defined above.

Non-limiting examples of compounds herein include the following:

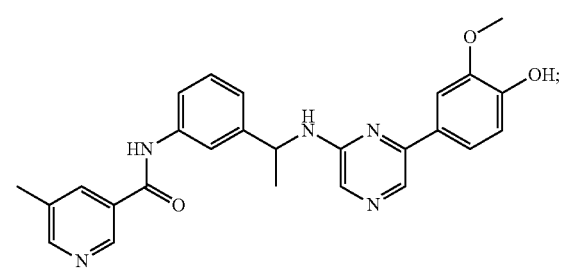

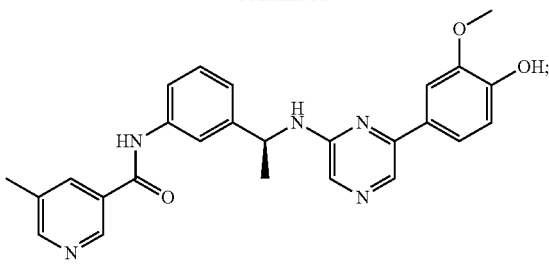

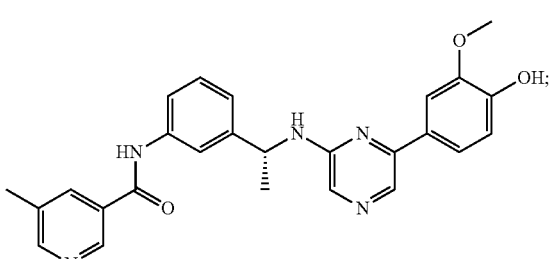

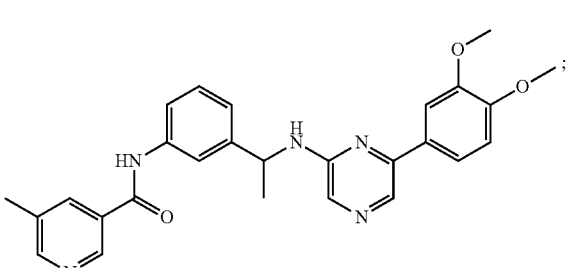

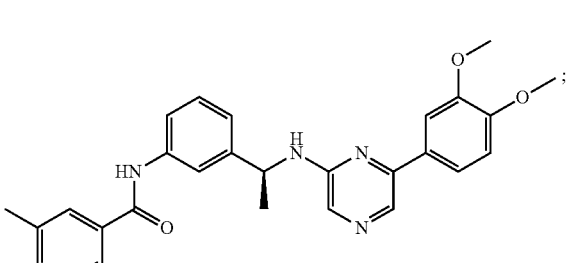

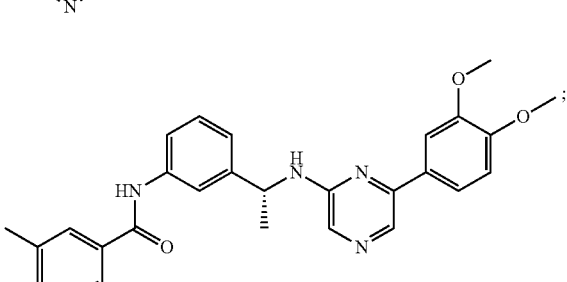

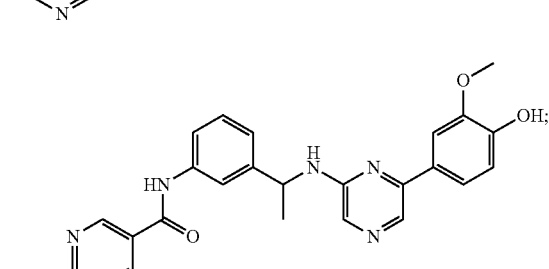

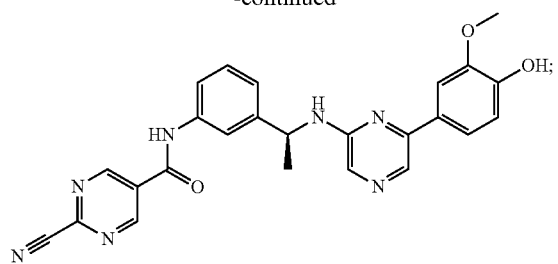
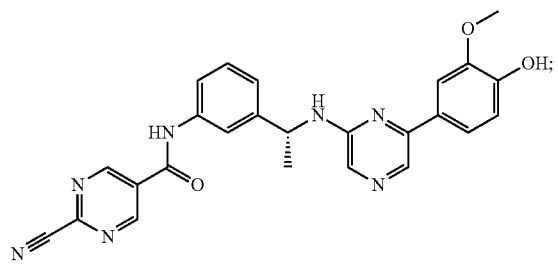
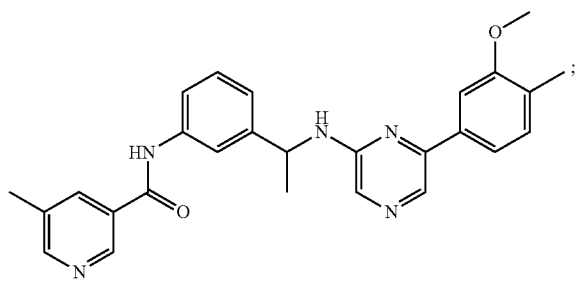
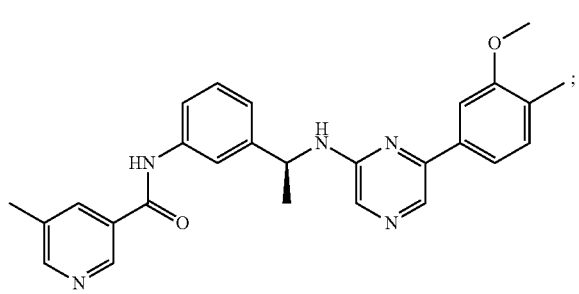
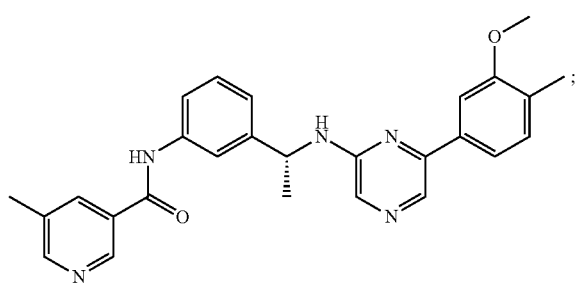
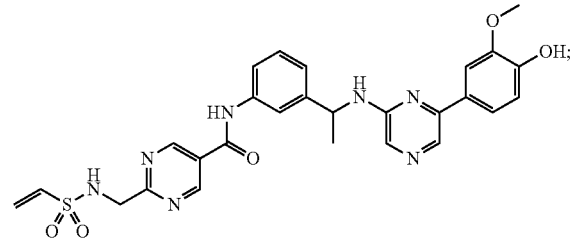
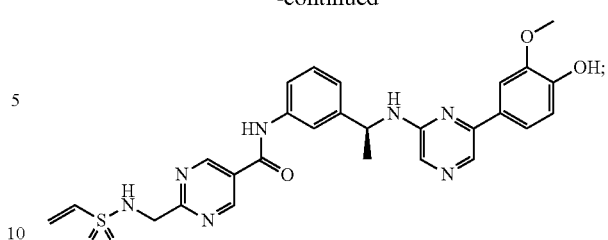
or a pharmaceutically-acceptable salt thereof.
Non-limiting examples of compounds herein include the following:
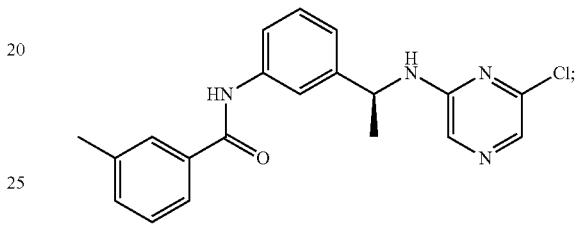
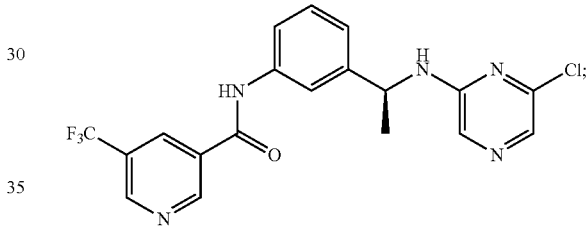
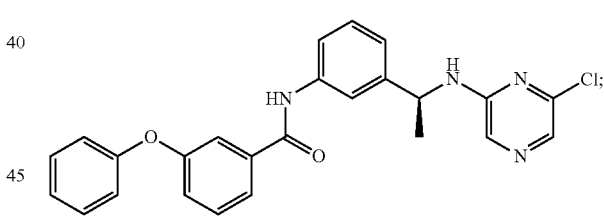
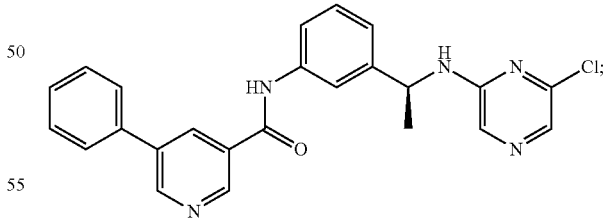
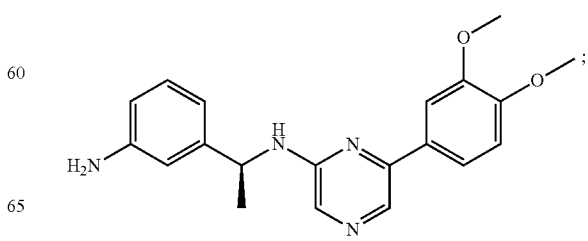

-continued
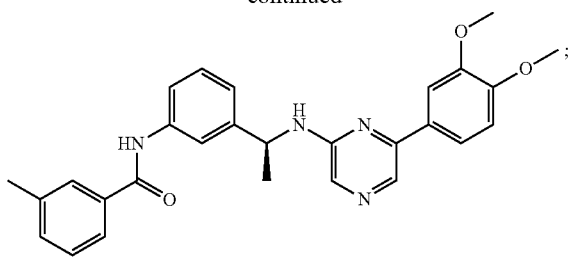
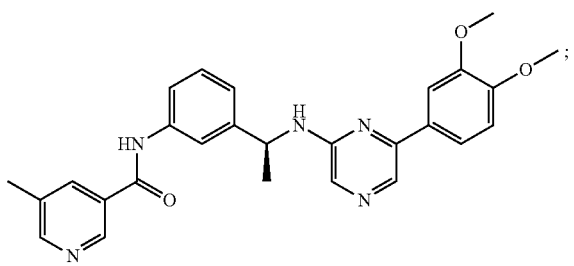
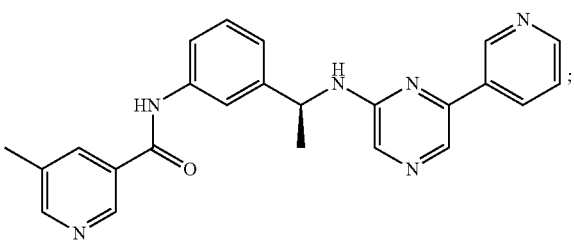
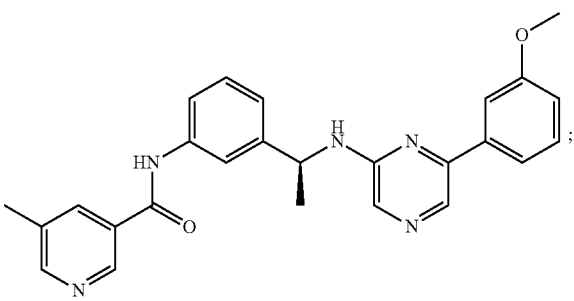
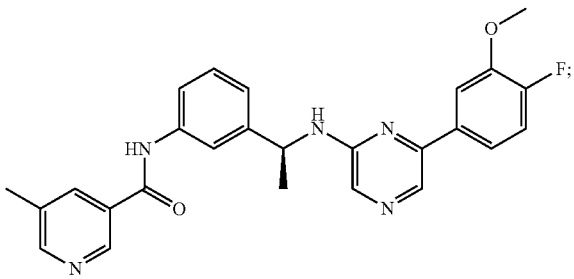
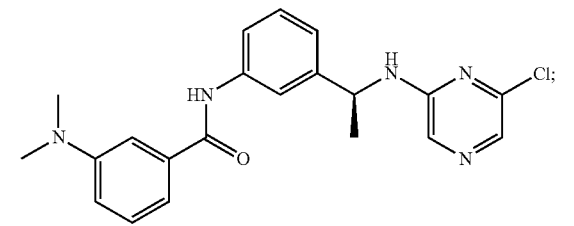
-continued
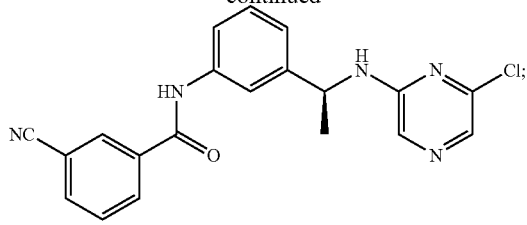
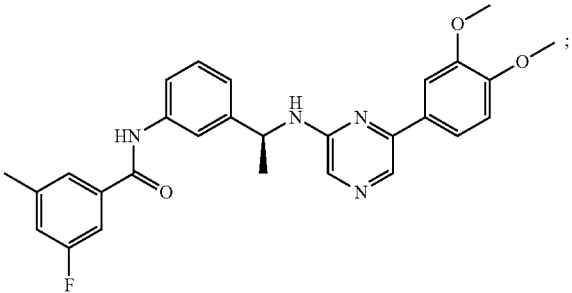
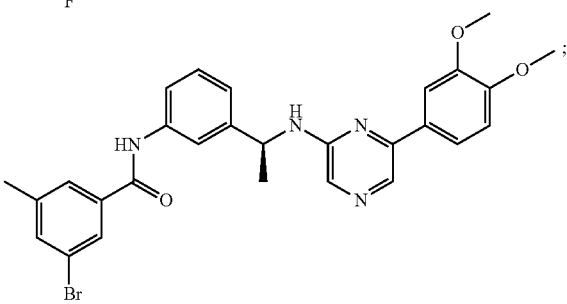
or a pharmaceutically-acceptable salt thereof.
Non-limiting examples of compounds herein include the following:
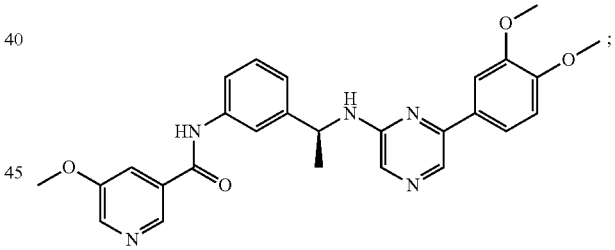
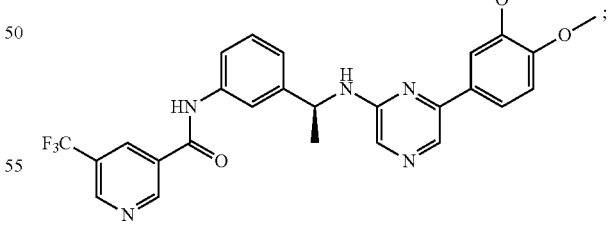
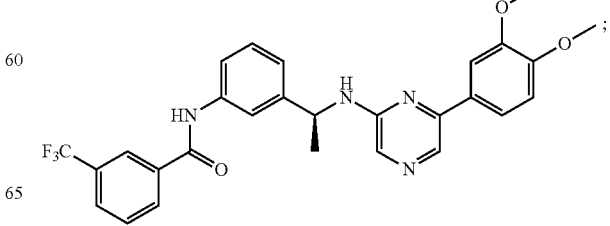

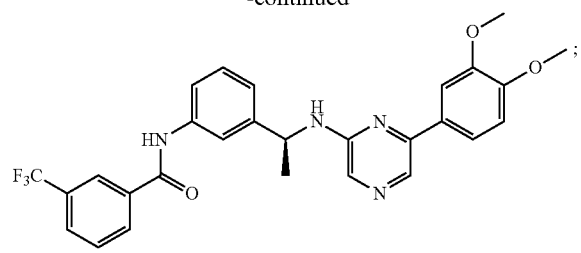
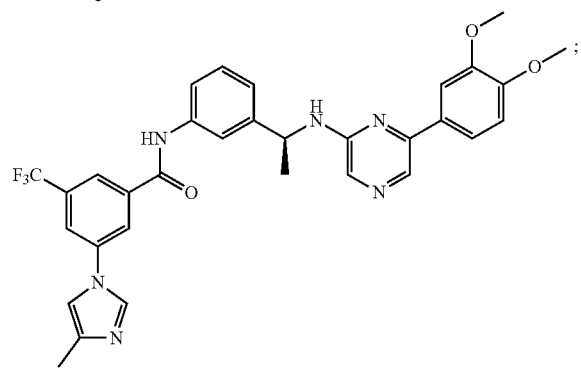
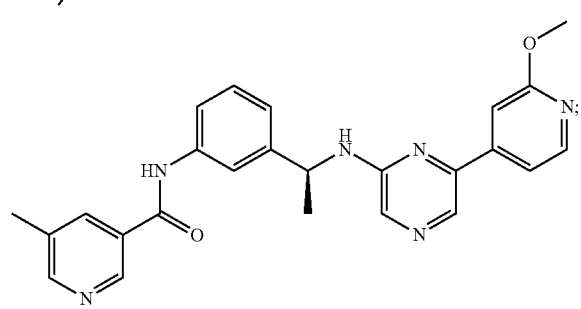
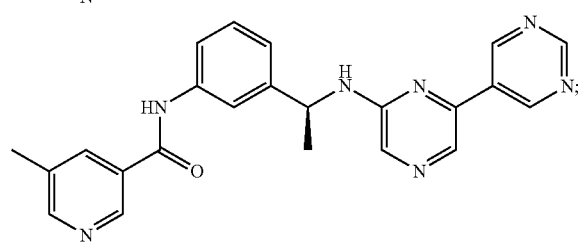
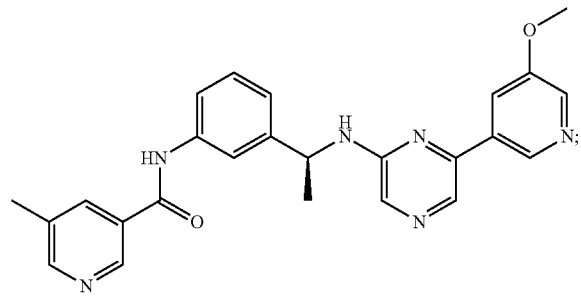
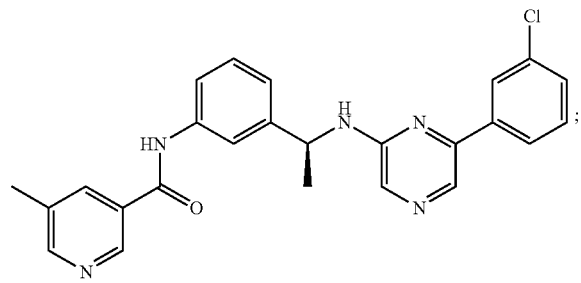
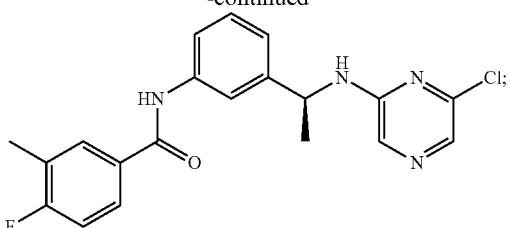
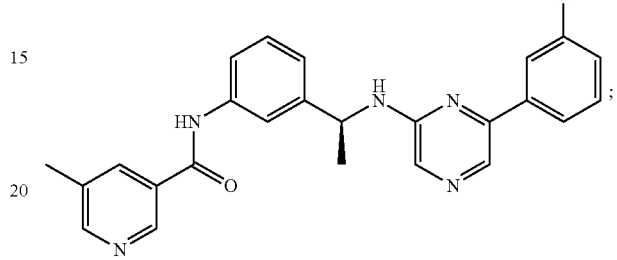
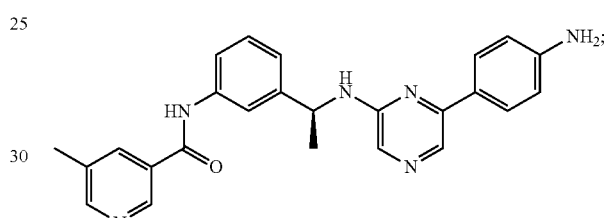
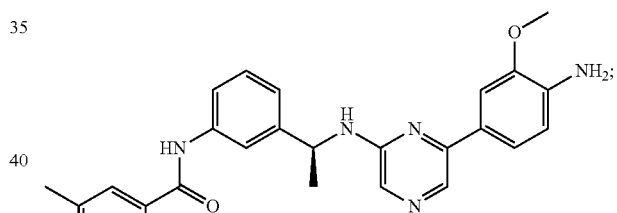
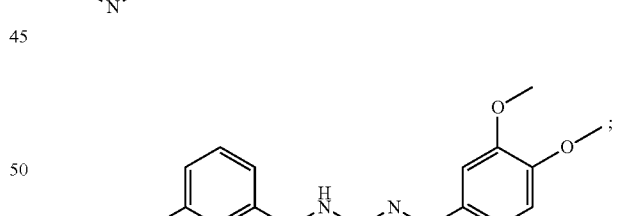
or a pharmaceutically-acceptable salt thereof.
Any compound herein can be any or all stereoisomers, enantiomers, diastereomers, mixtures, racemates, atropisomers, and tautomers thereof.
An illustrative example of a kinase inhibitor is Compound 1, which is a compound of the formula below or a pharmaceutically-acceptable salt thereof.

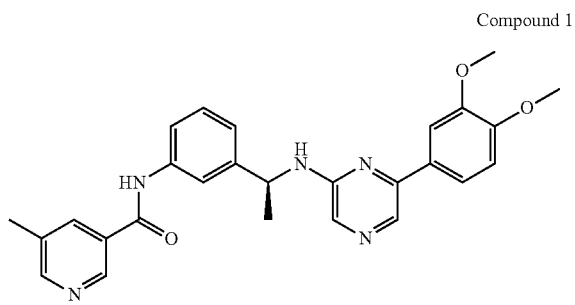

Compound 1

Optional Substituents for Chemical Groups.

Non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, urethane groups, and ester groups.

Non-limiting examples of alkyl and alkylene groups include straight, branched, and cyclic alkyl and alkylene groups. An alkyl or alkylene group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl.

Non-limiting examples of cyclic alkyl groups include cyclopropyl, cyclobutyl, cyclopentyl, cyclohexyl, cycloheptlyl, and cyclooctyl groups. Cyclic alkyl groups also include fused-, bridged-, and spiro-bicycles and higher fused-, bridged-, and spiro-systems. A cyclic alkyl group can be substituted with any number of straight, branched, or cyclic alkyl groups.

Non-limiting examples of alkenyl and alkenylene groups include straight, branched, and cyclic alkenyl groups. The olefin or olefins of an alkenyl group can be, for example, E, Z, cis, trans, terminal, or exo-methylene. An alkenyl or alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of alkynyl or alkynylene groups include straight, branched, and cyclic alkynyl groups. The triple bond of an alkylnyl or alkynylene group can be internal or terminal. An alkylnyl or alkynylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

A halo-alkyl group can be any alkyl group substituted with any number of halogen atoms, for example, fluorine, chlorine, bromine, and iodine atoms. A halo-alkenyl group can be any alkenyl group substituted with any number of halogen atoms. A halo-alkynyl group can be any alkynyl group substituted with any number of halogen atoms.

An alkoxy group can be, for example, an oxygen atom substituted with any alkyl, alkenyl, or alkynyl group. An ether or an ether group comprises an alkoxy group. Non-limiting examples of alkoxy groups include methoxy, ethoxy, propoxy, isopropoxy, and isobutoxy.

An aryl group can be heterocyclic or non-heterocyclic. An aryl group can be monocyclic or polycyclic. An aryl group can be substituted with any number of substituents described herein, for example, hydrocarbyl groups, alkyl groups, alkoxy groups, and halogen atoms. Non-limiting examples of aryl groups include phenyl, toluyl, naphthyl, pyrrolyl, pyridyl, imidazolyl, thiophenyl, and furyl.

An aryloxy group can be, for example, an oxygen atom substituted with any aryl group, such as phenoxy.

An aralkyl group can be, for example, any alkyl group substituted with any aryl group, such as benzyl.

An arylalkoxy group can be, for example, an oxygen atom substituted with any aralkyl group, such as benzyloxy.

A heterocycle can be any ring containing a ring atom that is not carbon, for example, N, O, S, P, Si, B, or any other heteroatom. A heterocycle can be substituted with any number of substituents, for example, alkyl groups and halogen atoms. A heterocycle can be aromatic (heteroaryl) or non-aromatic. Non-limiting examples of heterocycles include pyrrole, pyrrolidine, pyridine, piperidine, succinamide, maleimide, morpholine, imidazole, thiophene, furan, tetrahydrofuran, pyran, and tetrahydropyran.

An acyl group can be, for example, a carbonyl group substituted with hydrocarbyl, alkyl, hydrocarbyloxy, alkoxy, aryl, aryloxy, aralkyl, arylalkoxy, or a heterocycle. Non-limiting examples of acyl include acetyl, benzoyl, benzyloxycarbonyl, phenoxycarbonyl, methoxycarbonyl, and ethoxycarbonyl.

An acyloxy group can be an oxygen atom substituted with an acyl group. An ester or an ester group comprises an acyloxy group. A non-limiting example of an acyloxy group, or an ester group, is acetate.

A carbamate group can be an oxygen atom substituted with a carbamoyl group, wherein the nitrogen atom of the carbamoyl group is unsubstituted, monosubstituted, or disubstituted with one or more of hydrocarbyl, alkyl, aryl, heterocyclyl, or aralkyl. When the nitrogen atom is disubstituted, the two substituents together with the nitrogen atom can form a heterocycle.

The disclosure describes therapeutic formulations comprising a protein kinase inhibitor and at least one additional agent to treat pulmonary and vascular conditions. In some embodiments, the formulation comprises Compound 1 and one additional agent. In some embodiments, the formulation comprises Compound 1 and a PDEV inhibitor. In some embodiments, the formulation comprises Compound 1 and tadalafil. In some embodiments, the formulation comprises Compound 1 and sildenafil. In some embodiments, the formulation comprises Compound 1 and an ET receptor antagonist. In some embodiments, the formulation comprises Compound 1 and a selective $ET_A$ receptor antagonist, dual antagonist, or a selective $ET_B$ receptor antagonist. In some embodiments, the formulation comprises Compound 1 and a selective $ET_A$ receptor antagonist. In some embodiments, the formulation comprises Compound 1 and sitaxentan, ambrisentan, atrasentan, BQ-123, or zibotentan. In some embodiments, the formulation comprises Compound 1 and sitaxentan. In some embodiments, the formulation comprises Compound 1 and ambrisentan. In some embodiments, the formulation comprises Compound 1 and a dual antagonist. In some embodiments, the formulation comprises Compound 1 and macitentan. In some embodiments, the formulation comprises Compound 1 and an sGC stimulator. In some embodiments, the formulation comprises Compound 1 and riociguat. In some embodiments, the formulation comprises Compound 1 and vericiguat.

In some embodiments, the formulation comprises Compound 1 and two additional agents. In some embodiments, the formulation comprises Compound 1, a PDEV inhibitor, and an ET receptor antagonist. In some embodiments, the formulation comprises Compound 1, tadalafil, and ambrisentan. In some embodiments, the formulation comprises Compound 1, a PDEV inhibitor, and a sGC stimulator. In some embodiments, the formulation comprises Compound 1, tadalafil, and riociguat. In some embodiments, the formulation comprises Compound 1, and ET receptor antagonist, and a sGC stimulator. In some embodiments, the formulation comprises Compound 1, ambrisentan, and riociguat.

In some embodiments, the formulation comprises Compound 1 and three additional agents. In some embodiments, the formulation comprises Compound 1, a PDEV inhibitor, an ET receptor antagonist, and a sGC stimulator. In some embodiments, the formulation comprises Compound 1, tadalafil, ambrisentan, and riociguat.

Pharmaceutically-Acceptable Salts.

The disclosure provides the use of pharmaceutically-acceptable salts of any therapeutic compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Salts derived from appropriate bases include alkali metal (e.g., sodium), alkaline earth metal, ammonium and N-(alkyl)$_4^+$ salts. Metal salts can arise from the addition of an inorganic base to a compound of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc. In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine. In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt.

Acid addition salts can arise from the addition of an acid to a compound of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid. In some embodiments, the acid salt is an acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate or an undecanoate.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

Base addition salts can arise from the addition of a base to a compound of the invention. In some embodiments, the base is sodium hydroxide, potassium hydroxide, lye, calcium hydroxide, or magnesium hydroxide. In some embodiments, the base is an alkali metasilicate, alkali metal hydroxide, sodium carbonate, sodium bicarbonate, sodium percarbonate, sodium persilicate, or potassium metabisulfite.

Purity of Compounds of the Invention.

Any compound herein can be purified. A compound herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

Pharmaceutical Compositions of the Invention.

A pharmaceutical composition of the invention can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, parenteral, ophthalmic, subcutaneous, transdermal, nasal, vaginal, and topical administration.

A pharmaceutical composition can be administered in a local manner, for example, via injection of the compound directly into an organ, optionally in a depot or sustained release formulation or implant. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated by combining the active compounds with pharmaceutically-acceptable carriers or excipients. Such carriers can be used to formulate liquids, gels, syrups, elixirs, slurries, or suspensions, for oral ingestion by a subject. Non-limiting examples of solvents used in an oral dissolvable formulation can include water, ethanol, isopropanol, saline, physiological saline, DMSO, dimethylformamide, potassium phosphate buffer, phosphate buffer saline (PBS), sodium phosphate buffer, 4-2-hydroxyethyl-1-piperazineethanesulfonic acid buffer (HEPES), 3-(N-morpholino)propanesulfonic acid buffer (MOPS), piperazine-N, N'-bis(2-ethanesulfonic acid) buffer (PIPES), and saline sodium citrate buffer (SSC). Non-limiting examples of co-solvents used in an oral dissolvable formulation can include sucrose, urea, cremaphor, DMSO, and potassium phosphate buffer.

Pharmaceutical preparations can be formulated for intravenous administration. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

The compounds can be formulated for inhalation of the composition. In some embodiments, the compounds are administered through intranasal administration. In some embodiments, the compounds are administered as a solution, suspension, or a dry powder.

The compounds can be administered directly to the respiratory track as an aerosol. In some embodiments, the compounds are packaged in a pressurized aerosol container with suitable propellants and adjuvants. In some embodiments, the propellants are hydrocarbon propellants, such as propane, butane, or isobutene. In some embodiments, aerosol formulations can include other ingredients, such as co-solvents, stabilizers, surfactants, antioxidants, lubricants, and pH adjusters. The aerosol formulations can be administered using a metered dose inhaler.

The compounds can be administered in the form of a lung surfactant formulation. In some embodiments, the lung surfactant formulation is Infrasurf®, Survanta®, Curosurf®, or synthetic pulmonary surfactant formulations, such as Exosurf® and artificial lung expanding compounds (ALECs). In some embodiments, the surfactant formulations are administered via airway instillation (i.e., after intubation) or intratracheally.

The compounds can be administered as an inhalable powder. In some embodiments, the compounds can be administered as an inhalable dry powder. In some embodiments, the powder formulation can include pharmaceutically acceptable excipients, such as monosaccharides (e.g., glucose, arabinose), disaccharides (e.g., lactose, saccharose, maltose), oligosaccharides or polysaccharides (e.g., dextrane), polyalcohols (e.g., sorbitol, mannitol, xylitol), salts (e.g., sodium chloride, calcium carbonate), or any combination thereof. In some embodiments, the compounds are administered in a non-pressurized form using a nebulizer or an atomizer.

In some embodiments, Compound 1 is administered by inhalation. In some embodiments, Compound 1 and additional agents are administered by inhalation. In some embodiments, Compound 1 is administered by inhalation, and additional agents are administered by gavage.

Delivery of compound 1 as an inhaled dry powder results in delivery locally to the lung, resulting in lower systemic drug exposure and fewer side effects. In some embodiments, lower systemic drug exposure can lower the risk of bleeding, gastrointestinal side effects, liver toxicity, fluid retention or edema, neutropenia or leukopenia, anemia, or infection. In some embodiments, lower systemic drug exposure can lower the risk of gastrointestinal side effects, such as nausea, vomiting, or diarrhea.

In some embodiments, the inhaled dry powder formulation can contain about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% of Compound 1 by weight. In some embodiments, the inhaled dry powder formulation can contain about 40%, about 50%, or about 60% of Compound 1 by weight. In some embodiments, the inhaled dry powder formulation can contain about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% of leucine by weight. In some embodiments, the inhaled dry powder formulation can contain about 40%, about 50%, or about 60% of leucine by weight. In some embodiments, the inhaled dry powder formulation can contain about 50% of Compound 1 and about 50% of leucine by weight.

In some embodiments, the inhaled dry powder formulation can contain about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% of a lipid-based surfactant. In some embodiments, the inhaled dry powder formulation can contain 1,2-distearoyl-sn-glycero-3-phosphocholine (DSPC), dipalmitoylphosphatidylcholine (DPPC), 1,2-dimyristoyl-sn-glycero-3-phosphorylcholine (DMPC), or liposomes.

A spray dried powder formulation of Compound 1 and leucine can have particle sizes suitable for inhalation. In some embodiments, the mass median aerodynamic diameter (MMAD) of the particles as measured by cascade impaction with a Next Generation Impactor (NGI) can be in the range of 1.9-3.8 microns with a geometric standard deviation (GSD) 1.5-3.5. In some embodiments, MMAD is about 1 micron, about 1.5 microns, about 2 microns, about 2.5 microns, about 3 microns, about 3.5 microns, about 4 microns, about 4.5 microns, about 5 microns, about 5.5 microns, about 6 microns, about 6.5 microns, about 7 microns, about 7.5 microns, about 8 microns, about 8.5 microns, about 9 microns, about 9.5 microns, about 10 microns, about 11 microns, about 12 microns, about 13 microns, about 14 microns, about 15 microns, about 16 microns, about 17 microns, about 18 microns, about 19 microns, or about 20 microns. In some embodiments, the MMAD is about 1 micron. In some embodiments, the MMAD is about 2 microns to about 2.5 microns. In some embodiments, the MMAD is about 2 microns, In some embodiments, the MMAD is about 2.5 microns. In some embodiments, the MMAD is less than about 5 microns.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a compound described herein can be manufactured, for example, by mixing, dissolving, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers and preservatives.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the invention include liquid, powder, gel, nanosuspension, nanoparticle, microgel, aqueous or oily suspensions, emulsion, and any combination thereof.

Non-limiting examples of pharmaceutically-acceptable excipients suitable for use in the invention include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

In some embodiments, a formulation comprises a hydrophobic amino acid selected from the group consisting of tryptophan, tyrosine, leucine, trileucine, isoleucine, and phenylalanine. In some embodiments, the formulation comprises about 10%, about 20%, about 30%, about 40%, about 50%, about 60%, about 70%, about 80%, or about 90% of a hydrophobic amino acid by weight of the composition. In some embodiments, the formulations of the invention comprise leucine. In some embodiments, the formulation comprises about 30%, about 40%, about 50%, about 60%, about 70% of leucine by weight of the composition. In some embodiments, the formulation comprises about 50% of leucine by weight of the composition. In some embodiments, the formulations of the invention comprise trileucine. In some embodiments, the formulation comprises about 30%, about 35%, about 40%, about 45%, about 50%, about 55%, about 60%, about 65%, or about 70% of trileucine by weight of the composition. In some embodiments, the formulation comprises about 50% of trileucine by weight of the composition.

In some embodiments, a formulation comprises a lipid product, for example, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% of a lipid by weight of the composition. In some embodiments, the formulation comprises DSPC, DPPC, DMPC, or liposomes. In some embodiments, the formulation comprises about 30%, about 35%, about 40%, about 45%, about 50%, about 55%, about 60%, about 65%, or about 70% of DSPC by weight of the composition. In some embodiments, the formulation comprises about 30%, about 35%, about 40%, about 45%, about 50%, about 55%, about 60%, about 65%, or about 70% of DPPC by weight of the composition. In some embodiments, the formulation comprises about 30%, about 35%, about 40%, about 45%, about 50%, about 55%, about 60%, about 65%, or about 70% of DMPC by weight of the composition.

A composition of the invention can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

Methods of Administration.

Multiple therapeutic agents can be administered in any order or simultaneously. In some embodiments, a compound of the invention is administered in combination with, before, or after additional therapeutic agents. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneous, the timing between the multiple doses can vary to as much as about a month.

In some embodiments, Compound 1 is administered before a second agent. In some embodiments, Compound 1 is administered before administration of a PDEV inhibitor or an ET receptor antagonist. In some embodiments, Compound 1 is administered before administration of a PDEV inhibitor and an ET receptor antagonist. In some embodiments, Compound 1 is administered after administration of a first agent. In some embodiments, Compound 1 is administered after administration of a PDEV inhibitor or ET receptor antagonist. In some embodiments, Compound 1 is administered after administration of a PDEV inhibitor and an ET receptor antagonist.

Therapeutic agents described herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The administration of the therapeutic agents can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein. A therapeutic agent can be administered as soon as is practicable after the onset of a disease or condition is detected or suspected, and for a length of time necessary for the treatment of the disease, such as, for example, from about 1 month to about 3 months. The length of treatment can vary for each subject.

Pharmaceutical compositions provided herein, can be administered in conjunction with other therapies, for example, chemotherapy, radiation, surgery, anti-inflammatory agents, and selected vitamins. The other agents can be administered prior to, after, or concomitantly with the pharmaceutical compositions.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Non-limiting examples of pharmaceutically active agents suitable for combination with compositions of the disclosure include anti-infectives, i.e., aminoglycosides, antiviral agents, antimicrobials, anticholinergics/antispasmotics, antidiabetic agents, antihypertensive agents, antineoplastics, cardiovascular agents, central nervous system agents, coagulation modifiers, hormones, immunologic agents, immunosuppressive agents, and ophthalmic preparations.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, plant cellulosic material and spheronization agents, and any combination thereof.

Compounds can be delivered via liposomal technology. The use of liposomes as drug carriers can increase the therapeutic index of the compounds. Liposomes are composed of natural phospholipids, and can contain mixed lipid chains with surfactant properties (e.g., egg phosphatidylethanolamine). A liposome design can employ surface ligands for attaching to unhealthy tissue. Non-limiting examples of liposomes include the multilamellar vesicle (MLV), the small unilamellar vesicle (SUV), and the large unilamellar vesicle (LUV). Liposomal physicochemical properties can be modulated to optimize penetration through biological barriers and retention at the site of administration, and to reduce a likelihood of developing premature degradation and toxicity to non-target tissues. Optimal liposomal properties depend on the administration route: large-sized liposomes show good retention upon local injection, small-sized liposomes are better suited to achieve passive targeting. PEGylation reduces the uptake of the liposomes by the liver and spleen, and increases the circulation time, resulting in increased localization at the inflamed site due to the enhanced permeability and retention (EPR) effect. Additionally, liposomal surfaces can be modified to achieve selective delivery of the encapsulated drug to specific target cells. Non-limiting examples of targeting ligands include monoclonal antibodies, vitamins, peptides, and polysaccharides specific for receptors concentrated on the surface of cells associated with the disease.

Compositions of the invention can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies. In some embodiments, a kit includes an inhalation delivery device, such as an inhaler, an atomizer, or a nebulizer. In some embodiments, a kit includes inhalation capsules of powders in a sealed blister pack.

Dosing.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

A compound described herein can be present in a composition in a range of from about 1 mg to about 500 mg. A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, or about 500 mg.

In some embodiments, a dose can be expressed in terms of an amount of the drug divided by the mass of the subject, for example, milligrams of drug per kilograms of subject body mass. In some embodiments, a compound of the invention is administered in an amount ranging from about 5 mg/kg to about 50 mg/kg, 250 mg/kg to about 2000 mg/kg, about 10 mg/kg to about 800 mg/kg, about 50 mg/kg to about 400 mg/kg, about 100 mg/kg to about 300 mg/kg, or about 150 mg/kg to about 200 mg/kg.

In some embodiments, a dose of Compound 1 can be about 2.5 mg to about 100 mg. In some embodiments, a dose of Compound 1 can be about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg. In some embodiments, a dose of Compound 1 can be about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, or about 0.9 mg/kg. In some embodiments, the invention describes administration of about 0.5 mg/kg or about 0.6 mg/kg of Compound 1. In some embodiments, a dose of Compound 1 can be about 10 mg. In some embodiments, a dose of Compound 1 can be administered once, twice, three times, or four times a day.

In some embodiments, a dose of a PDEV inhibitor can be about 5 mg, about 10 mg, about 15 mg, about 20 mg, about 25 mg, about 30 mg, about 35 mg, about 40 mg, about 45 mg, or about 50 mg. In some embodiments, a dose of a PDEV inhibitor can be about 20 mg. In some embodiments, a dose of a PDEV inhibitor can be about 40 mg. In some embodiments, a dose of a PDEV inhibitor can be administered once, twice, three times, or four times a day. In some embodiments, a 20 mg of a PDEV inhibitor is administered three times a day. In some embodiments, 40 mg of a PDEV inhibitor is administered once a day.

In some embodiments, a dose of an ET antagonist can be about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg. In some embodiments, a dose of an ET antagonist can be about 5 mg. In some embodiments, a dose of an ET antagonist can be about 10 mg. In some embodiments, a dose of an ET antagonist can be administered once, twice, three times, or four times a day. In some embodiments, 5 mg of an ET antagonist is administered once a day. In some embodiments, 10 mg of an ET antagonist is administered once a day. In some embodiments, 5 mg of an ET antagonist is administered twice a day.

In some embodiments, the invention describes administration of about 1 mg/kg, about 5 mg/kg, about 10 mg/kg, about 15 mg/kg, or about 20 mg/kg of a PDEV inhibitor an ET receptor antagonist. In some embodiments, the invention describes administration of about 10 mg/kg of a PDEV inhibitor. In some embodiments, the invention describes administration of about 10 mg/kg of an ET receptor antagonist.

Pharmacokinetic and Pharmacodynamic Measurements.

Pharmacokinetic and pharmacodynamics profile components can be used to describe a formulation disclosed herein. In some embodiments, a particular formulation can be described by any of the following parameters or a combination thereof:

i) k10: (first order) elimination rate constant;
ii) k12: rate of transfer from central to peripheral compartment;
iii) k21: rate of transfer from peripheral to central compartment;

iv) $t_{1/2}$alpha: distributive half-life;
v) $t_{1/2}$beta: elimination half-life;
vi) absorption half-life;
vii) V/F: apparent volume of distribution of a drug after extravascular administration;
viii) CL/F: apparent plasma clearance of a drug after extravascular administration;
ix) V2/F: central volume of distribution;
x) CL2/F: apparent inter-compartmental clearance;
xi) $C_{max}$: maximum plasma concentration at steady state;
xii) $T_{max}$: time to $C_{max}$;
xiii) $AUC_{0-t}$: area under plasma concentration-time curve from zero to the time of the last quantifiable concentration;
xiv) $AUC_{0-inf}$: area under plasma concentration-time curve from zero extrapolated to infinity;
xv) AUMC: total area under the first moment-time curve; or
xvi) MRT: mean residence time.

Pharmacokinetic and pharmacodynamic data can be obtained using various experimental techniques. In some embodiments, plasma drug concentration levels are determined with a validated liquid chromatograph/mass spectrometry-mass spectrometry (LC/MS-MS) method. In some embodiments, pharmacokinetic parameters can be determined using a standard non-compartmental method. In some embodiments, $C_{max}$, $AUC_{0-t}$, and $AUC_{0-inf}$ are analyzed statistically using log-transformed data.

Appropriate pharmacokinetic and pharmacodynamic profile components describing a particular composition or formulation can vary due to variations in drug metabolism in human subjects. Pharmacokinetic and pharmacodynamic profiles can be based on the determination of the mean parameters of a group of subjects. The group of subjects includes any reasonable number of subjects suitable for determining a representative mean, for example, 5 subjects, 10 subjects, 15 subjects, 20 subjects, 25 subjects, 30 subjects, 35 subjects, or more. The mean is determined, for example, by calculating the average of all subject's measurements for each parameter measured. A dose can be modulated to achieve a desired pharmacokinetic or pharmacodynamics profile, such as a desired or effective blood profile, as described herein.

The pharmacodynamic parameters can be any parameters suitable for describing compositions of the invention. For example, the pharmacodynamic profile can be obtained at a time after dosing of, for example, about zero minutes, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes, about 60 minutes, about zero hours, about 0.5 hours, about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 12.5 hours, about 13 hours, about 13.5 hours, about 14 hours, about 14.5 hours, about 15 hours, about 15.5 hours, about 16 hours, about 16.5 hours, about 17 hours, about 17.5 hours, about 18 hours, about 18.5 hours, about 19 hours, about 19.5 hours, about 20 hours, about 20.5 hours, about 21 hours, about 21.5 hours, about 22 hours, about 22.5 hours, about 23 hours, about 23.5 hours, or about 24 hours.

The pharmacokinetic parameters can be any parameters suitable for describing a compound or formulation. The $C_{max}$ can be, for example, not less than about 1 µg/mL; not less than about 5 µg/mL; not less than about 10 µg/mL; not less than about 15 µg/mL; not less than about 20 µg/mL; not less than about 25 µg/mL; not less than about 50 µg/mL; not less than about 75 µg/mL; not less than about 100 µg/mL; not less than about 200 µg/mL; not less than about 300 µg/mL; not less than about 400 µg/mL; not less than about 500 µg/mL; not less than about 600 µg/mL; not less than about 700 µg/mL; not less than about 800 µg/mL; not less than about 900 µg/mL; not less than about 1000 µg/mL; not less than about 1250 µg/mL; not less than about 1500 µg/mL; not less than about 1750 µg/mL; not less than about 2000 µg/mL; or any other $C_{max}$ appropriate for describing a pharmacokinetic profile of a compound or formulation described herein. The $C_{max}$ can be, for example, about 1 µg/mL to about 5,000 µg/mL; about 1 µg/mL to about 4,500 µg/mL; about 1 µg/mL to about 4,000 µg/mL; about 1 µg/mL to about 3,500 µg/mL; about 1 µg/mL to about 3,000 µg/mL; about 1 µg/mL to about 2,500 µg/mL; about 1 µg/mL to about 2,000 µg/mL; about 1 µg/mL to about 1,500 µg/mL; about 1 µg/mL to about 1,000 µg/mL; about 1 µg/mL to about 900 µg/mL; about 1 µg/mL to about 800 µg/mL; about 1 µg/mL to about 700 µg/mL; about 1 µg/mL to about 600 µg/mL; about 1 µg/mL to about 500 µg/mL; about 1 µg/mL to about 450 µg/mL; about 1 µg/mL to about 400 µg/mL; about 1 µg/mL to about 350 µg/mL; about 1 µg/mL to about 300 µg/mL; about 1 µg/mL to about 250 µg/mL; about 1 µg/mL to about 200 µg/mL; about 1 µg/mL to about 150 µg/mL; about 1 µg/mL to about 125 µg/mL; about 1 µg/mL to about 100 µg/mL; about 1 µg/mL to about 90 µg/mL; about 1 µg/mL to about 80 µg/mL; about 1 µg/mL to about 70 µg/mL; about 1 µg/mL to about 60 µg/mL; about 1 µg/mL to about 50 µg/mL; about 1 µg/mL to about 40 µg/mL; about 1 µg/mL to about 30 µg/mL; about 1 µg/mL to about 20 µg/mL; about 1 µg/mL to about 10 µg/mL; about 1 µg/mL to about 5 µg/mL; about 10 µg/mL to about 4,000 µg/mL; about 10 µg/mL to about 3,000 µg/mL; about 10 µg/mL to about 2,000 µg/mL; about 10 µg/mL to about 1,500 µg/mL; about 10 µg/mL to about 1,000 µg/mL; about 10 µg/mL to about 900 µg/mL; about 10 µg/mL to about 800 µg/mL; about 10 µg/mL to about 700 µg/mL; about 10 µg/mL to about 600 µg/mL; about 10 µg/mL to about 500 µg/mL; about 10 µg/mL to about 400 µg/mL; about 10 µg/mL to about 300 µg/mL; about 10 µg/mL to about 200 µg/mL; about 10 µg/mL to about 100 µg/mL; about 10 µg/mL to about 50 µg/mL; about 25 µg/mL to about 500 µg/mL; about 25 µg/mL to about 100 µg/mL; about 50 µg/mL to about 500 µg/mL; about 50 µg/mL to about 100 µg/mL; about 100 µg/mL to about 500 µg/mL; about 100 µg/mL to about 400 µg/mL; about 100 µg/mL to about 300 µg/mL; or about 100 µg/mL to about 200 µg/mL.

The $T_{max}$ of a compound or formulation described herein can be, for example, not greater than about 0.5 hours, not greater than about 1 hours, not greater than about 1.5 hours, not greater than about 2 hours, not greater than about 2.5 hours, not greater than about 3 hours, not greater than about 3.5 hours, not greater than about 4 hours, not greater than about 4.5 hours, not greater than about 5 hours, or any other $T_{max}$ appropriate for describing a pharmacokinetic profile of a compound or formulation described herein. In some embodiments, the $T_{max}$ of a compound or formulation described herein is not greater than about 1 minute, about 2 minutes, about 3 minutes, about 4 minutes, about 5 minutes, about 6 minutes, about 7 minutes, about 8 minutes, about 9 minutes, about 10 minutes, about 15 minutes, about 20 minutes, or about 25 minutes. The $T_{max}$ can be, for example, about 0.1 hours to about 24 hours; about 0.1 hours to about 0.5 hours; about 0.5 hours to about 1 hour; about 1 hour to about 1.5 hours; about 1.5 hours to about 2 hour; about 2 hours to about 2.5 hours; about 2.5 hours to about 3 hours; about 3 hours to about 3.5 hours; about 3.5 hours to about 4 hours; about 4 hours to about 4.5 hours; about 4.5 hours to about 5 hours; about 5 hours to about 5.5 hours; about 5.5 hours to about 6 hours; about 6 hours to about 6.5 hours; about 6.5 hours to about 7 hours; about 7 hours to about 7.5 hours; about 7.5 hours to about 8 hours; about 8 hours to about 8.5 hours; about 8.5 hours to about 9 hours; about 9 hours to about 9.5 hours; about 9.5 hours to about 10 hours; about 10 hours to about 10.5 hours; about 10.5 hours to about 11 hours; about 11 hours to about 11.5 hours; about 11.5 hours to about 12 hours; about 12 hours to about 12.5 hours; about 12.5 hours to about 13 hours; about 13 hours to about 13.5 hours; about 13.5 hours to about 14 hours; about 14 hours to about 14.5 hours; about 14.5 hours to about 15 hours; about 15 hours to about 15.5 hours; about 15.5 hours to about 16 hours; about 16 hours to about 16.5 hours; about 16.5 hours to about 17 hours; about 17 hours to about 17.5 hours; about 17.5 hours to about 18 hours; about 18 hours to about 18.5 hours; about 18.5 hours to about 19 hours; about 19 hours to about 19.5 hours; about 19.5 hours to about 20 hours; about 20 hours to about 20.5 hours; about 20.5 hours to about 21 hours; about 21 hours to about 21.5 hours; about 21.5 hours to about 22 hours; about 22 hours to about 22.5 hours; about 22.5 hours to about 23 hours; about 23 hours to about 23.5 hours; or about 23.5 hours to about 24 hours.

The $AUC_{0-inf}$ or $AUC_{0-t}$ of a compound or formulation described herein can be, for example, not less than about 1 µg/g·min, not less than about 5 µg/g·min, not less than about 10 µg/g·min, not less than about 20 µg/g·min, not less than about 30 µg/g·min, not less than about 40 µg/g·min, not less than about 50 µg/g·min, not less than about 100 µg/g·min, not less than about 150 µg/g·min, not less than about 200 µg/g·min, not less than about 250 µg/g·min, not less than about 300 µg/g·min, not less than about 350 µg/g·min, not less than about 400 µg/g·min, not less than about 450 µg/g·min, not less than about 500 µg/g·min, not less than about 600 µg/g·min, not less than about 700 µg/g·min, not less than about 800 µg/g·min, not less than about 900 µg/g·min, not less than about 1000 µg/g·min, not less than about 1250 µg/g·min, not less than about 1500 µg/g·min, not less than about 1750 µg/g·min, not less than about 2000 µg/g·min, not less than about 2500 µg/g·min, not less than about 3000 µg/g·min, not less than about 3500 µg/g·min, not less than about 4000 µg/g·min, not less than about 5000 µg/g·min, not less than about 6000 µg/g·min, not less than about 7000 µg/g·min, not less than about 8000 µg/g·min, not less than about 9000 µg/g·min, not less than about 10,000 µg/g·min, or any other $AUC_{(0-inf)}$ appropriate for describing a pharmacokinetic profile of a compound described herein. The $AUC_{(0-inf)}$ of a compound can be, for example, about 1 µg/g·min to about 10,000 µg/g·min; about 1 µg/g·min to about 10 µg/g·min; about 10 µg/g·min to about 25 µg/g·min; about 25 µg/g·min to about 50 µg/g·min; about 50 µg/g·min to about 100 µg/g·min; about 100 µg/g·min to about 200 µg/g·min; about 200 µg/g·min to about 300 µg/g·min; about 300 µg/g·min to about 400 µg/g·min; about 400 µg/g·min to about 500 µg/g·min; about 500 µg/g·min to about 600 µg/g·min; about 600 µg/g·min to about 700 µg/g·min; about 700 µg/g·min to about 800 µg/g·min; about 800 µg/g·min to about 900 µg/g·min; about 900 µg/g·min to about 1,000 µg/g·min; about 1,000 µg/g·min to about 1,250 µg/g·min; about 1,250 µg/g·min to about 1,500 µg/g·min; about 1,500 µg/g·min to about 1,750 µg/g·min; about 1,750 µg/g·min to about 2,000 µg/g·min; about 2,000 µg/g·min to about 2,500 µg/g·min; about 2,500 µg/g·min to about 3,000 µg/g·min; about 3,000 µg/g·min to about 3,500 µg/g·min; about 3,500 µg/g·min to about 4,000 µg/g·min; about 4,000 µg/g·min to about 4,500 µg/g·min; about 4,500 µg/g·min to about 5,000 µg/g·min; about 5,000 µg/g·min to about 5,500 µg/g·min; about 5,500 µg/g·min to about 6,000 µg/g·min; about 6,000 µg/g·min to about 6,500 µg/g·min; about 6,500 µg/g·min to about 7,000 µg/g·min; about 7,000 µg/g·min to about 7,500 µg/g·min; about 7,500 µg/g·min to about 8,000 µg/g·min; about 8,000 µg/g·min to about 8,500 µg/g·min; about 8,500 µg/g·min to about 9,000 µg/g·min; about 9,000 µg/g·min to about 9,500 µg/g·min; or about 9,500 µg/g·min to about 10,000 µg/g·min.

The plasma concentration of a compound or formulation described herein can be, for example, not less than about 1 ng/mL, not less than about 5 ng/mL, not less than about 10 ng/mL, not less than about 15 ng/mL, not less than about 20 ng/mL, not less than about 25 ng/mL, not less than about 50 ng/mL, not less than about 75 ng/mL, not less than about 100 ng/mL, not less than about 150 ng/mL, not less than about 200 ng/mL, not less than about 300 ng/mL, not less than about 400 ng/mL, not less than about 500 ng/mL, or any other plasma concentration of a compound or formulation described herein. The plasma concentration can be, for example, about 1 ng/mL to about 500 ng/mL; about 1 ng/mL to about 5 ng/mL; about 5 ng/mL to about 10 ng/mL; about 10 ng/mL to about 25 ng/mL; about 25 ng/mL to about 50 ng/mL; about 50 ng/mL to about 75 ng/mL; about 75 ng/mL to about 100 ng/mL; about 100 ng/mL to about 150 ng/mL; about 150 ng/mL to about 200 ng/mL; about 200 ng/mL to about 250 ng/mL; about 250 ng/mL to about 300 ng/mL; about 300 ng/mL to about 350 ng/mL; about 350 ng/mL to about 400 ng/mL; about 400 ng/mL to about 450 ng/mL; or about 450 ng/mL to about 500 ng/mL.

The plasma concentration of a compound or formulation described herein can be, for example, not less than about 1 µg/mL, not less than about 5 µg/mL, not less than about 10 µg/mL, not less than about 15 µg/mL, not less than about 20 µg/mL, not less than about 25 µg/mL, not less than about 50 µg/mL, not less than about 75 µg/mL, not less than about 100 µg/mL, not less than about 150 µg/mL, not less than about 200 µg/mL, not less than about 300 µg/mL, not less than about 400 µg/mL, not less than about 500 µg/mL, or any other plasma concentration of a compound or formulation described herein. The plasma concentration can be, for example, about 1 µg/mL to about 500 µg/mL; about 1 µg/mL to about 5 µg/mL; about 5 µg/mL to about 10 µg/mL; about 10 µg/mL to about 25 µg/mL; about 25 µg/mL to about 50 µg/mL; about 50 µg/mL to about 75 µg/mL; about 75 µg/mL to about 100 µg/mL; about 100 µg/mL to about 150 µg/mL; about 150 µg/mL to about 200 µg/mL; about 200 µg/mL to about 250 μg/mL; about 250 μg/mL to about 300 μg/mL; about 300 μg/mL to about 350 μg/mL; about 350 μg/mL to about 400 μg/mL; about 400 μg/mL to about 450 μg/mL; or about 450 μg/mL to about 500 μg/mL.

Indications.

The disclosure describes the use of a combination of compounds to treat a condition. In some embodiments, the condition is a pulmonary disorder, for example, PAH, PH due to left heart disease, PH due to lung disease, PH due to blood clots in the lungs, or PH resulting from blood and other rare disorders.

In some embodiments, the disclosure describes the use of a combination of compounds to treat PAH. In some embodiments, the PAH is primary PAH, idiopathic PAH, heritable PAH, drug and toxin-induced PAH, or PAH associated with other systemic diseases. In some embodiments, heritable PAH is caused by BMPR2, ALK1, endoglin, SMAD9, CAV1, or KCNK3. In some embodiments, the drug and toxin-induced PAH is induced by use of amphetamines, methamphetamines, cocaine, or fenfluramine-phentermine. In some embodiments, PAH is associated with other systemic diseases and is caused by a connective tissue disease (e.g., scleroderma, systemic lupus erythematosus, mixed connective tissue disease, and rheumatoid arthritis), human immunodeficiency virus (HIV) infection, portal hypertension, or congenital heart disease. In some embodiments, the disclosure can be used to treat pulmonary veno-occlusive disease (PVOD) or pulmonary capillary hemangiomatosis (PCH).

In some embodiments, the PH due to left heart disease, for example, left heart disease caused by left ventricular systolic dysfunction, left ventricular diastolic dysfunction, valvular heart disease, left heart inflow and outflow obstructions not due to valvular disease, or congenital cardiomyopathies. In some embodiments, the PH is due to lung disease, for example, chronic obstructive pulmonary disease (COPD), interstitial lung diseases, sleep-disordered breathing (e.g., sleep apnea), alveolar hypoventilation disorders, chronic high altitude exposure, or developmental abnormalities of the lung.

In some embodiments, the PH is CTEPH. In some embodiments, the PH is PH with unclear or multifactorial mechanisms, such as PH caused by hematologic disorders (e.g., certain types of anemia, myeloproliferative disorders, or splenectomy), systemic disorders that have lung involvement (e.g., sarcoidosis, Langerhan cell histiocytosis, neurofibromatosis, vasculitis, or lymphangioleiomyomatosis), metabolic disorders (e.g., rare diseases of impaired cell metabolism or thyroid disease), or other unclassified diseases (e.g., chronic renal failure, tumors obstructing the pulmonary arteries, and other rare diseases).

In some embodiments, the condition to be treated is a pulmonary disorder associated with abnormal right ventricular systolic pressure (RVSP), pulmonary pressure, cardiac output, right ventricular hypertrophy, or pulmonary arterial hypertrophy. In some embodiments, the condition to be treated is lung cancer. In some embodiments, the condition to be treated is pulmonary angiosarcoma.

EXAMPLES

Example 1: In Vivo Studies

Male Sprague Dawley (SD) rats (weight: 300-330 g; Taconic) were used to test the effects of Compound 1 alone and in combination with ambrisentan and tadalafil. Animals were housed in standard rat cages with 12-hour light/dark cycles, and had ad libitum access to standard rat chow and water. Animals were cared for and used in accordance with the National Institutes of Health Guide for the Care and Use of Animals.

Example 2: Experimental Design 3.1 Inhalation Pharmacokinetic Study

Male Sprague Dawley rats inhaled a Compound 1 dry powder formulation (Compound 1/leucine) via nose-only exposure for 60 minutes. The average deposited dose for the inhalation pharmacokinetic study was 0.4 mg/kg, with an assumed deposition fraction of 0.1. Rats were placed on an exposure tower in a staggered fashion to allow sufficient time for sampling between animals.

After the inhalation dose was completed, the rats were placed under general anesthesia with isoflurane, intubated via a tracheotomy, and placed on a pressure-regulated ventilator. A sternotomy was then performed on each rat. At designated time points, a venous sample was taken from the right ventricle (RV), and an arterial sample was taken from the left ventricle (LV). 1 mL of blood was placed in an Eppendorf tube containing 10 μL EDTA for each sample, and the venous and arterial samples were placed on ice.

The right and left pulmonary arteries, veins, and bronchi of the rats were clamped. The lung lobes (i.e., right upper lobe (RUL), right middle lobe (RML), right lower lobe (RLL), accessory lung lobe (Acc), left upper lobe (LUL), left middle lobe (LML), and left lower lobe (LLL)) were removed, blotted to remove blood, and snap frozen in liquid nitrogen. The rats were euthanized under general anesthesia by exsanguination. Blood samples obtained from the rats were separated by centrifuge, and the plasma supernatants were aliquoted into Eppendorf tubes. The plasma samples and lung lobes were stored at minus 80° C. until the samples and lung lobes were extracted and assayed.

3.2 AAV-PDGFB SU5416 Hypoxia Study

Adeno-associated virus (AAV)-PDGFB was administered by pulmonary insufflation to male SD rats to overexpress PDGFBB in the lung. Two serotypes of AAV were used to produce rats that overexpressed PDGFBB: AAV-5 and AAV6.2. Rat PDGFB was overexpressed under control of the cytomegalovirus (CMV) promoter. AAV-5-PDGFB 4.3× $10^{12}$ genome copies (GC) and AAV-6.2-PDGFB $1.6 \times 10^{11}$ GC were insufflated into each rat. SEQ ID NO.: 1 shows the sequence of rat PDGFB that was overexpressed under control of the CMV promoter.

```
                                           SEQ ID NO.: 1
    1  gtgaagacga accatcggct gccgtgttcc ttttcctctc tgaggttgga gtcccctgcg 61  cgccccaca  cggctagacg ccttggctgg ttcgcgacgc agcccccaga ccgtggatgc 121  tgcgtgggc  tcgggatccg cccaggtagc ggctttggac cccggtccct cgtccaggtc 181  ctccccaacc cccagcgac  ggagccgggg ccggggcgg cggcgcccgg gggccatgcg 241  ggtgagccgc ggtggcggct gcagcggcct gagctcctga tcgcggcgga cccgagcgga
```

-continued

```
 301 gcccaccctc ctccccagcc cccccaccct ggccgcgggg
     gcggcgcgct ccgtctacgc
 361 gtccggggcc ccgtggggcc gggcccggag tcggcatgaa
     tcgctgctgg gcgctcttcc
 421 tgcctctctg ctgctacctg cgtctggtca gcgctgaggg
     ggatcccatt cctgaggaac
 481 tctatgaaat gctgagtgac cactccatcc gctcctttga
     tgaccttcag cgcctgctgc
 541 acagagactc cgtagacgaa gatgggctg agctggactt
     gaacatgacc cgagcacatt
 601 ctggagtcga gtcggaaagc tcatctcgag ggaggaggag
     cctagggtct ctggctgcag
 661 cagagcctgc cgtaatcgcc gagtgcaaga cgcgtacaga
     ggtgttccag atctcgcgga
 721 acctcatcga tcgcaccaat gccaacttcc tggtgtggcc
     gccctgcgtg gaggtgcagc
 781 gctgctcggg ctgctgcaat aaccgcaatg tgcagtgccg
     ggcctcgcag gtgcagatgc
 841 ggccggtgca ggtgagaaag atcgaaattg tgagaaagaa
     gccagtcttc aagaaggcca
 901 cagtgaccct ggaggaccat ctggcctgca agtgtgagac
     agtagtgacc cctcggcccg
 961 tgactcgaag tcctgggaca tccagggagc atcgagccaa
     gacacctcaa actcgggtga
1021 ccgttcggac ggtgcgaatc cgccggcccc ccaaagggaa
     gcaccgaaag tttaagcaca
1081 cccatgacaa gaaggcactg aaggagatcc ttggagccta
     ggggtgtcag cgagagtgtg
1141 ggcagggtta tttaatatgg tatttgctgt actgccccca
     tggggtcctt ggagtgataa
1201 tgttgttccc ctcgtccgtc tgtctcgatg cctgattcgg
     acggccaatg gtgcttccct
1261 cgccccgcgt gcccagccac ctccaccagc agcaatccct
     gccctgcagc tccagaagca
1321 aaggaaggac tccactccag gctgctgctt ccctctaccc
     caagaacctg ggacaagcgt
1381 gcggagcttc acagaggact ggaccggccc cagagcctgg
     catttagcct gaggacctct
1441 gcatgtcctg cctggttcct ggaccactgg ccagctagca
     gggaatactt tcaggcaggc
```

-continued

```
1501 tagggtccct tgcagtcctg tggcagggag cacggactgg
     aggaactctc atggcaccca
1561 gatctgccac gcactcatct ctccctgtcc ctttagccta
     cagtggcttt tcattttata
1621 agtatgaaat cgtggaagac atgaactcct ctgggcaggt
     ggccacatgc cttctctgat
1681 ggattagagg tgcattgtgc ttgtgaaaaa aaaaaaaaaa
     aaa
```

Four weeks later, 20 mg/kg of semaxanib (SU5416) was administered using intraperitoneal (i.p.) injection, and the rats were housed in a hypoxia chamber at fraction of inspired oxygen ($FiO_2$) 10% for 3 weeks. The treatment groups were divided into four groups (TABLE 1): 1) vehicle by gavage once daily and vehicle by inhalation twice daily (V-V); 2) 10 mg/kg of tadalafil and 10 mg/kg of ambrisentan by gavage once daily and vehicle by inhalation twice daily (TA-V); 3) vehicle by gavage once daily and 0.6 mg/kg of Compound 1 by inhalation twice daily (V-PK); and 4) 10 mg/kg of tadalafil and 10 mg/kg of ambrisentan by gavage once daily and 0.6 mg/kg of Compound 1 by inhalation twice daily (TA-PK). Daily treatments were administered starting day 2 after removing the rats from the hypoxia chamber and were continued for 4 weeks (28 days).

TABLE 1

| Abbreviation | Treatment |
| --- | --- |
| V-V | Vehicle gavage one daily<br>vehicle inhalation once daily |
| TA-V | 10 mg/kg ambrisentan and tadalafil gavage one daily<br>vehicle inhalation once daily |
| V-PK | Vehicle gavage one daily<br>inhalation 0.6 mg/kg Compound 1 twice daily |
| TA-PK | 10 mg/kg ambrisentan and tadalafil gavage one daily<br>inhalation 0.6 mg/kg Compound 1 twice daily |

At the end of the study, the RVSP of each rat was measured, and the animal was heparinized. The right middle lobe of the lung was then removed and placed in liquid nitrogen. The rats were exsanguinated under general anesthesia, and the remaining lung and heart were removed. The pulmonary artery was perfused with heparinized saline and fixed using 10% formalin under low pressure. The heart chambers were dissected, weighed, and fixed in formalin. The remaining lung was fixed in formalin by infused via the trachea. To measure the RVSP of the rats, the animals were sedated with isoflurane, intubated via a tracheostomy, and ventilated with a TOPO™ pressure-regulated ventilator. The peak inspiratory pressure was 18 cm $H_2O$, and the positive end-expiratory pressure (PEEP) was 5 cm $H_2O$. A sternotomy was performed, and a Scisense high-fidelity catheter was inserted via the RV apex. Parameters measured included: right ventricular end systolic pressure (RVESP), RV end diastolic pressure (RVEDP), RV hemodynamics, RV hypertrophy, RV end diastolic volume, RV end systolic volume, RV ejection fraction, PDGFR signaling, cardiac output, and stroke work.

3.3 Administration of Compound 1 Powder for Inhalation

The formulation of Compound 1 contained about 50% compound 1 and about 50% leucine. The compounds were dissolved in an ethanol/water solution, and the mixture was spray dried to form a dry powder with aerosol characteristics suitable for inhalation.

Compound 1 powder for inhalation was delivered to the rats through a 12-port nose-only inhalation chamber using a Vilnius Aerosol Generator (VAG). Compound 1 powder for inhalation was loaded in the VAG, and the flow rate was set to 3 L/min for 60 min. The amount of Compound 1 inhaled was measured with a Mercer impactor at a flow rate of 1.5 L/min. The aerosol MMAD of Compound 1 powder for inhalation was determined using a Next Generation Impactor (NGI).

3.4 Plethysmography

Plethysmography was performed with an Emka dual chamber plethysmograph and Emka iox software. Parameters measured included breathing frequency, tidal volume, minute ventilation (MV), peak inspiratory and expiratory flow, and airway resistance. Measurements were made before the first dose of drug and at the end of the study.

3.5 Histology and Morphometric Analysis

The heart and lungs were removed from ventilated animals under general anesthesia. Heparinized saline was infused under pressure through the main pulmonary artery. The right middle lobe was immediately tied off and placed in liquid nitrogen for quantitative polymerase chain reaction (qPCR) and western blot analysis. The heart was removed, and the RV free wall, interventricular septum, and left ventricular (LV) free wall were dissected and weighed. Buffered formalin (10%) was infused under pressure through the pulmonary artery and the trachea. Morphometric analysis was performed on H&E (hematoxylin and eosin)-stained formalin fixed tissue sectioned at 8 µm. The media area and lumen area of pulmonary arterioles were measured using ImageJ software. Measurements were made on at least 20 pulmonary arterioles per section per rat. The ratio of the lumen area to the total media area (L/M) was determined. The L/M ratio normalized the variation in total pulmonary arteriole area.

3.6 Immunohistochemistry

Antigen retrieval was performed using heat-induced epitope retrieval. Immunohistochemistry of lung sections was performed for PDGFBB, total PDGFRα, total PDGFRβ, pPDGFRα, and pPDGFRβ. Signal detection was performed with an EXPOSE horseradish peroxidase/diaminobenzidine (HRP/DAB) kit.

3.7 Western Blot Analysis

Lung tissue samples were homogenized in pH 7.4 lysis buffer containing 50 mM Tris-HCl, 50 mM NaCl, 5 mM EDTA, 1% Triton X-100, 0.05% SDS, 50 mM NaF, 10 mM β-glycerophosphate, sodium pyrophosphate, 100 µM $Na_3VO_4$, and a phosphatase and protease inhibitor. Lysates were normalized and separated on 7.5% or 12% polyacrylamide gels and transferred to nitrocellulose membranes. After blocking, the membranes were probed with one of the following antibodies: anti-PDGFRβ, anti-phospho (Y1021)-PDGFRβ, pMYPT, MYPT, pSTAT3, or STAT3. The samples were incubated overnight on a shaker, followed by a 1 hour incubation with secondary antibodies conjugated with HRP. Bound antibodies were detected by chemiluminescence using an enhanced chemiluminsecence (ECL) detection system, and quantified by densitometry using a Licor C-Digit® Blot Scanner.

3.8 PDGFB Gene Expression

RNA from lung tissue was isolated using TRIzol™ reagent. The RNA concentration was measured using a Nanodrop™ 1000 Spectrophotometer. Equal amounts of RNA of each sample were transcribed to cDNA using a high-capacity cDNA Reverse Transcription kit. Reverse transcription (RT)-qPCR reactions were set up using TaqMan™ Gene Expression Master Mix and TaqMan™ primers/probes for PDGFB and 18S. The gene expression assay was carried out using a QuantStudio™ 6 Flex system. Gene expression was normalized to the expression of 18S, which was used as a housekeeping gene.

3.9 Enzyme-Linked Immunosorbent Assays (ELISA)

ELISA kits specific for phospho-PDGF receptor β (Y751) were used to compare the dose effects of Compound 1 and imatinib on PDGFBB-stimulated PDGFRβ phosphorylation in human lung fibroblasts.

Adult human lung fibroblasts (HLFa) were maintained in subculture at no more than 8 passages. Cells were cultured in Dulbecco's modified eagle's medium (DMEM) with 5% fetal bovine serum (FBS), 4 mM GlutaMAX™, and a 1× antibiotic-antimycotic solution. The cells were seeded into T-25 flasks and grown to approximately 70-80% confluence. Once the cells were at approximately 70-80% confluence, the cells were serum starved for approximately 24 hours.

Cells were treated with Compound 1 or imatinib to test for inhibition of stimulation of pPDGFRβ (Y751) by PDGFBB. The cells were pre-treated with Compound 1 at the indicated concentrations and incubated in a 37° C., 5% $CO_2$ incubator for 30 minutes. Following the pre-treatment, 50 ng/mL of PDGFBB was added to the flasks, and the cells were incubated at 37° C., 5% $CO_2$ for 7.5 minutes. After treatment, the cells were lysed in a cell lysis buffer containing phenylmethanesulfonyl fluoride (PMSF). The cell lysate supernatants were collected for protein quantitation and assayed using a Micro BCA™ Protein assay kit. The cell lysates were then used in Sandwich ELISA assays to quantify the amounts of pPDGFRalpha (Y849) and pPDGFRbeta (Y751). Each condition was performed in duplicate.

Samples were diluted in the ELISA assay buffer, transferred to pPDGFR mAb coated microwells, and incubated at 37° C. for 2 hours. After sample-well incubation, the wells were washed 4 times with a 1×ELISA wash buffer. Detection antibodies were added to each well, and the samples were incubated for 1 hour in a 37° C. incubator. Following incubation with the detection antibody, the wells were washed. An HRP-linked secondary antibody was added to each well, and the samples were incubated for 30 minutes in a 37° C. incubator. Following HRP-linked secondary antibody incubation, the wells were washed again. 3,3',5,5'-Tetramethylbenzidine (TMB) substrate was added to each well and incubated for 10 minutes in a 37° C. incubator. After TMB incubation, a stop solution was added to each well containing TMB. The plate was shaken gently for a few seconds, and the sample wells were read at 450 nm using a spectrophotometric plate reader and Genesis Lite Software.

3.10 Statistical Analysis

Statistical analysis was performed using XLSTAT 2017.4. Data shown are mean±standard error of the mean (SEM) unless otherwise noted. Differences between the groups were analyzed using analysis of variance (ANOVA) followed by the Bonferroni correction or Student-Newman-Keuls (SNK) test. In some cases, Dunnett's test was used as a comparison to a control group. In cases where variance was not normal, Kruskal-Wallis non-parametric analysis was performed followed by the Steel-Dwass-Critchlow-Fligner procedure for multiple group comparisons. Significance was set at the p=0.05 level.

Example 3: ELISA Assay of PDGFRβ in Human Lung Fibroblasts

Figure 2:
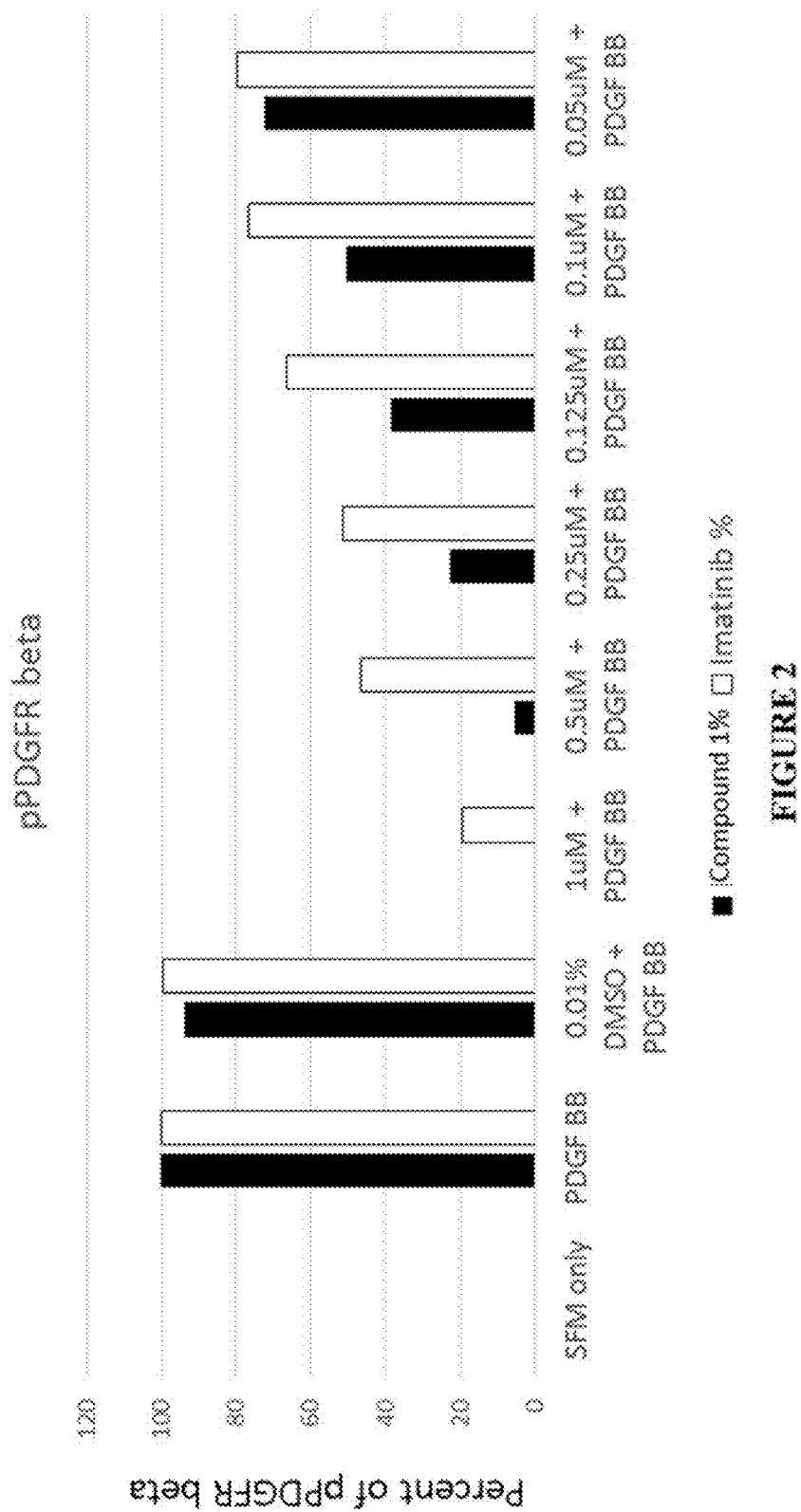
FIG. 2 shows results from an ELISA of phosphorylated PDGFRβ in human lung fibroblasts treated with various concentrations of PDGFB with or without Compound 1 and imatinib.

FIG. 2 shows results from an ELISA of phosphorylated PDGFRβ (pPDGFRβ) in human lung fibroblasts treated with PDGFB, with or without Compound 1 and imatinib.

Compound 1 was about 2.5-fold more potent than imatinib at inhibiting PDGFB-stimulated phosphorylation of PDGFRβ in human lung fibroblasts. The $IC_{50}$ of compound 1 for inhibiting phosphorylation of PDGFRβ was 0.1 μM. The $IC_{50}$ of imatinib for inhibiting phosphorylation of PDGFRβ was 0.25 μM.

Example 4: Pharmacokinetics of Inhaled Compound 1

After passive inhalation of Compound 1 as a dry powder formulation in rats, the concentration of Compound 1 in the lung was 20-80-fold higher than the concentration of Compound 1 in arterial and venous plasma concentrations. The average deposited dose of Compound 1 was 0.4 mg/kg; n=2 for t=240 min, 1440 min; n=3 for all other time points.

Figure 3:
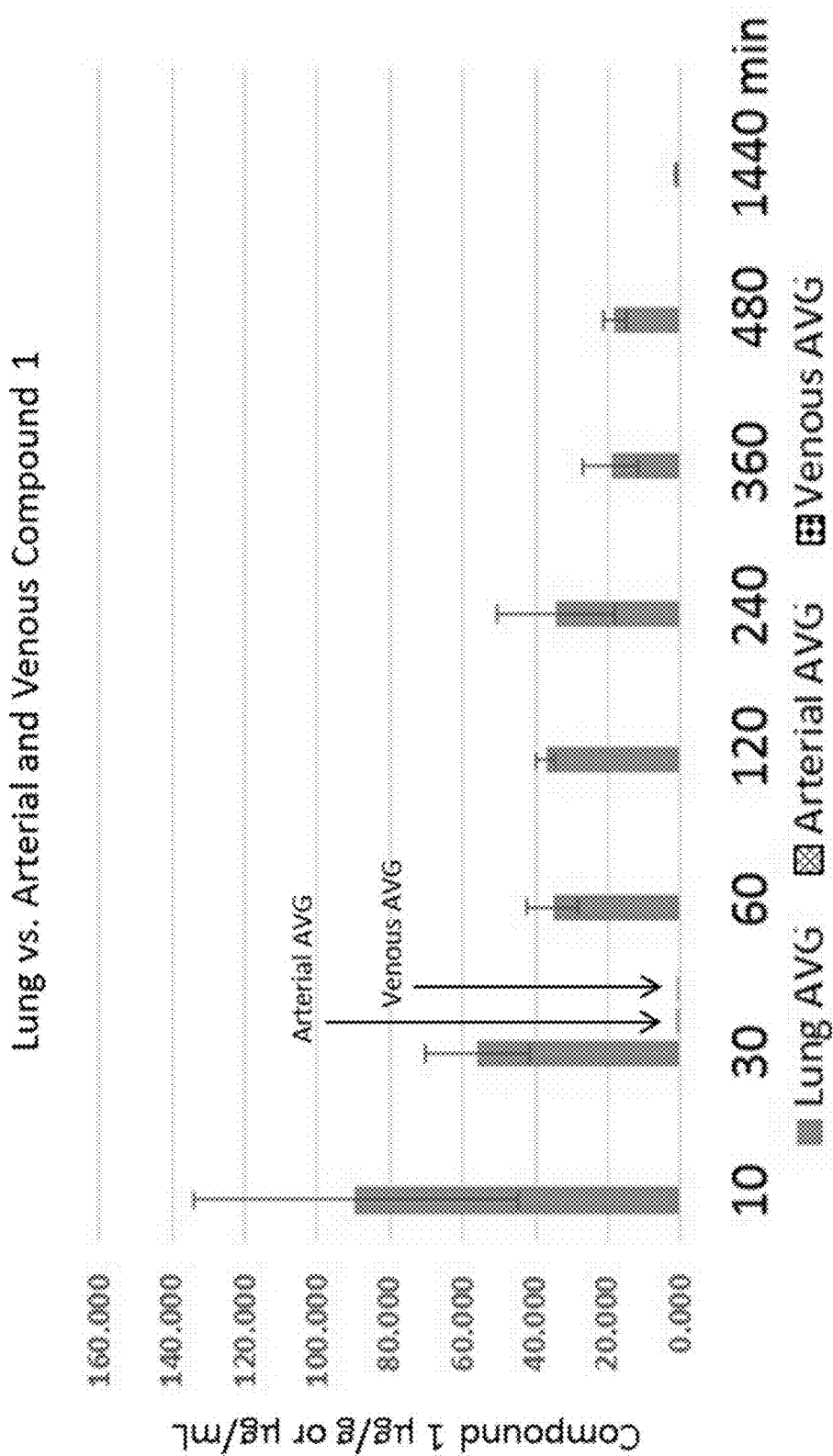
FIG. 3 compares the average lung, arterial, and venous concentrations of Compound 1 after inhalation in rats.
Figure 4:
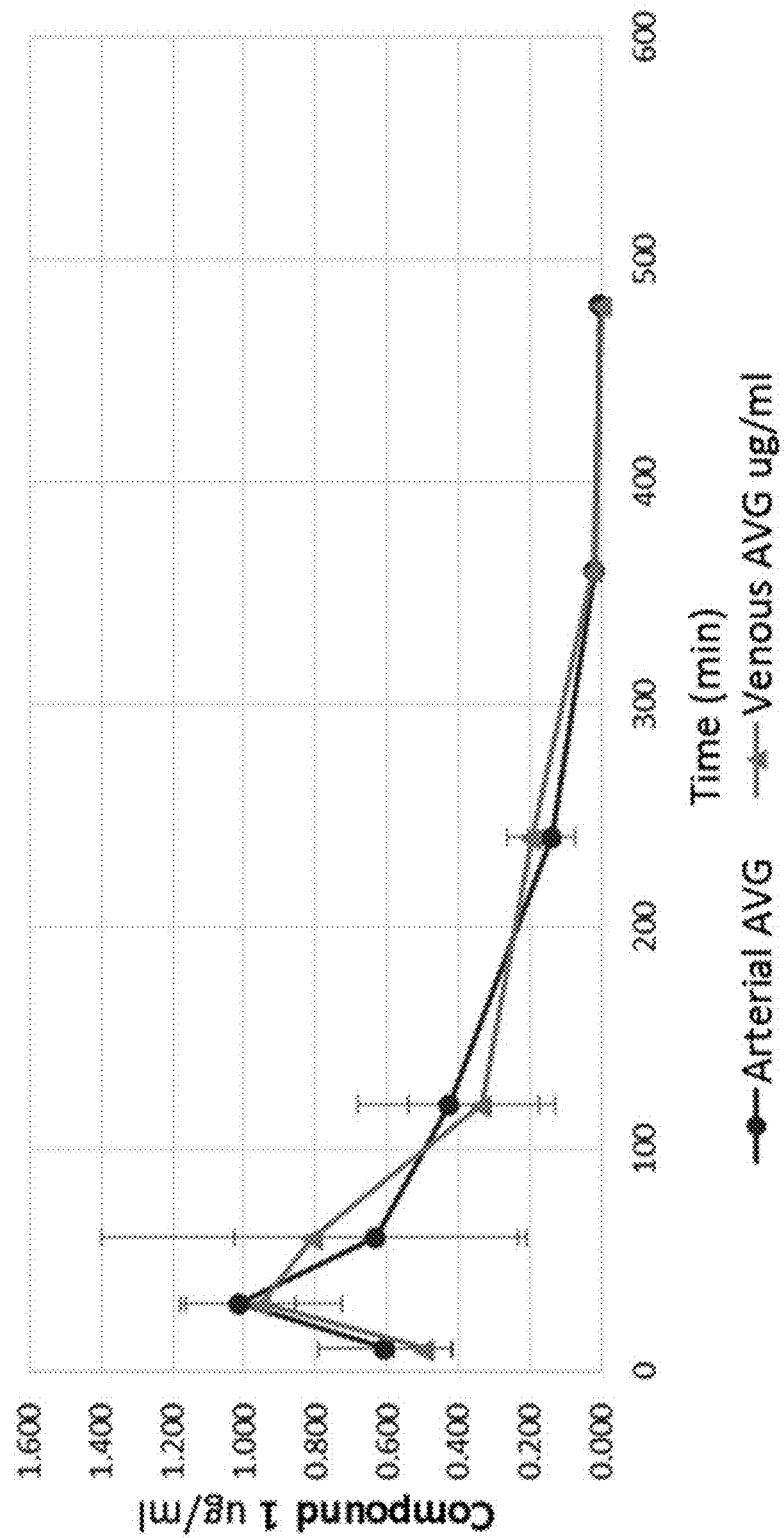
FIG. 4 shows changes in average arterial and venous concentrations of Compound 1 over time.

FIG. 3 compares the lung, arterial, and venous concentrations of Compound 1 after inhalation in rats. The arterial and venous concentrations of Compound 1 were several fold lower than the concentration of Compound 1 in the lung; the arterial and venous concentrations of Compound 1 were close to the baseline and are not prominent in the graph. FIG. 4 shows the arterial and venous concentrations of Compound 1 on a smaller scale over a time period of approximately 500 minutes. The data show that the maximum arterial and venous average concentrations of Compound 1 were about 1 μg/mL. The average arterial and venous concentrations of Compound 1 decreased rapidly after administration, and reached zero about 400 minutes after administration.

Two compartment pharmacokinetic modeling was performed using PK Solver 2.0. The results are shown in TABLE 2 and TABLE 3. The terminal half-life of Compound 1 in lung ($t_{1/2}β$) was 385.9 minutes compared to 125 minutes in plasma. TABLE 2 shows the pharmacokinetic parameters for the concentration of Compound 1 in the lung. TABLE 3 shows the pharmacokinetic parameters for the concentration of Compound 1 in venous plasma concentrations.

TABLE 2

| Parameter | Unit | Value |
|---|---|---|
| k10 | 1/min | 0.005 |
| k12 | 1/min | 0.038 |
| k21 | 1/min | 0.023 |
| t1/2Alpha | min | 10.747 |
| t1/2Beta | min | 385.882 |
| t1/2ka | min | 0.858 |
| V/F | (μg/kg)/(ug/g) | 3.147 |
| CL/F | (μg/kg)/(ug/g)/min | 0.016 |
| V2/F | (μg/kg)/(ug/g) | 5.126 |
| CL2/F | (μg/kg)/(ug/g)/min | 0.120 |
| Tmax | min | 3.906 |
| Cmax | ug/g | 107.402 |
| AUC 0-t | ug/g*min | 23583.976 |
| AUC 0-inf | ug/g*min | 25403.578 |
| AUMC | ug/g*min² | 13478872.169 |
| MRT | min | 530.590 |

TABLE 3

| Parameter | Unit | Value |
|---|---|---|
| k10 | 1/min | 0.016 |
| k12 | 1/min | 0.008 |
| k21 | 1/min | 0.010 |
| t1/2Alpha | min | 24.163 |
| t1/2Beta | min | 125.025 |
| t1/2ka | min | 19.557 |
| V/F | (μg/kg)/(μg/ml) | 187.131 |
| CL/F | (μg/kg)/(μg/ml)/min | 3.034 |
| V2/F | (μg/kg)/(μg/ml) | 156.581 |
| CL2/F | (μg/kg)/(μg/ml)/min | 1.536 |
| Tmax | min | 35.355 |
| Cmax | μg/ml | 0.924 |
| AUC 0-t | μg/ml*min | 116.480 |
| AUC 0-inf | μg/ml*min | 127.567 |
| AUMC | μg/ml*min² | 18052.306 |
| MRT | min | 141.512 |

Example 5: Western Blot Analyses

Western blot analyses using an antibody specific for pPDGFRβ at Y1021 were performed to determine the effects of inhaled Compound 1 on pPDGFRβ levels in the lungs of treated animals. Animals were treated with inhaled Compound 1 or a vehicle. The samples were subjected to sodium dodecyl sulfate polyacrylamide gel electrophoresis (SDS-PAGE), and the resulting gel was transferred to a nylon membrane.

Figure 5:
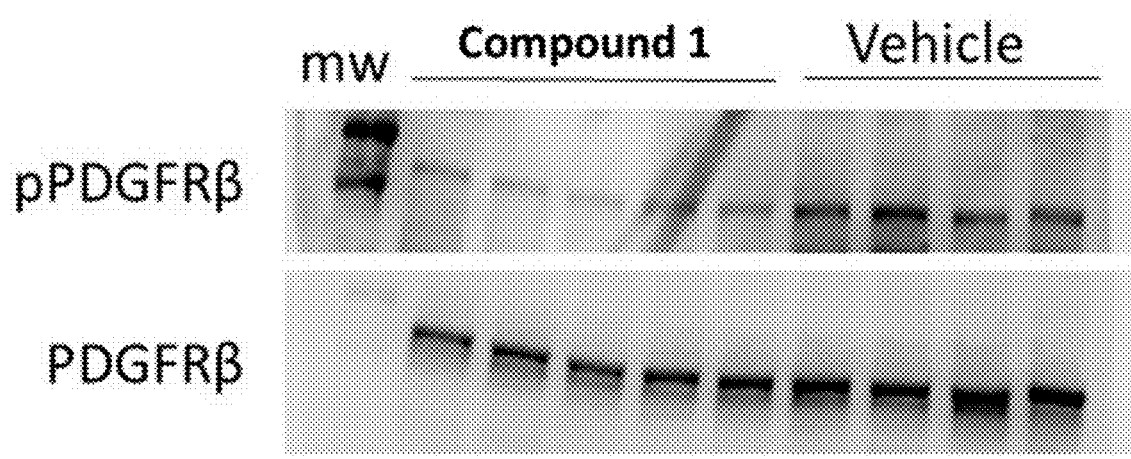
FIG. 5 shows a Western blot analysis of pPDGFRβ and PDGFRβ from lung lysates obtained from rats with pulmonary hypertension after treatment with Compound 1.

FIG. 5 shows Western blots of samples demonstrating that treatment with Compound 1 decreased the ratio of pPDGFRβ compared to the levels of total PDGFRβ. The top panel of FIG. 5 shows the Western blot after incubation with a primary antibody specific for pPDGFRβ phosphorylated at Y1021. The bottom panel of FIG. 5 shows the Western blot after incubation with an antibody specific for total PDGFRβ. The results show that animals treated with Compound 1 exhibited decreased pPDGFRβ levels compared to animals treated with the vehicle.

Figure 6:
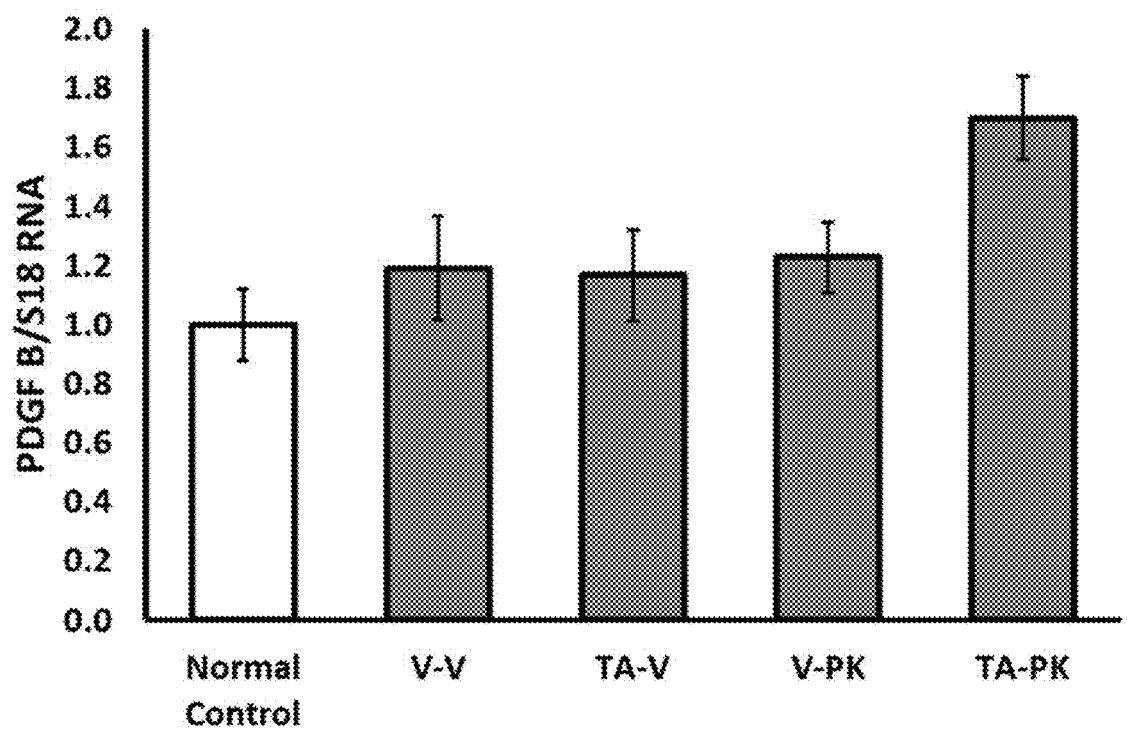
FIG. 6 shows increased lung gene expression of PDGFB in the AAV-PDGFB SU5416 hypoxia model.

Example 6: Efficacy of Inhaled Compound 1 in Combination with Tadalafil and Ambrisentan PDGFB gene expression was increased in the AAV-PDGFB SU5416 Hypoxia rat model. Treatment with 1) vehicle only; 2) tadalafil+ambrisentan and vehicle; and 3) vehicle and Compound 1 did not affect levels of PDGFB gene expression significantly. In contrast, combination treatment with tadalafil, ambrisentan, and Compound 1 increased PDGFB gene expression by approximately 70%. FIG. 6 shows that the group treated with tadalafil, ambrisentan, and Compound 1 exhibited increased lung gene expression of PDGFRB compared to the control and other treatment groups.

Combination treatment with tadalafil 10 mg/kg and ambrisentan 10 mg/kg by gavage (TA-V, n=8) once daily for four weeks decreased RVSP by 31% compared to treatment with only the vehicle (V-V, n=9) in the AAV-PDGFB overexpression SU5416 hypoxia rat model of PH. The RVSP in the V-V group was 62.6±4.1 mmHg, and the RSVP of the TA-V group was 42.9±2.2 mm Hg. A dry powder formulation of Compound 1 was administered by passive inhalation at an average dose of 0.6 mg/kg twice a day for four weeks decreased right ventricular systolic pressure by 29% compared to the vehicle treated animals (RVSP 44.3±1.9 mm Hg, n=11). Treatment with 10 mg/kg of tadalafil and 10 mg/kg of ambrisentan daily by gavage combined with inhaled Compound 1 twice daily for four weeks (TA-PK) decreased RVSP by 47% relatively to the V-V group (RVSP 33.2±1.2 mm Hg TA-PK n=9) (p=0.002 TA-PK vs. V-V, p=0.006 TA-V vs. V-V, and p=0.005 V-PK vs V-V). RVSP was not obtained in 1 rat in the V-PK group and 3 rats in the TA-PK group.

Figure 7:
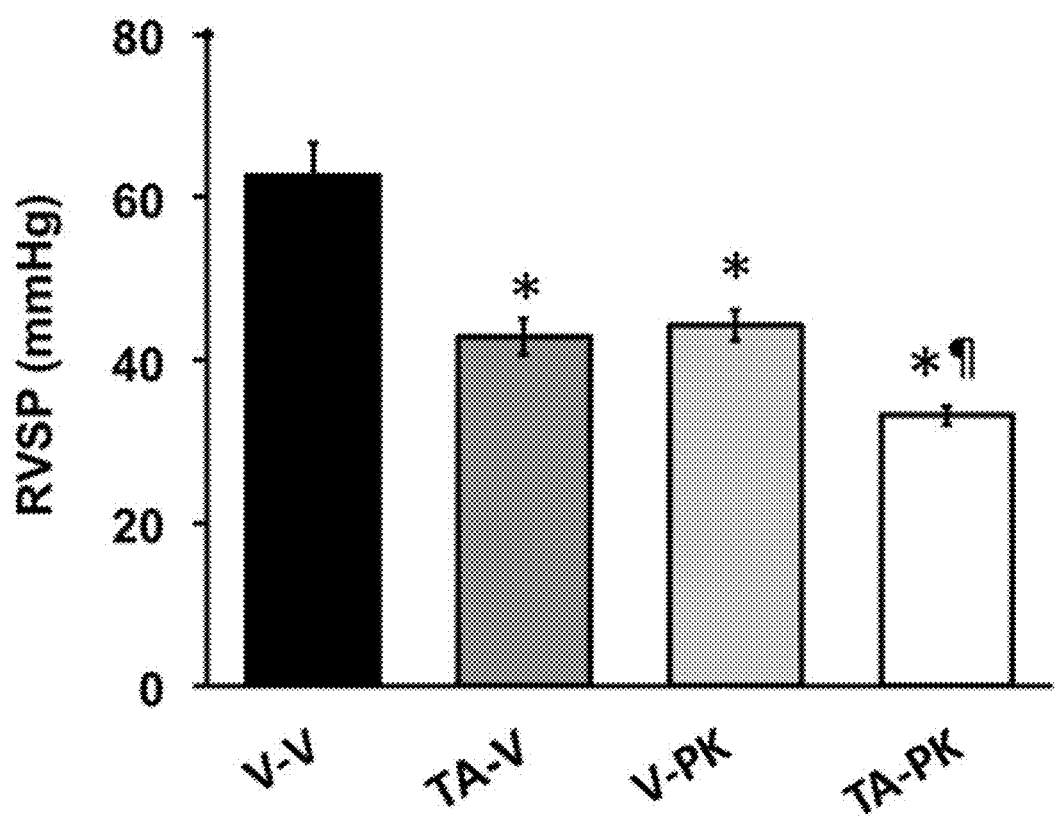
FIG. 7 shows the effect of combination therapy of tadalafil, ambrisentan, and Compound 1 on the % reduction of right ventricular systolic pressure (RVSP).

FIG. 7 shows that treatment with tadalafil, ambrisentan, and Compound 1 exhibited the greatest % reduction of RVSP compared to the control and other treatment groups. *p<0.01 vs V-V; ¶ p<0.01 vs TA-V and V-PK. TABLE 4 summarizes the effects of treatment on reduction of RVSP. Abbreviations: AVG=average; SEM=standard error of the mean.

TABLE 4

| Group | n | AVG RVSP (mm Hg) | SEM | % Reduction RVSP |
|---|---|---|---|---|
| V-V | 9 | 62.64 | 4.07 | n/a |
| TA-V | 8 | 42.89 | 2.23 | 32 |
| V-PK | 11 | 44.30 | 1.88 | 29 |
| TA-PK | 9 | 33.24 | 1.15 | 47 |

Figure 8:
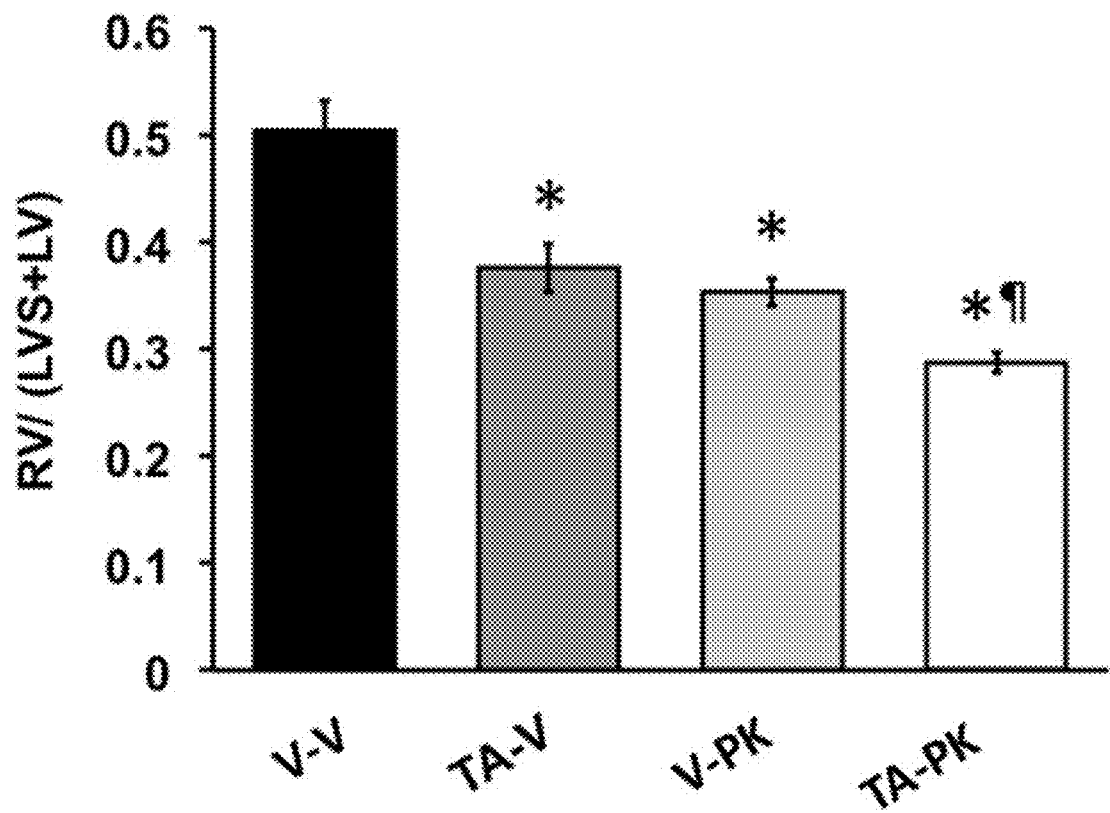
FIG. 8 shows the effect of combination therapy of tadalafil, ambrisentan, and Compound 1 on right ventricular hypertrophy (RV/(LV+IVS)).

Right ventricular hypertrophy was also decreased in the treatment groups, as shown by the ratio of RV weight divided by the LV plus interventricular septum weight (RV/(LV+IVS)). V-V (n=9) 0.50±0.03; TA-V (n=8), 0.38±0.02; V-PK (n=11), 0.36±0.01; and TA-PK (n=9), 0.28±0.01. Compared to the vehicle (V-V) group, the RV/(LV+IVS) ratios were decreased by 25% in the TA and V-PK groups, and by 27% in the TA-PK group. FIG. 8 shows that treatment with tadalafil, ambrisentan, and Compound 1 exhibited the greatest reduction in right ventricular hypertrophy (RV/(LV+IVS)) compared to the control and other treatment groups. *p<0.01 vs V-V; ¶ p<0.01 vs TA-V and V-PK.

Figure 9:
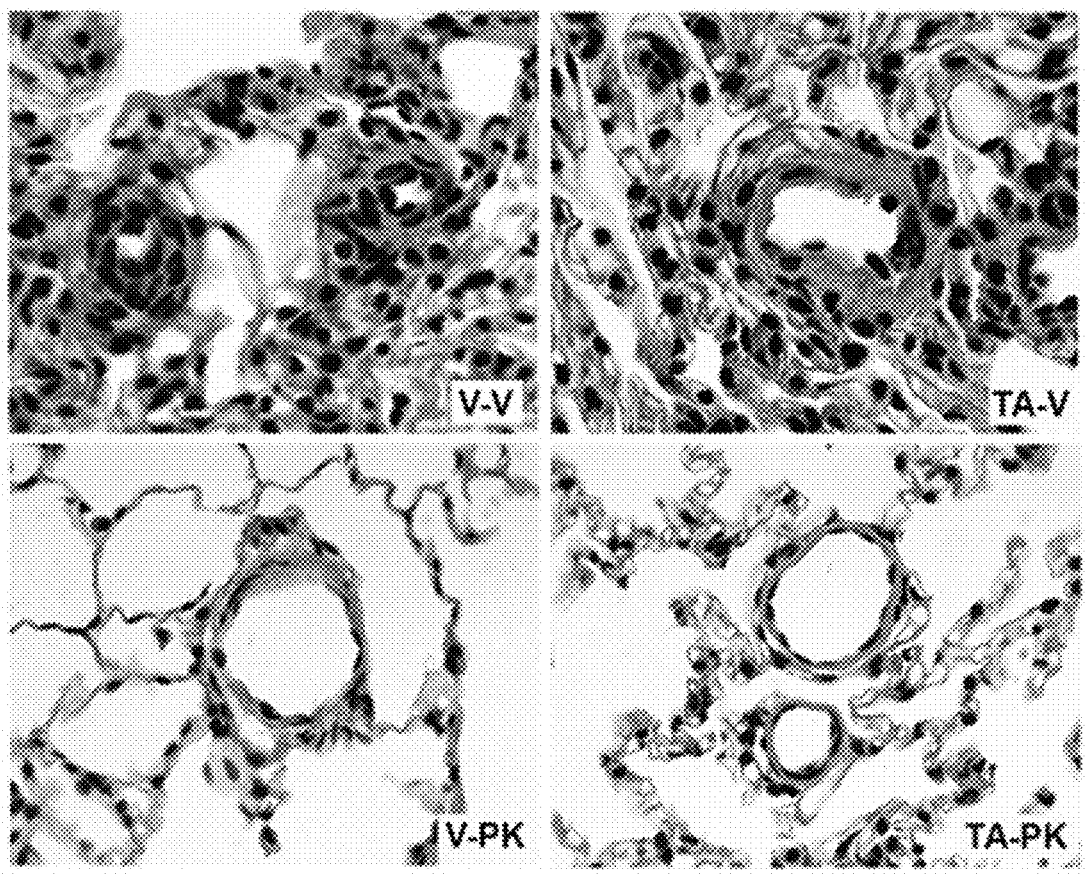
FIG. 9 shows haemotoxylin and eosin stained lung sections comparing lumen and media areas of pulmonary artioles, demonstrating the effect of mono and combination therapy of tadalafil, ambrisentan, and Compound 1 on the lumen/media ratio.
Figure 10:
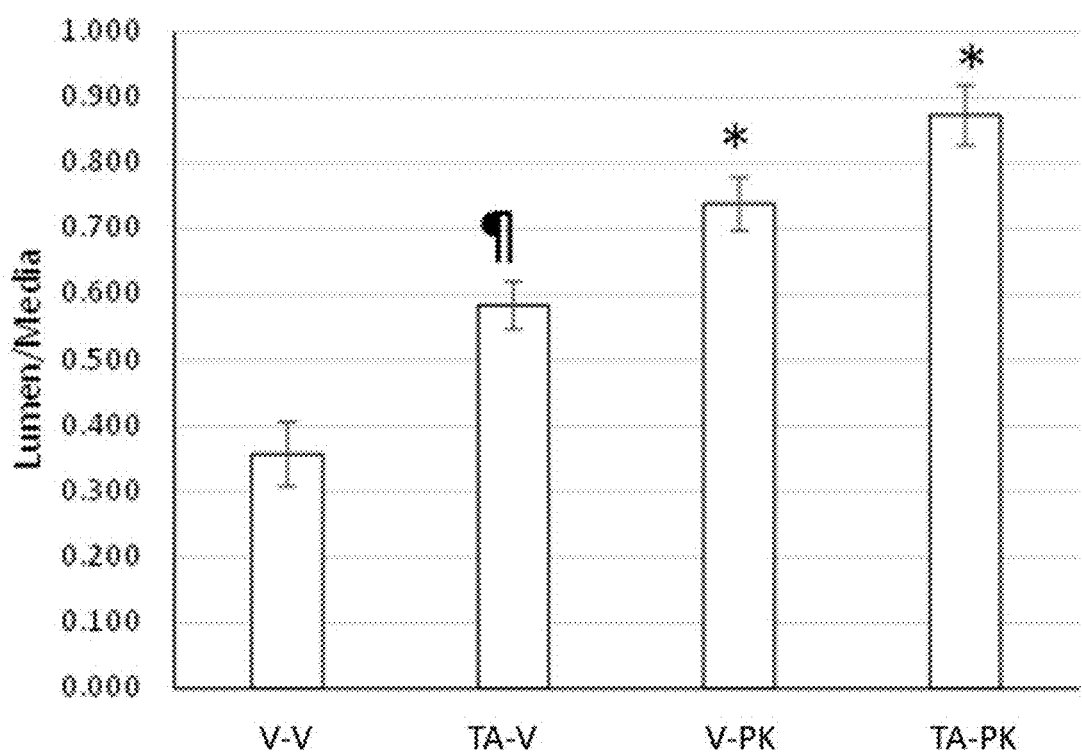
FIG. 10 compares the effect of mono and combination therapy of tadalafil, ambrisentan, and Compound 1 on the lumen/media ratio.

The lumen/media ratio of pulmonary arterioles was improved by treatment with tadalafil plus ambrisentan, inhaled Compound 1, and the combination of tadalafil plus ambrisentan and inhaled Compound 1. V-V (n=9) 0.36±0.05; TA-V (n=8) 0.58±0.04; V-PK (n=12) 0.76±0.04; TA-PK (n=12), 0.83±0.05. FIG. 9 shows H&E stained lung sections comparing lumen and media areas of pulmonary artioles, which demonstrates that treatment with Compound 1 or treatment with tadalafil, ambrisentan, and Compound 1 improved the lumen/media ratio of pulmonary arterioles compared to the control group and group treated with only tadalafil and ambrisentan. FIG. 10 compares the effect of mono and combination therapy of tadalafil, ambrisentan, and Compound 1 on the lumen/media ratio. The data show that the TA-PK group exhibited an increased lumen/media ratio compared to the V-V, TA-V, and V-PK treatment groups. *p<0.0001 vs TA-PK vs. V-V, and V-PK vs. V-V; ¶ p=0.002 vs TA-V vs V-V.

Figure 11:
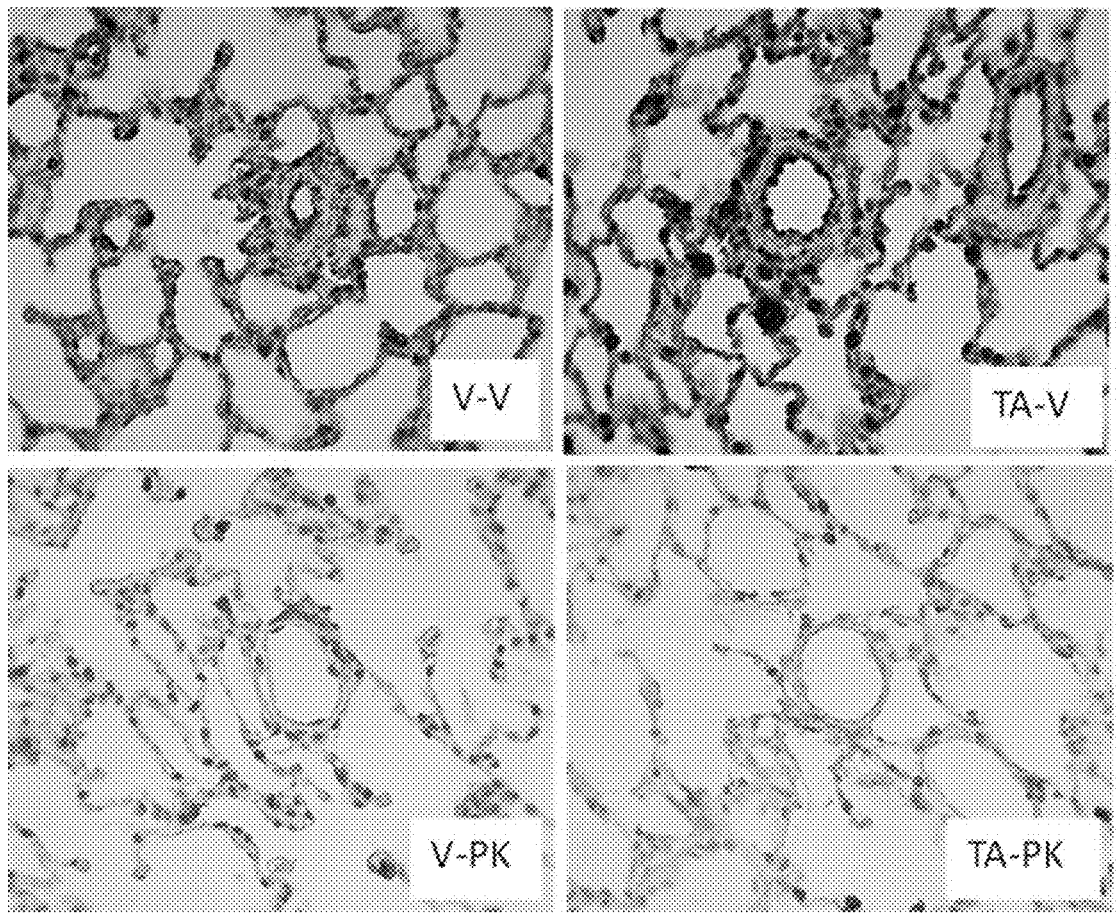
FIG. 11 shows the effect of mono and combination therapy of tadalafil, ambrisentan, and Compound 1 on the phosphorylation of PDGFRβ (Y1021).
Figure 12:
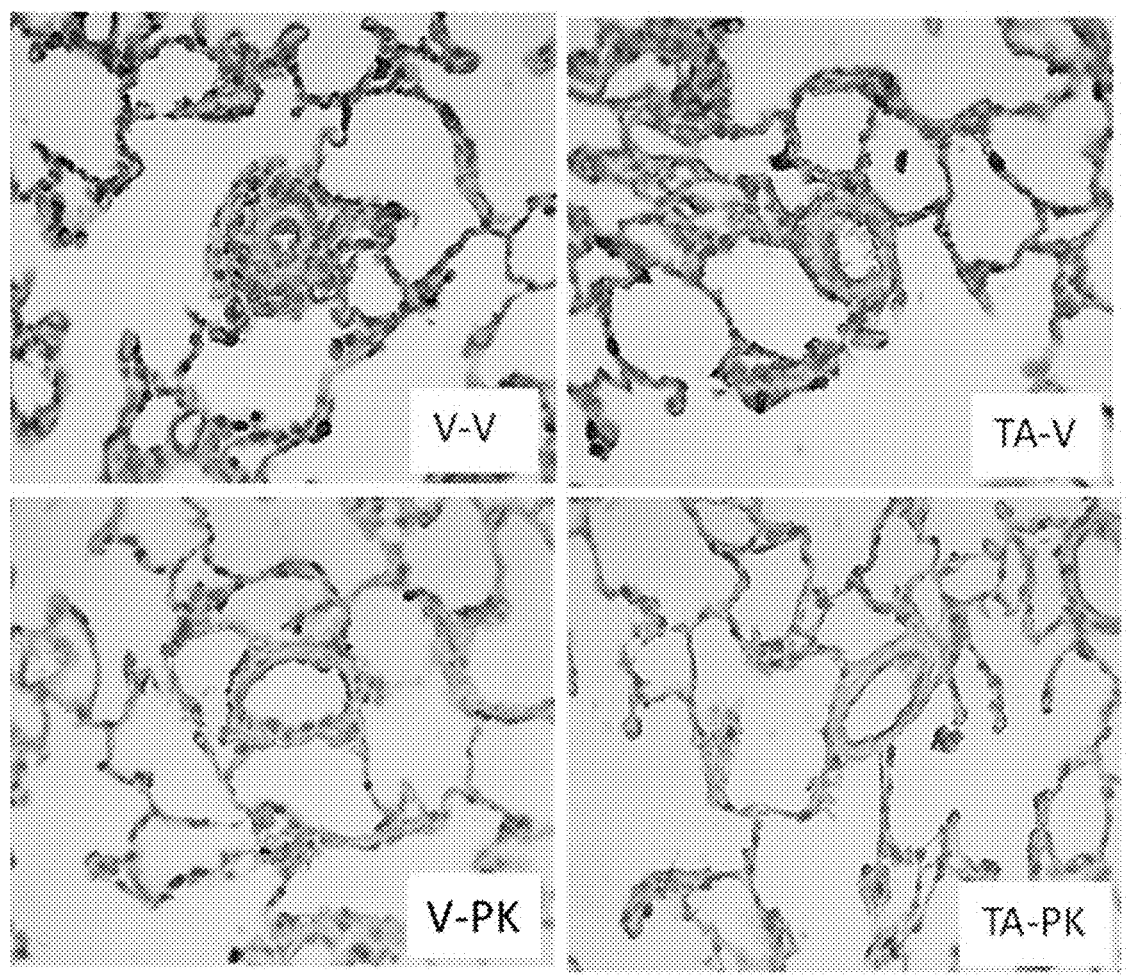
FIG. 12 shows the effect of mono and combination therapy of tadalafil, ambrisentan, and Compound 1 on the phosphorylation of PDGFRα (Y751).
Figure 13:
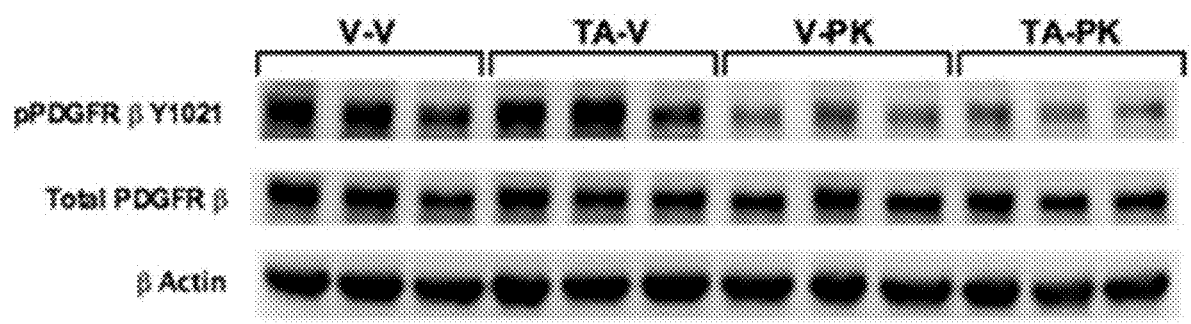
FIG. 13 shows effect of mono and combination therapy of tadalafil, ambrisentan, and Compound 1 in a Western blot analysis of phosphorylated vs. total PDGFRβ with actin controls.

Immunohistochemistry studies demonstrated a decrease in phosphorylated PDGFRβ (Y1021) and phosphorylated PDGFRα (Y751) in the lungs of rats treated with inhaled Compound 1 in both the V-PK and TA-PK groups. FIG. 11 shows that the V-PK and TA-PK groups exhibited decreases in pPDGFRβ (Y1021) compared to the V-V and TA-V treatment groups. FIG. 12 shows that the V-PK and TA-PK groups exhibited decreases in pPDGFRα (Y751) compared to the V-V and TA-V treatment groups. Western blot analyses also demonstrated decreases in pPDGFRβ (Y1021) in the groups treated with inhaled Compound 1 in the V-PK and TA-PK groups. FIG. 13 shows Western blot analyses demonstrating that the V-PK and TA-PK treatment groups exhibited decreased levels of pPDGFRβ (Y1021) compared the V-V and TA-V treatment groups. FIG. 13 also shows that the V-PK and TA-PK treatment groups exhibited decreased levels of pPDGFRβ (Y1021) compared to the level of total PDGFRβ and β actin controls.

Figure 14:
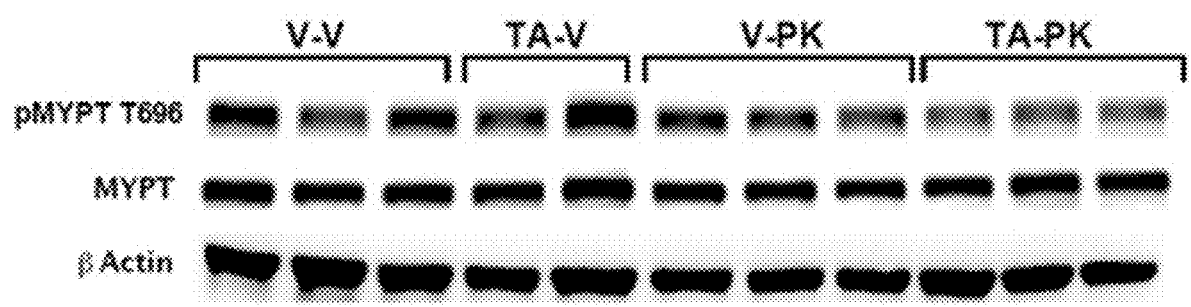
FIG. 14 shows Western blots depicting the decrease in phosphorylation of MYPT in the group treated with tadalafil, ambrisentan, and inhaled Compound 1 compared to the vehicle only group, and the tadalafil and ambrisentan group.
Figure 15:
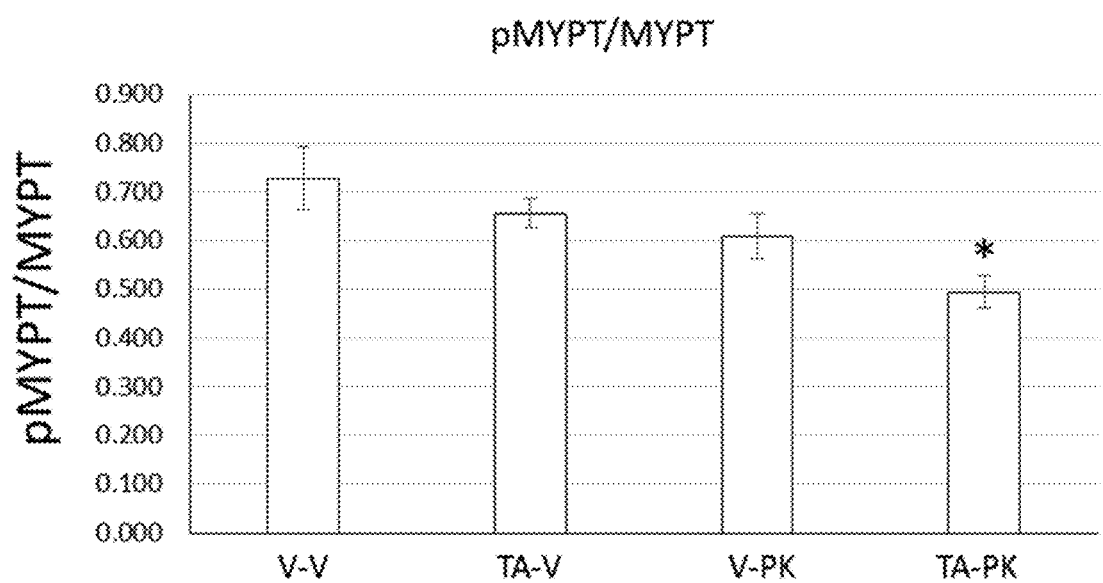
FIG. 15 shows the effect of groups treated with vehicle only; tadalafil and ambrisentan; Compound 1; and tadalafil, ambrisentan, and Compound 1 on the phosphorylation of MYPT.

A decrease in phosphorylation of myosin light chain phosphatase (pMYPT) was also observed in the group treated with tadalafil, ambrisentan, and inhaled Compound 1 (TA-PK, n=9) compared to the vehicle only group (V-V) and the tadalafil and ambrisentan treated group (TA-V, n=8). FIG. 14 shows Western blots depicting the decrease in phosphorylation of MYPT in the group treated with tadalafil, ambrisentan, and inhaled Compound 1 compared to the vehicle only group, and the tadalafil and ambrisentan group. FIG. 15 shows that the TA-PK treatment group exhibited a decreased ratio of pMYPT/MYP compared to the V-V, TA-V, and V-PK treatment groups. * p=0.027 TA-PK vs TA-V, p=0.016 TA-PK vs V-V, Kruskall Wallis analysis.

Figure 16:
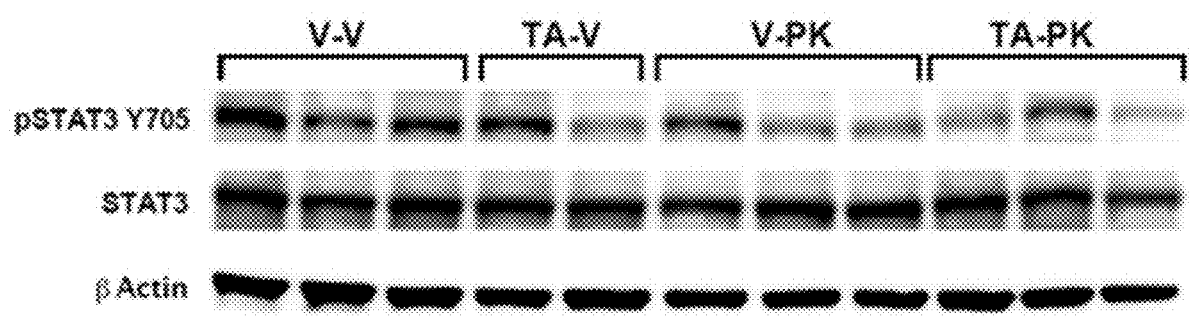
FIG. 16 shows Western blots depicting the decrease in phosphorylation of STAT3 relative to total STAT3 (pSTAT3/STAT3) in the treatment groups.
Figure 17:
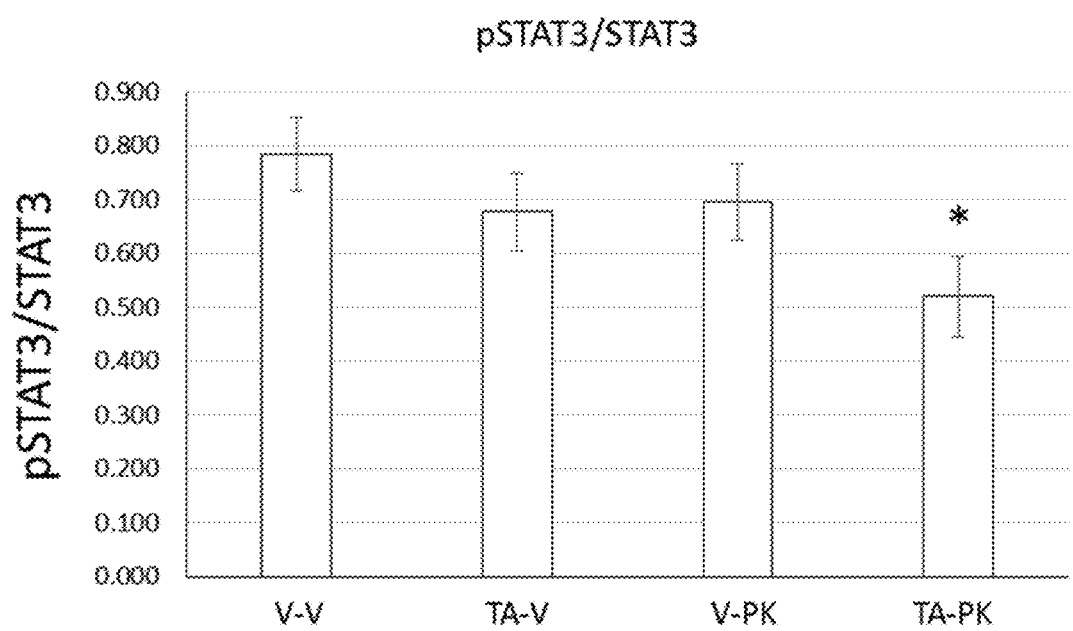
FIG. 17 shows the effect of groups treated with vehicle only; tadalafil and ambrisentan; Compound 1; and tadalafil, ambrisentan, and Compound 1 on the phosphorylation of STAT3 relative to total STAT3 (pSTAT3/STAT3).

A decrease in the phosphorylation of STAT3 (pSTAT3) was observed in the group treated with tadalafil, ambrisentan, and inhaled Compound 1 (TA-PK, n=9) compared to the vehicle only group (V-V, n=9). FIG. 16 shows a Western blot analysis of the treatment groups, which demonstrates that the group treated with TA-PK exhibited the greatest decrease in pSTAT3 compared to the V-V, TA-V, and V-PK treatment groups. FIG. 17 shows that the TA-V and V-PK group had similar decreases in pSTAT3, and that the TA-PK treatment group had the greatest decrease in the ratio of pSTAT3/STAT3. *p=0.04 by Dunnett's test.

Figure 18:
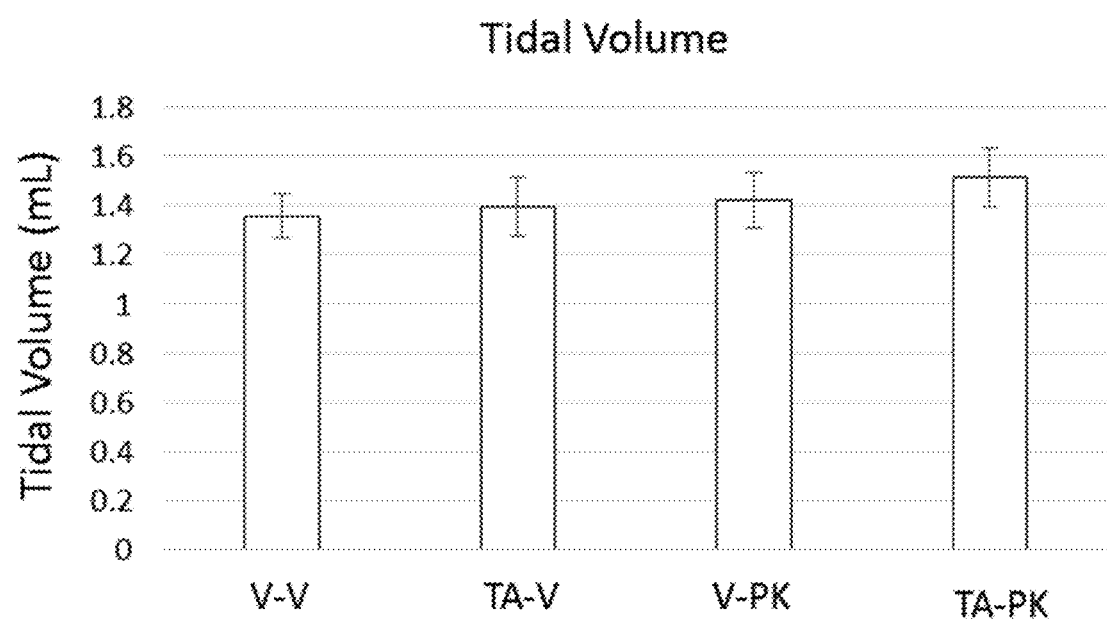
FIG. 18 shows the effect of mono and combination treatment of tadalafil, ambrisentan, and Compound 1 on tidal volume.
Figure 19:
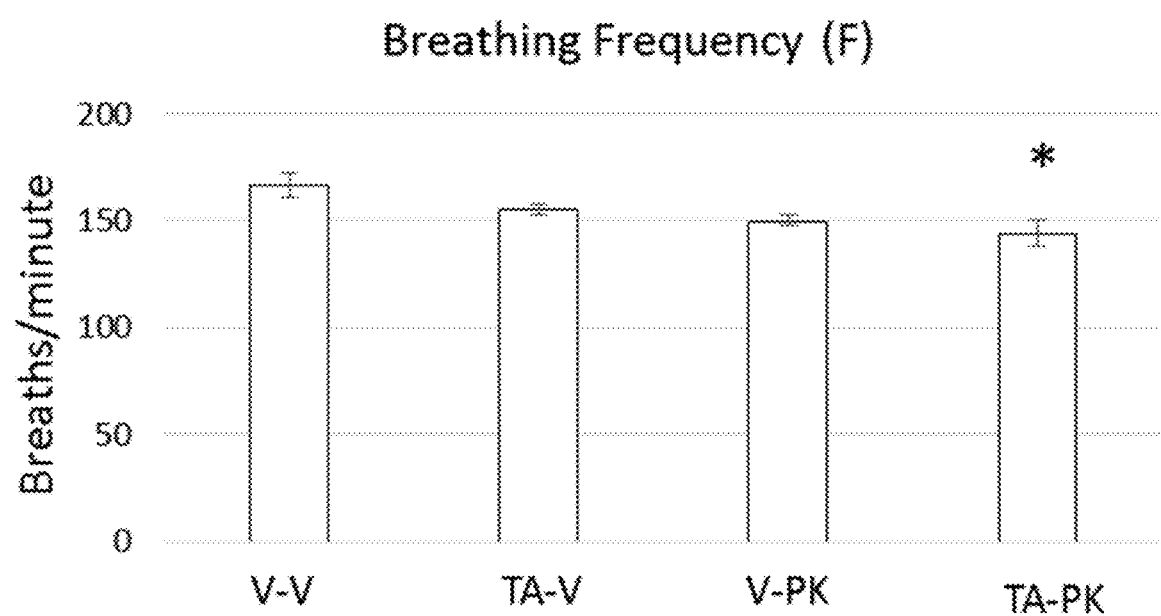
FIG. 19 shows the effect of mono and combination treatment of tadalafil, ambrisentan, and Compound 1 on breathing frequency.
Figure 20:
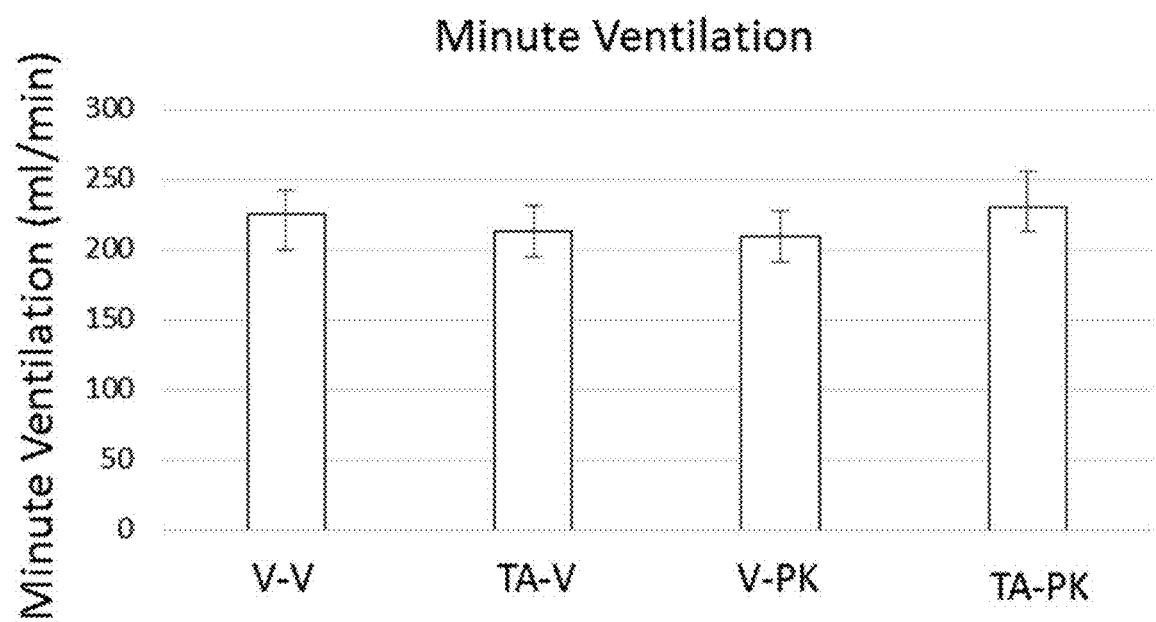
FIG. 20 shows the effect of mono and combination treatment of tadalafil, ambrisentan, and Compound 1 on minute ventilation.
Figure 21:
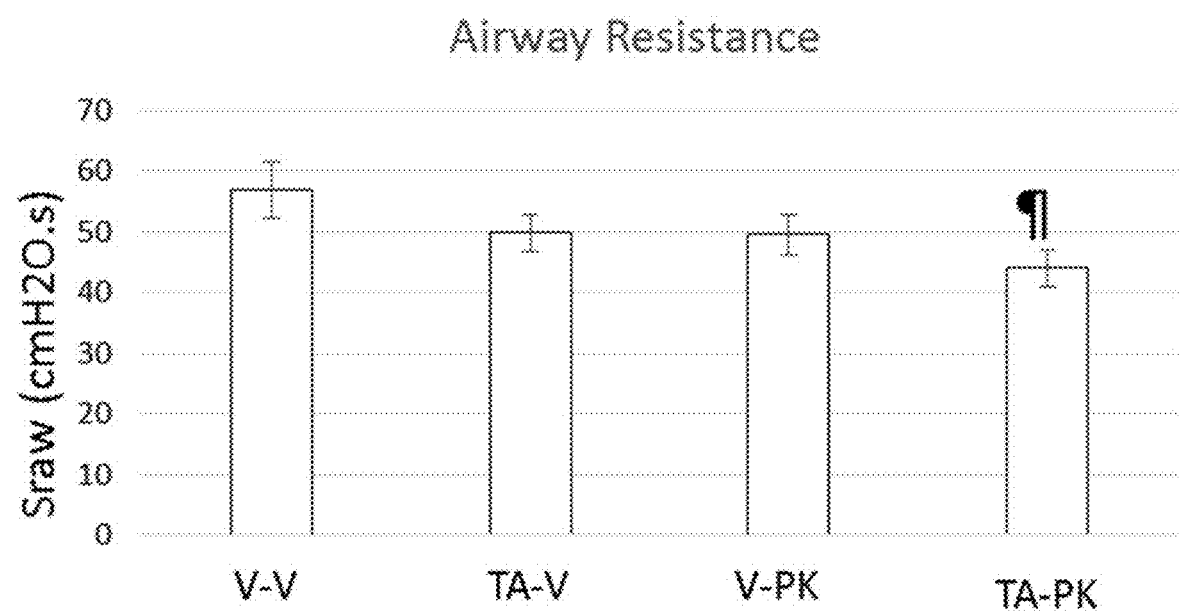
FIG. 21 shows the effect of mono and combination treatment of tadalafil, ambrisentan, and Compound 1 on airway resistance.

Plethysmography studies demonstrated a trend toward increased tidal volume in the V-PK and TA-PK groups. A significant decrease in breathing rate in the TA-PK group was observed without a significant change in MV. A significant decrease in airway resistance was observed in the TA-PK group compared to the V-V group. FIG. 18 shows that treatment with TA-PK resulted in a slight increase in tidal volume compared to the V-V, TA-V, and V-PK treatment groups. FIG. 19 shows that treatment with TA-PK decreased the breathing frequency breathing frequency (breaths/min) of the group compared to the V-V, TA-V, and V—PK groups. *p=0.002 TA-PK vs V-V (Bonferroni correction for multiple group comparison. FIG. 20 shows that treatment with TA-V and V-PK resulted in a small decrease in minute ventilation compared to the V-V group; the group treated with TA-PK exhibited no substantial change in minute ventilation compared to the V-V group. FIG. 21 shows that treatment with TA-PK resulted in a decrease in airway resistance (Sraaw) compared to the V-V, TA-V, and V-PK treatment groups. ¶ p=0.047 TA-PK vs V-V (Dunnett's test).

Embodiments

The following non-limiting embodiments provide illustrative examples of the invention, but do not limit the scope of the invention.

Embodiment 1

A method of treating a condition, the method comprising administering to a subject in need thereof a therapeutically-effective amount of a tyrosine kinase inhibitor, a therapeutically-effective amount of a phosphodiesterase type 5 (PDEV) inhibitor, and a therapeutically-effective amount of an endothelin receptor antagonist.

Embodiment 2

The method of embodiment 1, wherein the subject is human.

Embodiment 3

The method of embodiment 1 or 2, wherein the tyrosine kinase inhibitor is of the formula:

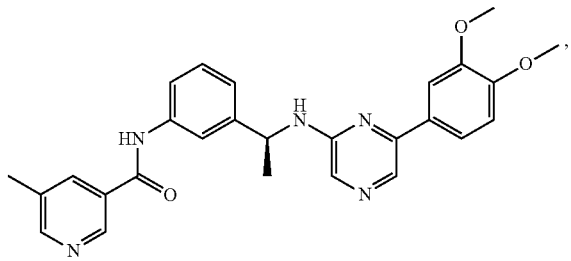

or a pharmaceutically-acceptable salt thereof.

Embodiment 4

The method of any one of embodiments 1-3, wherein the PDEV inhibitor is sildenafil or a pharmaceutically-acceptable salt thereof.

Embodiment 5

The method of any one of embodiments 1-3, wherein the PDEV inhibitor is tadalafil or a pharmaceutically-acceptable salt thereof.

Embodiment 6

The method of any one of embodiments 1-3, wherein the PDEV inhibitor is vardenafil of a pharmaceutically-acceptable salt thereof.

Embodiment 7

The method of any one of embodiments 1-6, wherein the endothelin receptor antagonist is a selective $ET_A$ receptor antagonist.

Embodiment 8

The method of any one of embodiments 1-7, wherein the selective $ET_A$ receptor antagonist is ambrisentan or a pharmaceutically-acceptable salt thereof.

Embodiment 9

The method of any one of embodiments 1-6, wherein the endothelin receptor antagonist is a dual antagonist.

Embodiment 10

The method of any one of embodiments 1-6 and 9, wherein the dual antagonist is macitentan or a pharmaceutically-acceptable salt thereof.

Embodiment 11

The method of any one of embodiments 1-10, wherein the administration of the tyrosine kinase inhibitor is by inhalation.

Embodiment 12

The method of any one of embodiments 1-11, wherein the administration of the tyrosine kinase inhibitor is by an inhaler.

Embodiment 13

The method of any one of embodiments 1-11, wherein the administration of the tyrosine kinase inhibitor is by a nebulizer.

Embodiment 14

The method of any one of embodiments 1-11, wherein the administration of the tyrosine kinase inhibitor is by an atomizer.

Embodiment 15

The method of any one of embodiments 1-14, wherein the administration of the PDEV inhibitor and endothelin receptor antagonist is oral.

Embodiment 16

The method of any one of embodiments 1-15, wherein the therapeutically-effective amount of the tyrosine kinase inhibitor is from about 0.25 mg/kg to about 1 mg/kg per day.

Embodiment 17

The method of any one of embodiments 1-16, wherein the therapeutically-effective amount of the PDEV inhibitor is from about 20 mg to about 40 mg per day.

Embodiment 18

The method of any one of embodiments 1-17, wherein the therapeutically-effective amount of the endothelin receptor antagonist is about 5 mg to about 10 mg per day.

Embodiment 19

The method of any one of embodiments 1-18, wherein the condition is a pulmonary disorder.

Embodiment 20

The method of any one of embodiments 1-19, wherein the condition is pulmonary hypertension.

Embodiment 21

The method of any one of embodiments 1-20, wherein the condition is pulmonary arterial hypertension.

Embodiment 22

The method of any one of embodiments 1-21, wherein the tyrosine kinase inhibitor is formulated as a dry powder for inhalation.

Embodiment 23

The method of any one of embodiments 1-3, 5, 7, 8, and 11-22, wherein the PDEV inhibitor is tadalafil or a pharmaceutically-acceptable salt thereof, and the endothelin receptor antagonist is ambrisentan or a pharmaceutically-acceptable salt thereof.

Embodiment 24

The method of any one of embodiments 1-23, wherein the therapeutically-effective amount of the tyrosine kinase inhibitor is about 0.25 mg/kg/day to about 0.5 mg/day, the therapeutically-effective amount of the PDEV inhibitor is about 1 mg/kg, and the therapeutically-effective amount of the endothelin receptor antagonist is about 1 mg/kg.

Embodiment 25

The method of any one of embodiments 1-3, 5, 7, 8, and 11-23, wherein the tadalafil or a pharmaceutically-acceptable salt thereof and ambrisentan or a pharmaceutically-acceptable salt thereof are administered orally.

Embodiment 26

The method of any one of embodiments 1-25, wherein the tyrosine kinase inhibitor is administered by inhalation.

Embodiment 27

The method of any one of embodiments 1-26, further comprising administering to the subject a therapeutically-effective amount of a soluble guanylate cyclase stimulator.

Embodiment 28

The method of any one of embodiments 1-27, wherein the soluble soluble guanylate cyclase stimulator is riociguat or a pharmaceutically-acceptable salt thereof.

Embodiment 29

The method of any one of embodiments 1-24, wherein the soluble guanylate cyclase inhibitor is vericiguat or a pharmaceutically-acceptable salt thereof.

What is claimed is:

1. A method of treating pulmonary arterial hypertension, the method comprising administering to a subject in need thereof:
   a) a therapeutically-effective amount of a tyrosine kinase inhibitor, wherein the tyrosine kinase inhibitor is of the formula:

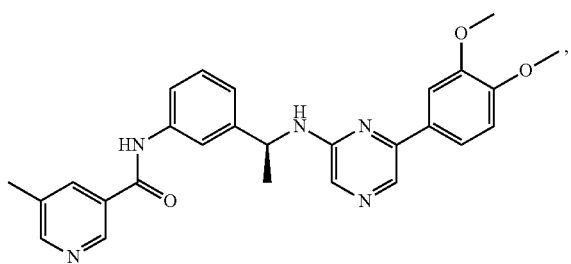

or a pharmaceutically-acceptable salt thereof;
   b) a therapeutically-effective amount of a PDEV inhibitor, wherein the PDEV inhibitor is sildenafil, tadalafil, vardenafil, or a pharmaceutically acceptable salt thereof;
   c) a therapeutically-effective amount of an endothelin receptor antagonist, wherein the endothelin receptor antagonist is ambrisentan, macitentan, or a pharmaceutically acceptable salt thereof; and
   d) a therapeutically-effective amount of a soluble guanylate cyclase stimulator.

2. The method of claim 1, wherein the subject is human.

3. The method of claim 1, wherein the soluble guanylate cyclase stimulator is riociguat or a pharmaceutically acceptable salt thereof.

4. The method of claim 1, wherein the soluble guanylate cyclase stimulator is vericiguat or a pharmaceutically acceptable salt thereof.

5. The method of claim 1, wherein the PDEV inhibitor is sildenafil or a pharmaceutically-acceptable salt thereof.

6. The method of claim 1, wherein the PDEV inhibitor is tadalafil or a pharmaceutically-acceptable salt thereof.

7. The method of claim 1, wherein the PDEV inhibitor is vardenafil or a pharmaceutically-acceptable salt thereof.

8. The method of claim 1, wherein the endothelin receptor antagonist is ambrisentan or a pharmaceutically-acceptable salt thereof.

9. The method of claim 1, wherein the endothelin receptor antagonist is macitentan or a pharmaceutically acceptable salt thereof.

10. The method of claim 1, wherein the administration of the tyrosine kinase inhibitor is by inhalation.

11. The method of claim 1, wherein the administration of the tyrosine kinase inhibitor is by an inhaler.

12. The method of claim 1, wherein the administration of the tyrosine kinase inhibitor is by a nebulizer.

13. The method of claim 1, wherein the administration of the tyrosine kinase inhibitor is by an atomizer.

14. The method of claim 1, wherein the administration of the PDEV inhibitor, the endothelin receptor antagonist, and the soluble guanylate cyclase stimulator is oral.

15. The method of claim 1, wherein the therapeutically-effective amount of the tyrosine kinase inhibitor is from about 0.25 mg/kg to about 1 mg/kg per day.

16. The method of claim 1, wherein the therapeutically-effective amount of the PDEV inhibitor is from about 20 mg to about 40 mg per day.

17. The method of claim 1, wherein the therapeutically-effective amount of the endothelin receptor antagonist is about 5 mg to about 10 mg per day.

18. The method of claim 1, wherein the tyrosine kinase inhibitor is formulated as a dry powder.

19. The method of claim 1, wherein the therapeutically-effective amount of the tyrosine kinase inhibitor is about 0.25 mg/kg/day to about 1 mg/kg/day, the therapeutically-effective amount of the PDEV inhibitor is about 1 mg/kg, and the therapeutically-effective amount of the endothelin receptor antagonist is about 1 mg/kg.

20. The method of claim 19, wherein the tyrosine kinase inhibitor is administered by inhalation.

21. The method of claim 1, wherein the tadalafil or pharmaceutically-acceptable salt thereof and the ambrisentan or pharmaceutically-acceptable salt thereof are administered orally.

* * * * *